(12) United States Patent
Koo et al.

(10) Patent No.: US 10,441,291 B2
(45) Date of Patent: Oct. 15, 2019

(54) DEVICES AND METHODS FOR TREATING ACUTE KIDNEY INJURY

(71) Applicant: RENALPRO MEDICAL, INC., Palo Alto, CA (US)

(72) Inventors: Charles Char-Lin Koo, Palo Alto, CA (US); Tsung-Chun Lee, New Taipei (TW); Wen-Pin Shih, Taipei (TW)

(73) Assignee: RenalPro Medical, Inc., Santa Clara, CA (US)

( * ) Notice: Subject to any disclaimer, the term of this patent is extended or adjusted under 35 U.S.C. 154(b) by 0 days.

(21) Appl. No.: 15/969,050

(22) Filed: May 2, 2018

(65) Prior Publication Data

US 2018/0250015 A1  Sep. 6, 2018

Related U.S. Application Data

(63) Continuation of application No. PCT/US2017/031153, filed on May 4, 2017.
(Continued)

(51) Int. Cl.
*A61M 31/00* (2006.01)
*A61B 17/12* (2006.01)
(Continued)

(52) U.S. Cl.
CPC .......... *A61B 17/12136* (2013.01); *A61B 6/12* (2013.01); *A61B 6/484* (2013.01);
(Continued)

(58) Field of Classification Search
CPC .. A61M 1/3653; A61M 1/1072; A61M 1/125; A61M 1/107; A61M 1/1034; A61M 1/122; A61M 1/1018; A61M 1/1096; A61M 25/00; A61M 25/10; A61M 25/1011; A61M 25/0075; A61M 5/007; A61M 2025/1052; A61M 2025/1095; A61M 2025/0244; A61M 2025/0266; A61M 2025/3331; A61M 2025/16; A61B 17/12136; A61B 17/1204; A61B 17/12109; A61B 17/12172; A61B 17/12031; A61B 17/12036; A61B 17/12045; A61B 17/12131; A61B 6/12; A61B 6/484; A61B 25/0108;
(Continued)

(56) References Cited

U.S. PATENT DOCUMENTS 5,879,499 A  3/1999 Corvi
6,036,697 A  3/2000 Dicaprio
(Continued)

FOREIGN PATENT DOCUMENTS

CN  201692487 U  1/2011
JP  2005500862 A  1/2005
(Continued)

OTHER PUBLICATIONS

"Office action dated Nov. 15, 2018 for U.S. Appl. No. 15/189,460."

*Primary Examiner* — Elmer M Chao
(74) *Attorney, Agent, or Firm* — Wilson Sonsini Goodrich & Rosati

(57) ABSTRACT

A catheter devices/systems and methods therefrom are described herein for treating acute kidney injury, especially the contrast-induced acute kidney injury wherein the devices may prevent the contrast dyes from entering into kidney and/or facilitate blood flow of kidney by said catheter system.

19 Claims, 36 Drawing Sheets

Related U.S. Application Data

(60) Provisional application No. 62/331,975, filed on May 4, 2016, provisional application No. 62/372,450, filed on Aug. 9, 2016.

(51) Int. Cl.

| | |
|---|---|
| *A61B 6/12* | (2006.01) |
| *A61B 6/00* | (2006.01) |
| *A61M 25/01* | (2006.01) |
| *A61M 25/10* | (2013.01) |
| *A61B 90/00* | (2016.01) |
| *A61B 17/00* | (2006.01) |
| *A61M 5/00* | (2006.01) |
| *A61M 25/09* | (2006.01) |

(52) U.S. Cl.
CPC .... *A61B 17/1204* (2013.01); *A61B 17/12031* (2013.01); *A61B 17/12036* (2013.01); *A61B 17/12045* (2013.01); *A61B 17/12109* (2013.01); *A61B 17/12131* (2013.01); *A61B 17/12172* (2013.01); *A61M 25/0108* (2013.01); *A61M 25/1002* (2013.01); *A61M 25/1011* (2013.01); *A61B 2017/00455* (2013.01); *A61B 2090/3966* (2016.02); *A61M 5/007* (2013.01); *A61M 25/09* (2013.01); *A61M 2025/1052* (2013.01); *A61M 2025/1095* (2013.01); *A61M 2205/0244* (2013.01); *A61M 2205/0266* (2013.01); *A61M 2205/3331* (2013.01); *A61M 2206/16* (2013.01)

(58) Field of Classification Search
CPC . A61B 25/1002; A61B 25/1011; A61B 25/09; A61B 2090/3966; A61B 2017/00455
See application file for complete search history.

(56) References Cited

U.S. PATENT DOCUMENTS

| | | | |
|---|---|---|---|
| 6,251,093 | B1 | 6/2001 | Valley et al. |
| 6,287,315 | B1 | 9/2001 | Wijeratne et al. |
| 6,692,484 | B1 | 2/2004 | Karpiel et al. |
| 6,913,600 | B2 | 7/2005 | Valley et al. |
| 9,861,794 | B2 | 1/2018 | Ringvad et al. |
| 2005/0148997 | A1 | 7/2005 | Valley et al. |
| 2005/0203553 | A1 | 9/2005 | Maschke |
| 2005/0203558 | A1 | 9/2005 | Maschke |
| 2013/0123621 | A1 | 5/2013 | Isham et al. |
| 2014/0051968 | A1 | 2/2014 | Isham et al. |
| 2015/0094609 | A1 | 4/2015 | Jacobson et al. |

FOREIGN PATENT DOCUMENTS

| | | |
|---|---|---|
| WO | WO-9640347 A1 | 12/1996 |
| WO | WO-2010018569 A1 | 2/2010 |
| WO | WO-2016032743 A1 | 3/2016 |

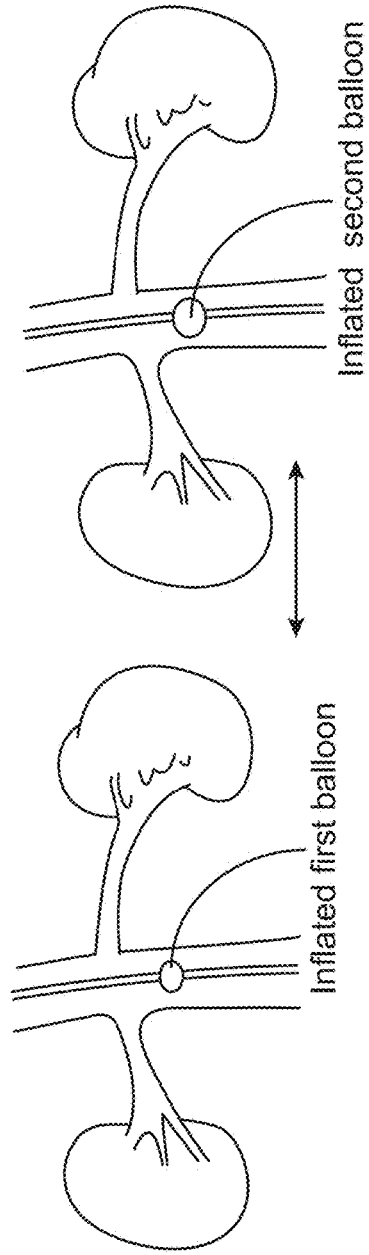
FIG. 14A
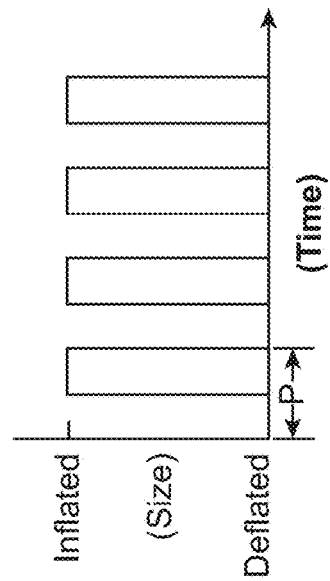
FIG. 14B
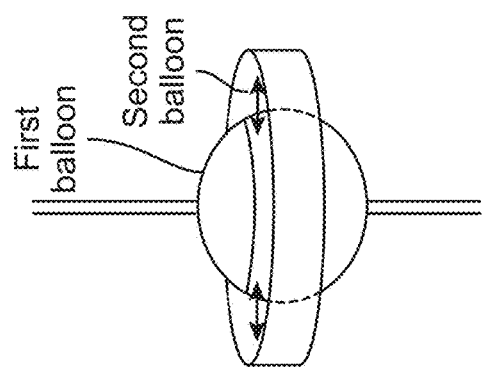

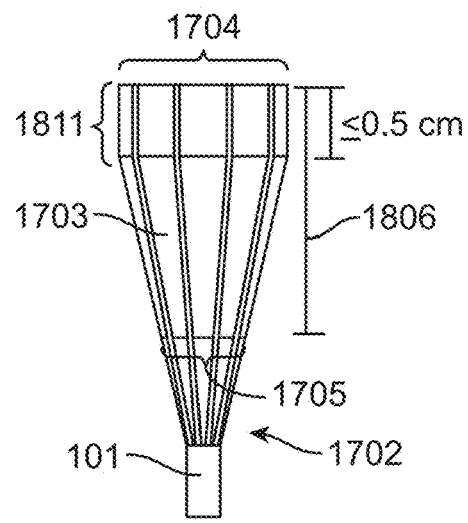
FIG. 18A
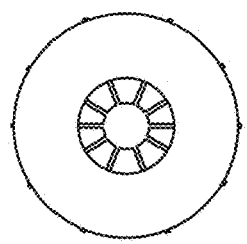 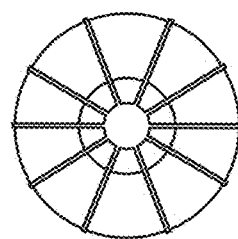
FIG. 18B  FIG. 18C
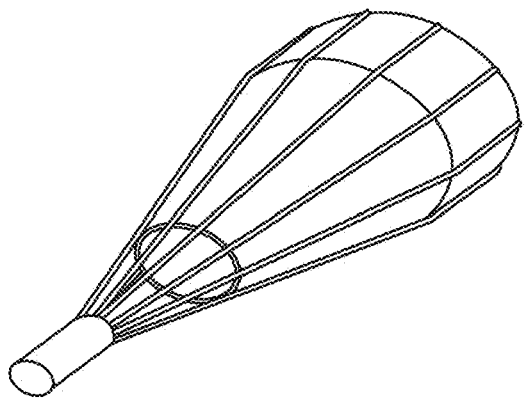
FIG. 18D

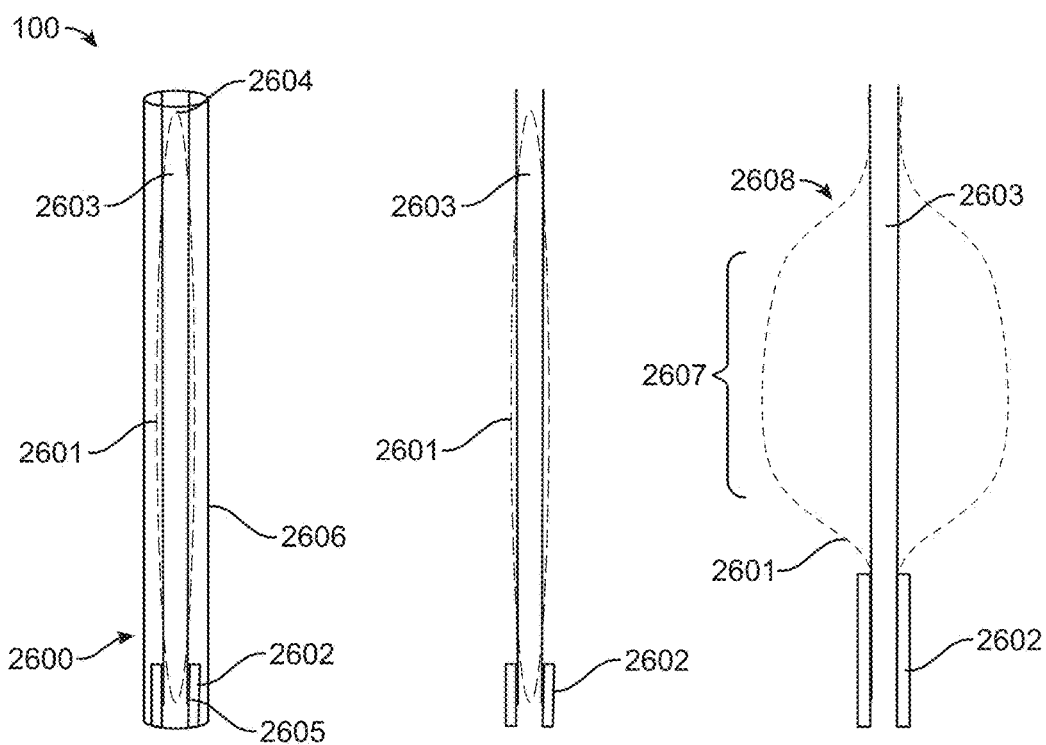

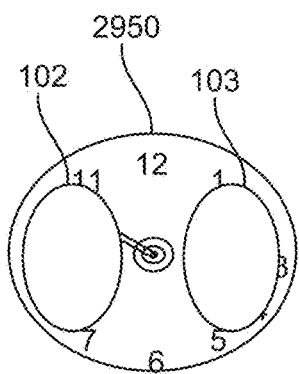 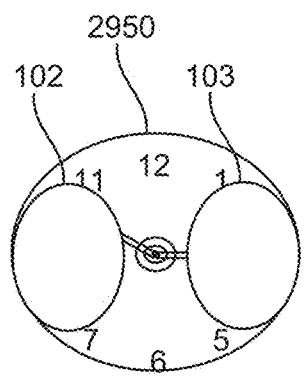
FIG. 29A    FIG. 29B
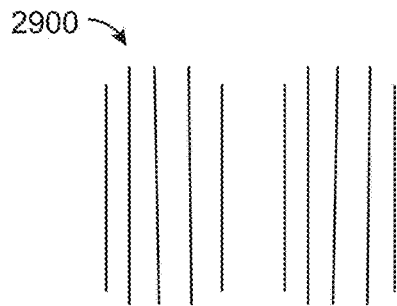 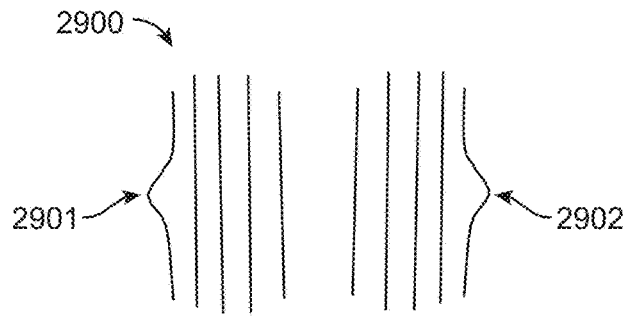
FIG. 29C    FIG. 29D

DEVICES AND METHODS FOR TREATING ACUTE KIDNEY INJURY

CROSS-REFERENCE

This application is a continuation of PCT/US2017/031153, filed on May 4, 2017, which claims the benefit of U.S. Provisional Application No. 62/331,975, filed May 4, 2016, and U.S. Provisional Application No. 62/372,450, filed Aug. 9, 2016, the entire contents of each of which is incorporated herein by reference.

BACKGROUND

Acute kidney injury (AKI), also called acute renal failure (ARF), is a rapid loss of kidney function. The causes of AKI are numerous and may include low blood volume, decreased blood flow to the kidneys, exposure of the kidney to toxic substances, or urinary tract obstruction. AKI is diagnosed on the basis of clinical history and laboratory data. Kidney function may be measured by serum creatinine or urine output, among other tests, and a rapid reduction in either or both of these factors may be diagnosed as AKI.

One possible cause of AKI is the use of intravascular iodinated contrast media or contrast agents. Contrast-induced AKI (CI-AKI) is a common problem in patients receiving intravascular iodine-containing contrast media for angiography. CI-AKI is associated with excessive hospitalization cost, morbidity, and mortality. Clinical procedures involving intravascular iodine-containing contrast media injection may include, for example, percutaneous coronary intervention (PCI), peripheral vascular angiography and intervention, transarterial heart valve interventions, and neurological angiography and intervention. In clinical practice, CI-AKI is diagnosed when serum creatinine levels increase by more than either 25% or 0.5 mg/dL above baseline within 48 to 72 hours of exposure to contrast media in the absence of other culprit etiology for AKI.

Management of AKI hinges on identification and treatment of the underlying cause. Additionally, management of AKI routinely includes avoidance of substances toxic to the kidneys, called nephrotoxins. Nephrotoxins include, for example, non-steroidal anti-inflammatory drugs (NSAIDs), such as ibuprofen, iodinated contrast agents, such as those used for CT scans, many antibiotics, such as gentamicin, and a range of other substances.

Renal function monitoring by serum creatinine and urine output is routinely performed. For example, insertion of a urinary catheter helps monitor urine output and relieves possible bladder outlet obstruction, such as with an enlarged prostate. In prerenal AKI without fluid overload, administration of intravenous fluids is typically the first step to improve renal function. Volume status may be monitored with the use of a central venous catheter to avoid over- or under-replacement of fluid. Should low blood pressure prove a persistent problem in the fluid-replete patient, inotropes such as norepinephrine and dobutamine may be given to improve cardiac output and enhance renal perfusion. Also, while a useful pressor, there is no evidence to suggest that dopamine is of any specific benefit, and may in fact be harmful.

The myriad causes of intrinsic AKI can require specific therapies. For example, intrinsic AKI due to Wegener's granulomatosis may respond to steroid medication while toxin-induced prerenal AKI often responds to discontinuation of the offending agent, which may for example be aminoglycoside, penicillin, NSAIDs, or paracetamol. Obstruction of the urinary tract may also cause AKI and treatment may require relief of the obstruction, for example with a nephrostomy or urinary catheter.

Renal replacement therapy, such as with hemodialysis, may be instituted in some cases of AKI. A systematic review of the literature in 2008 shows no difference in outcomes between the use of intermittent hemodialysis and continuous venovenous hemofiltration (CVVH). Among critically ill patients, intensive renal replacement therapy with CVVH does not appear to improve outcomes compared to less intensive intermittent hemodialysis.

Current prevention strategies for AKI, particularly for CI-AKI, are mainly supportive. They include for example (1) evaluating and stratifying patients with Mehran risk score before performing PCI, (2) avoiding high-osmolar contrast media by using low-osmolar or iso-osmolar contrast media, (3) reducing the amount of contrast media during PCI, (4) applying intravenously isotonic sodium chloride solution or sodium bicarbonate solution hours before and after PCI, and (5) avoiding use of nephrotoxic drugs (such as nonsteroidal anti-inflammatory drugs, aminoglycosides antibiotics, etc.). (See Stevens 1999, Schweiger 2007, Solomon 2010.) However, none of these strategies have proven to be consistently effective in preventing CI-AKI.

SUMMARY

One aspect of the present disclosure may provide a device for treating or reducing the risk of AKI comprising a balloon catheter having at least one balloon, at least one sensor associated with the balloon, and a disturbing means associated with the balloon, wherein the balloon with the disturbing means may generate augmented renal blood flow to avoid renal ischemia and also to dilute the contrast media flowing into kidneys.

Another aspect of the present disclosure may provide a device for treating or reducing the risk of AKI comprising a balloon catheter having at least one balloon, at least one sensor associated with the balloon, and a position indication means, wherein the balloon may occlude the orifice of both sides of renal arteries after inflation while allowing blood flow through the inflated balloon while the device is deployed inside the abdominal aorta of a patient.

Another aspect of the present disclosure may provide a device for treating or preventing acute kidney injury, comprising a catheter having a plurality of balloons, said balloons when inflated, can occlude partially or completely aortic branching arteries, through which aorta blood flows into right and left kidneys. The balloons may be located inside the abdominal aorta. In some embodiments, the balloons can be inflated or deflated, partially or completely. The balloons, when inflated, can divert aorta blood flow from directly flowing into renal arteries and/or occlude partially or completely aortic branching arteries, through which aorta blood flows into right and left renal arteries. The balloons may contact the inner wall of the abdominal aorta, without causing damage to the inner wall of the abdominal aorta and/or not cause blood clot formation. Radio-opaque markers near proximal and distal ends of the balloons on the catheter may be used to guide proper vertical location of the catheter under fluoroscopy. Radio-opaque markers on the balloon membranes may be used to guide proper rotational orientation and proper inflation of the balloons inside the abdominal aorta. The inflation of balloons can be synchronized in chronological sequence with the injection of contrast media by a physician during a cardiac catheterization procedure. The inflation of balloons may be maintained for any given period of time (e.g., five seconds), to allow aorta blood with high concentrated contrast media flowing from supra-renal aorta to infra-renal aorta, without directly flowing into renal arteries. The endovascular catheter can have a central conduit, which allows a guidewire passing through and or allows a coronary catheter passing through.

Another aspect of the present disclosure may provide a device for treating or reducing the risk of CI-AKI comprising a catheter, a position indication means on the catheter, and a flow disturbing means retractable into the catheter, wherein the flow disturbing means may be positioned at the suprarenal aorta of a patient to provide blood flow disturbance to dilute a contrast media before being taken up by the renal arteries.

Another aspect of the present disclosure may provide a method for treating or reducing the risk of CI-AKI comprising inserting a catheter as described above into abdominal aorta, placing the catheter at the suprarenal aorta, and deploying the disturbing means at a position which may allow the disturbing means to provide blood flow disturbance and dilute a contrast media before the contrast media is taken into the renal arteries. In many embodiments, the AKI comprises CI-AKI. In some embodiments, the device may comprise a balloon catheter having a first balloon, a second balloon, and at least one sensor associated with the first balloon. In some embodiments, the device may comprise a balloon catheter having a first balloon, a second balloon, and at least one sensor associated with the second balloon. In some embodiments, the device may further comprise a side aperture for infusing normal saline or medication. The medication infused via the side aperture may be a vasodilatory agent, for example, fenoldopam.

In many embodiments, the sensor may be a pressure sensor. In certain embodiments, the pressure sensor may measure the blood flow pressure. In some embodiments, the sensor may be a size measuring sensor. In some embodiments, the size measuring sensor may measure the size of balloon. In some embodiments, the device may comprise two sensors. In some embodiments, the device may comprise a first sensor at an upper side of the first balloon and a second sensor at a lower side of the first balloon. In some embodiments, the device may comprise a first sensor at an upper side of the second balloon and a second sensor at a lower side of the second balloon. In some embodiments, the sensor may provide data to the control unit to control the size of the first and/or second balloons.

In many embodiments, the balloon catheter may further include a guidewire and a spinning propeller. In some embodiments, the spinning propeller may spin around the central guidewire to generate directional augmented renal artery blood flow toward the kidney. In some embodiments, the spinning propeller may be wing shape or fin shape. In some embodiments, the device may further comprise an additional catheter comprising a guidewire and a spinning propeller to generate directional augmented blood flow to the other kidney. In some embodiments, the additional catheter comprising a spinning propeller may function either independent of or simultaneously with the balloon catheter to generate directional augmented blood flow to each side of kidney.

In another aspect of the present disclosure, a method for treating CI-AKI may be provided. The method may comprise steps of:

inserting the device comprising a balloon catheter having a first balloon, a second balloon, and at least one sensor into abdominal aorta;

placing the balloon catheter at a position which may allow the first balloon to be located at the supra-renal aorta near the orifices of bilateral renal arteries;

inflating the first balloon to occlude the orifice of both sides of renal arteries during the application of contrast media;

deflating the first balloon after the contrast media has been completely employed;

inflating the second balloon to an extent so as not to completely occlude aortic blood flow of the infra-renal aorta near the orifices of the renal arteries;

deflating the second balloon;

and infusing normal saline and/or suitable medication via the side aperture into the supra-renal aorta.

In many embodiments, insertion of the device into the abdominal aorta may be applied either by a trans-femoral artery approach, a trans-brachial artery approach, or by a trans-radial artery approach. In some embodiments, the balloon catheter may further comprise a guidewire and a spinning propeller. In some embodiments, the method may further comprise inserting a guidewire into a renal artery. In some embodiments, the method may further comprise inserting a spinning propeller into a renal artery through the guidewire. In some embodiments, the method may further comprise spinning the spinning propeller around the central guidewire to generate directional augmented renal artery blood flow toward the kidney.

In some embodiments, the present disclosure may provide an inventive device described herein for treating AKI. In certain embodiments, the AKI is CI-AKI. In some embodiments, the device may comprise a balloon catheter having a first balloon, a second balloon, and at least one sensor associated with the second balloon. In some embodiments, the device may comprise two sensors described herein. In some embodiments, the balloon catheter may further comprise a side aperture for infusing normal saline or medication.

Another aspect of the present disclosure may provide a device for treating or preventing AKI comprising a catheter having a tunnel membrane, at least one seal membrane, at least one wire supporting the membranes, and at least one position indication means, wherein the seal membrane may occlude the orifice of both sides of renal arteries after deployment while also allowing blood flow through the tunnel membrane during application of the device inside the abdominal aorta. In some embodiments, the device may comprise a donut-like (i.e., torus-shaped) balloon to deploy the seal membrane upon inflation. In some embodiments, the donut-like balloon may further comprise a side aperture for infusing normal saline or medication, for example a diuretic. In some embodiments, the seal membrane may not completely occlude the renal arteries while infusion of normal saline dilutes the contrast agent in the blood flowing into renal arteries. In some embodiments, the balloon may be inflated by disturbing the saline infusion pressure when contrast agent passes through the abdominal aorta.

Another aspect of the present disclosure may provide a device for treating or preventing AKI comprising a catheter having a tunnel membrane, at least one wire supporting the tunnel membrane, at least one balloon, and at least one position indication means, wherein the balloon may occlude the orifices of both sides of the renal arteries after deployment while still allowing blood flow through the tunnel membrane during application of the device inside the abdominal aorta. In some embodiments, the balloon may have a donut-like (i.e., torus) shape to occlude the orifices of both sides of renal arteries upon inflation. In some embodiments, the balloon may further comprise a side aperture for infusing normal saline or medication, for example a diuretic. In some embodiments, the balloon may not completely occlude the renal arteries while the normal saline infusion dilutes the contrast agent in the blood flowing into the renal arteries. In some embodiments, the balloon may be inflated by disturbing the saline infusion pressure when contrast agent passes through the abdominal aorta.

Another aspect of the present disclosure may provide a device for treating or preventing AKI comprising a catheter having a tunnel membrane, at least one wire supporting the membrane, at least one infusion tube, and at least one position indication means, wherein the tunnel membrane may disturb blood flow to prevent blood from directly flowing from the supra-renal aorta into the renal arteries during application of the device inside the abdominal aorta of a patient. In some embodiments, the at least one infusion tube may further comprise a side aperture for infusing normal saline or medication, for example a diuretic. In some embodiments, infusion of normal saline may dilute the contrast agent in the blood flowing into renal arteries. In some embodiments, the normal saline infusion may be further increased by disturbing the infusion pressure when contrast agent passes through the abdominal aorta.

Another aspect of the present disclosure may provide a device for treating or preventing AKI comprising a catheter having a tunnel membrane, at least one wire supporting the tunnel membrane, at least one infusion tube, and at least one position indication means, wherein the tunnel membrane may disturb blood flow to prevent blood from directly flowing from the supra-renal aorta into the renal arteries during application of the device inside the abdominal aorta of a patient. In some embodiments, the infusion tube may further comprise a side aperture for infusing normal saline or medication, for example a diuretic. In some embodiments, the normal saline infusion may dilute the contrast agent in the blood flowing into the renal arteries. In some embodiments, the infusion tube may be located at the lower end of the tunnel membrane. In some embodiments, the infusion tube may be located at the top end of the tunnel membrane. In some embodiments, the infusion tube may be located between the lower end and top end of the tunnel membrane. In some embodiments, the infusion tube may be located at the tip or the shaft of the catheter. In some embodiments, the infusion tube may be located at a certain part of the supporting wire. In some embodiments, the normal saline infusion may be further increased by disturbing the infusion pressure when contrast agent passes through the abdominal aorta.

Another aspect of the present disclosure may provide a device for treating or preventing AKI comprising a catheter having a tunnel membrane, at least one wire supporting the tunnel membrane, at least one infusion tube, and at least one position indication means, wherein the tunnel membrane may disturb blood flow to prevent blood from directly flowing from the supra-renal aorta into the renal arteries during application of the device inside the abdominal aorta of a patient. In some embodiments, mediation may be infused near or around the upper end of the tunnel membrane to prevent blood clot formation. In certain embodiments, the medication may be normal saline. In some embodiments, the infusion may be outside of the tunnel membrane. In some embodiments, anticoagulation medication, for example heparin, may be on the surface of tunnel membrane. The heparin may prevent blood clot formation. In some embodiments, the device may be smooth in contour and reduces the risk of blood clot formation.

Another aspect of the present disclosure may provide a device for treating or preventing AKI comprising a catheter having a tunnel membrane, at least one wire supporting the tunnel membrane, a blood flow diversion means in conjunction with the tunnel membrane, at least one infusion tube, and at least one position indication means, wherein the tunnel membrane may disturb blood flow to prevent blood from directly flowing from supra-renal aorta into renal arteries and the blood flow diversion means may further disturb blood flow to make the blood flow from the infra-renal aorta into the renal arteries during application of the device inside the abdominal aorta of the patient. In some embodiments, the blood flow diversion means may be size adjustable. In some embodiments, the blood flow diversion means may be shape adjustable. In some embodiments, the blood flow diversion means may alter blood flow from the infra-renal aorta into the renal arteries by changing size or shape, or by other methods. In some embodiments, the change in size or shape can be controlled with certain timing. In some embodiments, the change in size or shape may be in a fixed or adjustable chronological timing sequence with the injection of contrast agent. In some embodiments, the blood flow diversion means may increase in size inside abdominal aorta and further reduce blood from flowing from the infra-renal aorta into the renal arteries during application of the device inside the abdominal aorta of a patient. In some embodiments, the blood flow diversion means may decrease in size inside the abdominal aorta and further allow the blood to flow from the infra-renal aorta into the renal arteries during application of the device inside the abdominal aorta. In some embodiments, the blood flow diversion means may be a balloon that can inflate or deflate. In some embodiments, the inflation-deflation balloon may be a donut-like balloon on the outside of tunnel membrane. In some embodiments, the inflation-deflation balloon can, when fully inflated, transiently (for example, for five seconds) occupy a part or a whole cross-sectional area between the tunnel membrane and the inner wall of the abdominal aorta. In some embodiments, the inflation-deflation balloon can, when fully inflated, transiently occupy the cross sectional area outside the tunnel membrane and further reduce blood flow from the infra-renal aorta into the renal arteries. In some embodiments, the blood flow diversion means may change its shape to reduce or to allow blood to flow from the infra-renal aorta into the renal arteries. In some embodiments, the blood diversion means may exert its function in the form of an umbrella. In some embodiments, the open or close of the umbrella may be controlled by hinges or flexure joints in conjunction with the tunnel membrane. In some embodiments, the blood flow diversion means may further comprise a side aperture for infusing normal saline or medication. In some embodiments, the infusion tube may further comprise a side aperture for infusing normal saline or medication. In some embodiments, the medication may be diuretic. In some embodiments, the normal saline infusion may dilute the contrast agent in the blood flowing into the renal arteries. In some embodiments, the normal saline infusion may be further increased by disturbing the infusion pressure when contrast agent passes through the abdominal aorta.

Another aspect of the present disclosure may provide a device for treating or preventing AKI comprising a catheter having a tunnel membrane, a sealing portion of the tunnel membrane at the supra-renal aorta in contact with the supra-renal aorta inner wall, at least one wire supporting the tunnel membrane, at least one infusion tube, and at least one position indication means, wherein the tunnel membrane may disturb blood flow to prevent blood from directly flowing from the supra-renal aorta into the renal arteries during application of the device inside the abdominal aorta of a patient. In some embodiments, the sealing portion of the tunnel membrane may be a donut-like circular balloon in contact with the inner wall of the supra-renal aorta. In some embodiments, the balloon may be foldable at initial status. In some embodiments, the sealing portion of the tunnel membrane may be comprised of biocompatible polymer, wherein the sealing portion is expandable circumferentially from a small circle to a large circle. In some embodiments, there may be an internal fluid-filling chamber inside the sealing portion of the tunnel membrane and a filling fluid as a driving force to expand the sealing portion from a small circle to a large circle. In some embodiments, the sealing portion of the tunnel membrane can prevent inadvertent trauma to the abdominal aorta.

Another aspect of the present disclosure may provide a device for synchronized injection of a contrast agent and medications during treatment of prevention of AKI comprising an injector containing a contrast agent chamber and a medications chamber, two outlets for the contrast agent and the medications, respectively, and a common injection actuator operated either by a physician's hand or by a motor. In some embodiments, the medication may be normal saline. In some embodiments, the container may contain both of a contrast agent syringe and a normal saline bag, bottle, or syringe. In some embodiments, the injection actuator may inject contrast agent and normal saline simultaneously. In some embodiments, the proportional amount of injected contrast agent relative to normal saline can be adjusted by adjusting relative diameters or relative dimensions of the syringes to control the flow rate. In some embodiments, the injected medications may be returned to the injection device. In certain embodiments, the injected medications may be released near the entrance of the renal arteries. In some embodiments, the injection outlet of normal saline may be further connected to a volume reservoir bag or volume reservoir balloon and may thereby generate a time difference between actual arrival time of contrast agent and actual arrival time of normal saline inside human body.

Another aspect of the present disclosure may provide a device for balanced fluid flow in and outside a human body comprising a box containing fluids or fluid conduits inflow into and outflow outside of a human body. In some embodiments, the box may contain two chambers in a single container that preserves total volume of the inflow and outflow fluids. In some embodiments, the box may have a fixed total volume, for example having a metal or plastic shell. In some embodiments, there may be a pump for pumping inflow and/or outflow fluids. In some embodiments, there may be pressure transmission fluid between inflow fluid bag and outflow fluid bag, so that the increase of outflow fluid bag pressure may generate compression pressure to drive the inflow of inflow fluid into the human body in the same volume. In some embodiments, there may be fine measures of volume amounts of the inflow and outflow fluids. In some embodiments, the box may have a combined dual cassette that may contain two plastic tube channels (e.g., one normal saline infusion channel and a urine outflow channel). The combined dual cassettes may generate volume-out as volume-in increases, the volume of the volume-out matching the volume of the volume-in. In some embodiments, the flexible urine container (e.g., a bag) and the flexible saline container (e.g., a bag) may be placed in a concealed enclosure, in which the total volume of urine and saline remains constant. In some embodiments, the concealed enclosure may be filled with liquid after urine and saline containers are placed inside. The urine, the saline, and the back-fill liquid in the enclosure may be isolated from on another at all times. During use, an increment of urine may trigger the injection of the same volume of saline/medication. In some embodiments, a pump may be included to introduce energy to the saline injection.

Another aspect of the present disclosure may provide a device for treating or preventing CI-AKI comprising an intra-arterial catheter comprising a tunnel membrane, one or more balloons at each of the proximal and distal ends of the tunnel membrane, at least one infusion tube infusing fluid into or out of the balloons, at least one position indication means, at least one aperture on tunnel membrane, and a wire surrounding the aperture which controls the opening of the aperture, wherein the tunnel membrane may disturb blood flow to prevent blood from directly flowing from the supra-renal aorta into the renal arteries and wherein the aperture on tunnel membrane may further allow or prevent blood flowing from the space inside tunnel membrane to the space outside tunnel membrane. In some embodiments, when infused with fluid the distal balloon may be in contact with the inner wall of the supra-renal aorta. In some embodiments, the proximal balloon, when infused with fluid, may be in contact with the inner wall of the infra-renal aorta. In certain embodiments, the distal and proximal balloons may prevent inadvertent injury to the aorta wall. In certain embodiments, the tunnel membrane may prevent blood from directly flowing from the supra-renal aorta into the renal arteries.

Another aspect of the present disclosure may provide a device for treating or preventing CI-AKI comprising an intra-arterial catheter comprising a tunnel membrane, balloons at proximal and distal ends of tunnel membrane, at least one infusion tube for infusing fluid into or out of the balloons, at least one position indication means, at least one aperture on tunnel membrane, and a wire surrounding the aperture which controls the opening of the aperture, wherein the tunnel membrane may disturb blood flow to prevent blood directly flowing from the supra-renal aorta into the renal arteries and wherein the aperture on the tunnel membrane may further allow or prevent blood flowing from the space inside tunnel membrane to the space outside tunnel membrane. In some embodiments, opening of aperture on the tunnel membrane may be controlled by the wire surrounding the aperture. In some embodiments, the number of aperture and wire sets on the tunnel membrane may be one, two, three, four, five, six, seven, or eight sets. In certain embodiments, the push or pull movement of the wire may change the size of aperture on the tunnel membrane. In some embodiments, the aperture may be closed. In some embodiments, the aperture may be open. In some embodiments, one end of the wire may be attached and fixed, where the other end of the wire may be located outside of the tunnel membrane and be movable and controlled by a physician. In some embodiments, when the wire is pulled the wire may close the aperture such that blood cannot flow through the aperture across the tunnel membrane. In some embodiments, when the wire is not being pulled, the wire may allow opening of the aperture on the tunnel membrane such that blood flow may occur through the aperture across the tunnel membrane. In some embodiments, the pulling movement may be synchronized with the injection of contrast media by the physician.

Another aspect of the present disclosure may provide a device for treating or preventing CI-AKI comprising an intra-arterial catheter comprising a tunnel membrane, balloons at proximal and distal ends of tunnel membrane, at least one infusion tube infusing fluid into or out of the balloons, at least one position indication means, at least one aperture on tunnel membrane, and a wire surrounding the aperture which controls the opening of the aperture, wherein the tunnel membrane may disturb blood flow to prevent blood from directly flowing from the supra-renal aorta into the renal arteries and wherein the aperture on tunnel membrane may further allow or prevent blood flowing from the space inside the tunnel membrane to the space outside the tunnel membrane. In some embodiments, at least one infusion tube may infuse fluid into or out of the balloons. In some embodiments, the infusion tube may infuse fluid into the proximal and distal balloons of the tunnel membrane. In some embodiments, the infusion tube may aspirate fluid out of the proximal and distal balloons of the tunnel membrane. In some embodiments, there may be one, three, five, seven, nine, or eleven infusion tubes. In some embodiments, there may be two, four, six, eight, ten, or twelve infusion tubes. In some embodiments, the infusion tube may be made of plastic material. In some embodiments, the infusion tube may be made of Nitinol with shape-memory function such that opening of the inlet of the tunnel membrane at the distal end is facilitated by the shape-memory Nitinol infusion tube.

Another aspect of the present disclosure may provide a device for treating or preventing CI-AKI comprising a catheter comprising a tunnel membrane, balloons at proximal and distal ends of the tunnel membrane, at least one infusion tube infusing fluid into or out of the balloons, at least one position indication means, at least one aperture on tunnel membrane, and the opening of the aperture controlled by a wire surrounding the aperture, wherein the tunnel membrane may disturb blood flow to prevent blood from directly flowing from the supra-renal aorta into the renal arteries and wherein the aperture on tunnel membrane can further allow or prevent blood flowing from the space inside the tunnel membrane to the space outside the tunnel membrane. In some embodiments, the position indication means may be radio-opaque markers. In some embodiments, the radio-opaque markers may help the physician position the device at proper horizontal level and at proper front-rear level inside the abdominal aorta of a patient.

Another aspect of the present disclosure may provide a device for treating or preventing AKI, for example CI-AKI, comprising an expandable mesh braid having a low-profile configuration for delivery through the vasculature and an expanded configuration for occluding the renal arteries, and a catheter shaft assembly. The catheter shaft assembly may be actuated to deploy an occlusive element, for example the expandable mesh braid, to occlude the renal arteries during injection of contrast media or other harmful substance. The catheter shaft assembly may comprise one or more of an inner shaft, an outer shaft, and a cover. The distal end of the expandable mesh braid may be coupled to the inner shaft while the proximal end of the expandable mesh braid may be coupled to the outer shaft such that translation of the inner shaft relative to the outer shaft deploys or collapses the expandable mesh braid. The device may further comprise a time-delayed release mechanism configured to automatically collapse the expandable mesh braid after a pre-determined amount of time following deployment.

Another aspect of the present disclosure may provide a device for treating or preventing acute kidney injury, comprising a catheter having a plurality of balloons, when inflated, can occlude partially or completely aortic branching arteries, through which aorta blood flows into right and left kidneys. In some embodiments, the acute kidney injury may be contrast induced nephropathy or contrast-induced acute kidney injury. In some embodiments, the balloons may be located inside the abdominal aorta. In some embodiments, the balloons can be inflated or deflated. In some embodiments, the balloons can be inflated by fluid or gas. In some embodiments, the balloons can be inflated or deflated partially or completely. In some embodiments, the balloons, when inflated, can divert aorta blood flow from directly flowing into renal arteries. In some embodiments, the balloons, when inflated, can occlude partially or completely aortic branching arteries, through which aorta blood flows into right and left kidneys. In some embodiments, the aortic branching arteries may include right and left renal arteries. In some embodiments, the balloons may contact with inner wall of the abdominal aorta. In some embodiments, the contact of the balloons with inner wall of the abdominal aorta may not cause damage to the inner wall of the abdominal aorta. In some embodiments, the balloons may not cause blood clot formation. In some embodiments, there may be radio-opaque markers near proximal and distal ends of the balloons on the catheter to guide proper vertical location of the catheter under fluoroscopy. In some embodiments, there may be radio-opaque markers on the balloon membrane to guide proper rotational orientation and proper inflation of the balloons inside the abdominal aorta. In some embodiments, the proper rotational orientation can be guided by overlapping of front and rear radio-opaque linear markers under fluoroscopy. In some embodiments, the proper inflation can be guided by flattening of lateral radio-opaque curve markers under fluoroscopy. In some embodiments, the inflation of balloons can be synchronized in chronological sequence with the injection of contrast media by a physician during a cardiac catheterization procedure. In some embodiments, the inflation of balloons may be maintained for a certain period of time, for example five seconds, to allow aorta blood with high concentrated contrast media flowing from supra-renal aorta to infra-renal aorta, without directly flowing into renal arteries. In some embodiments, the endovascular catheter may have a central conduit. In some embodiments, the central conduit can allow a guidewire passing through. In some embodiments, the central conduit can allow a coronary catheter passing through. In some embodiments, the endovascular catheter may be a variant of introducer and can be used as an introducer sheath. In some embodiments, the endovascular catheter may be used as a standalone device. For example, a different catheter may be introduced into the patient via a trans-femoral or trans-radial route, the renal ostia shielding catheter may be inserted via a different trans-femoral route. Inside the abdominal aorta, the shielding catheter may be advanced to be substantially parallel with the different catheter, without interfering with its function even when the occlude element(s) of the shielding catheter are deployed.

Aspects of the present disclosure may provide a device for preventing acute kidney injury from contrast agent introduced into vasculature of a subject. The device may comprise a catheter shaft comprising proximal portion and a distal portion, an occlusive element disposed on the proximal portion, and one or more position indication feature disposed on one or more of the catheter shaft or the occlusive element. The occlusive element may have an expanded configuration in which, when advanced into an abdominal aorta and positioned adjacent renal artery ostia of the subject, is sized to occlude the renal artery ostia while allowing blood flow over the catheter shaft. The distal portion may be configured to remain outside a body of the subject when the proximal portion is positioned adjacent renal artery ostia of the subject.

The occlusive element may comprise a first expandable member disposed on a first lateral side of the proximal portion and a second expandable member disposed on a second lateral side of the proximal portion. The first and second expandable members may have an expanded configuration in which, when advanced into an abdominal aorta and positioned adjacent renal artery ostia of the subject, are sized to occlude the renal artery ostia while allowing blood flow over the catheter shaft. The first expandable member and the second expandable member may be in fluid communication with one another. For example, the first expandable member and the second expandable member may comprise a single balloon, and the single balloon may be configured to assume a predetermined, desired shape when expanded. Alternatively, the first expandable member and the second expandable member may be fluidly independent of one another. For example, the first expandable member comprises a first balloon and the second expandable member comprises a second balloon, and the first and second balloons may be configured to assume predetermined, desired shapes when expanded. The expanded configuration of the occlusive element may be spherical, ellipsoidal, cylindrical, an n-sided prism, conical, pyramidal, butterfly-shaped, dumbbell-shaped, cigar-shaped, torpedo-shaped, or submarine-shaped.

The one or more position indication features may be disposed on the proximal portion of the catheter shaft adjacent the occlusive element. Alternatively or in combination, the one or more position indication features may be disposed on the occlusive element. The position indication feature(s) may comprise one or more radio-opaque markers. The radio-opaque marker(s) comprises one or more radio-opaque longitudinal marker. The radio-opaque longitudinal marker(s) may comprise a plurality of radio-opaque longitudinal markers disposed on the occlusive element along a longitudinal axis of the occlusive element.

The device may further comprise an orientation element disposed on the distal portion of the catheter shaft. The orientation element may be aligned with the occlusive element and configured to indicate the orientation of the occlusive element when positioned adjacent renal artery ostia of the subject. The orientation element may comprise one or more of a visible marking, a protrusion, a wing, or a flag, for example.

Aspects of the present disclosure may provide a system for preventing acute kidney injury from contrast agent introduced into vasculature of a subject. The device may comprise a catheter shaft comprising proximal portion and a distal portion, an occlusive element disposed on the proximal portion, and a time-delayed release mechanism in communication with the occlusive element. The occlusive element may have an expanded configuration in which, when advanced into an abdominal aorta and positioned adjacent renal artery ostia of the subject, is sized to occlude the renal artery ostia while allowing blood flow over the catheter shaft. The distal portion may be configured to remain outside a body of the subject when the proximal portion is positioned adjacent renal artery ostia of the subject. The time-delayed release mechanism may be configured to collapse the occlusive element after a pre-determined amount of time following expansion of the occlusive element.

The time-delayed release mechanism may comprise an energy accumulation and storage component. The energy accumulation and storage component may comprise a spring. The energy accumulation and storage component may comprise a syringe comprising a plunger, and the spring may be coupled to the plunger.

The one or more position indication features may be disposed on one or more of the catheter shaft or the occlusive element. The position indication feature(s) may be disposed on the proximal portion of the catheter shaft adjacent the occlusive element. The position indication feature(s) may be disposed on the occlusive element. The position indication feature(s) may comprise one or more radio-opaque marker. The radio-opaque marker(s) may comprise one or more radio-opaque longitudinal marker. The radio-opaque longitudinal marker(s) may comprise a plurality of radio-opaque longitudinal markers disposed on the occlusive element along a longitudinal axis of the occlusive element.

The occlusive element may comprise a mesh braid. The occlusive element may comprise an expandable member. The expandable member may comprise an inflatable balloon. The occlusive element may comprise a first expandable member disposed on a first lateral side of the proximal portion and a second expandable member disposed on a second lateral side of the proximal portion. The first and second expandable members may have an expanded configuration in which when advanced into an abdominal aorta and positioned adjacent renal artery ostia of the subject are sized to occlude the renal artery ostia while allowing blood flow over the catheter shaft. The first expandable member and the second expandable member may be in fluid communication with one another. Alternatively, the first expandable member and the second expandable member may be fluidly independent of one another. The expanded configuration of the occlusive element may be spherical, ellipsoidal, cylindrical, an n-sided prism, conical, pyramidal, butterfly-shaped, dumbbell-shaped, cigar-shaped, torpedo-shaped, or submarine-shaped.

The system may further comprise an orientation element disposed on the distal portion of the catheter shaft. The orientation element may be aligned with the occlusive element and configured to indicate the orientation of the occlusive element when positioned adjacent renal artery ostia of the subject. The orientation element may comprise one or more of a visible marking, a protrusion, a wing, or a flag, for example.

Aspects of the present disclosure may provide a method of preventing acute kidney injury from contrast agent introduced into vasculature of a subject. A proximal portion of a catheter device comprising a catheter shaft and an occlusive element may be positioned in an abdominal aorta of the subject adjacent renal artery ostia of the subject. One or more position indication feature disposed on one or more of the catheter shaft or the occlusive element may be observed to verify a correct placement and/or orientation of the catheter shaft and the occlusive element. The occlusive element of the catheter device may be deployed to occlude the renal artery ostia. A bolus of the contrast agent may then be introduced into the abdominal aorta of the subject while the occlusive element is deployed to occlude the renal artery ostia, thereby preventing the contrast agent from entering into renal arteries of the subject. The occlusive element may be collapsed after the bolus of the contrast agent has been introduced, thereby allowing blood flow to the renal arteries to resume.

In positioning the proximal portion of the catheter device, a position of the one or more position indication features may be observed and the proximal portion of the catheter device may be positioned in response to the observed position. The indication feature(s) may comprise a radio-opaque marker, and the position indication feature(s) may be observed using x-ray imaging.

The occlusion of the renal artery ostia may be confirmed when the occlusive element is deployed. For instance, the position indication feature(s) may comprise one or more radio-opaque longitudinal markers, and confirming occlusion of the renal artery ostia may be confirmed by observing the appearance of a bowed section in the one or more radio-opaque longitudinal markers using x-ray imaging. When the occlusive element is deployed, a portion of the occlusive element may bow into the renal artery ostia and the radio-opaque longitudinal markers may bow to allow this bowing to be observed.

In positioning the proximal portion of the catheter device, an orientation of an orientation element disposed on a distal portion of the catheter device may be observed and the proximal portion of the catheter device may be positioned in response to the observed orientation. The orientation element may be aligned with the occlusive element and configured to indicate the orientation of the occlusive element when positioned adjacent renal artery ostia of the subject.

The occlusive element may comprise an expandable mesh braid, and the occlusive element may be deployed by expanding the expandable mesh braid and collapsed by collapsing the expandable mesh braid.

The occlusive element may comprise an expandable member, and the occlusive element may be expanded by expanding the expandable member and collapsed by collapsing the expandable member.

The expandable member may comprise an inflatable balloon, and the expandable member may be expanded by inflating the balloon and collapsed by deflating the balloon.

The occlusive element may comprise a first expandable member disposed on a first lateral side of the proximal portion and a second expandable member disposed on a second lateral side of the proximal portion, wherein deploying the occlusive element comprises expanding the first and second expandable members, and wherein collapsing the occlusive element comprises collapsing the first and second expandable members.

The first and second expandable members may be expanded independently of one another. Alternatively, the first and second expandable members may be simultaneously expanded.

The occlusive element may be collapsed after a pre-determined amount of time. The deployment of the occlusive element and introduction of the bolus of the contrast agent may be synchronized.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present disclosure will be obtained by reference to the following detailed description that sets forth illustrative embodiments, in which the principles of the invention are utilized, and the accompanying drawings (also "Figure" and "FIG." herein), of which:

FIG. 3A shows a cylinder-like inflated balloon. FIG. 3B shows a cross-section view of the cylinder-like inflated balloon of FIG. 3A. FIG. 3C shows the morphology of an exemplary inflated first balloon which is "butterfly-like". FIG. 3D shows a cross-section view of the butterfly-like inflated balloon of FIG. 3C.

FIGS. 14A-14B illustrate yet another embodiment of the present disclosure wherein the device comprises a first balloon inflated to a pre-determined size and a second balloon around the first balloon. An acoustic wave may be generated by the second balloon.

FIG. 16A shows an embodiment wherein the disturbing means is a tunnel membrane. FIG. 16B shows a cross-sectional top-down view of the embodiment of FIG. 16A. FIG. 16C shows an embodiment with an umbrella-like device used as an anchor to facilitate deployment of the tunnel membrane. FIG. 16D shows an embodiment with a smaller second balloon used as an anchor to facilitate deployment of the tunnel membrane.

FIG. 17A shows a cross-sectional side-view of an exemplary wire device. FIG. 17B shows the specification of the embodiment of FIG. 17A in the aorta. FIG. 17C shows the application of normal saline or other suitable medicines via at least one injection hole.

FIGS. 18A-18D illustrate another embodiment of a disturbing means comprising a cone-shaped wire device partially covered with the tunnel membrane. FIG. 18A shows a cross-sectional side-view of the embodiment. FIG. 18B shows a top view of the embodiment. FIG. 18C shows a bottom view of the embodiment. FIG. 18D provides an isometric view of the embodiment.

FIG. 19A shows the device with the tunnel membrane at the beginning of deployment from the catheter. FIG. 19B shows the tunnel membrane partially deployed into the abdominal aorta. FIG. 19C shows the tunnel membrane fully deployed into the abdominal aorta.

FIG. 20A shows a device comprising a catheter with a tunnel membrane, a seal membrane, multiple supporting wires, and one donut-like balloon. FIG. 20B shows the device with the donut-like balloon in its deflated state. FIG. 20A shows the device with the donut-like balloon in its inflated state. FIG. 20D shows the device positioned inside the abdominal aorta with the balloon inflated to deploy the seal membrane and occlude the orifices of both sides of the renal arteries.

FIG. 21A shows the embodiment with the donut-like balloon in its deflated state. FIG. 21B shows the embodiment with the donut-like balloon in its inflated state. FIG. 21C shows the embodiment positioned inside abdominal aorta with the balloon inflated to occlude the orifices of both sides of the renal arteries.

FIG. 22A shows an embodiment comprising a catheter having a tunnel membrane, multiple supporting wires, one infusion tube at the lower end of the tunnel membrane, and one infusion tube attached to the tunnel membrane. FIG. 22B shows the embodiment of FIG. 22A positioned inside the abdominal aorta.

FIG. 24A shows a synchronized injector of contrast agent and medication which allows for adjustment of the relative amount and relative time to arrival inside human body of the two fluids. FIG. 24B shows how the device may enable chronological and volumetric differences between the two fluids.

FIGS. 26A-26C show yet another embodiment of the present disclosure. FIG. 26A shows a catheter shaft comprising an outer shaft, an inner shaft disposed therein. FIG. 26B shows the catheter shaft device with expandable mesh braid coupled to the inner and outer shafts in a low-profile configuration. FIG. 26C shows the catheter shaft device with expandable mesh braid in an expanded configuration.

FIG. 26D shows a prototype of a catheter shaft device with expandable mesh braid. FIG. 26E shows a fully open mesh braid. FIG. 26F shows a partially collapsed mesh braid. FIG. 26G shows a fully collapsed mesh braid.

FIG. 27A shows the insertion of the embodiment into the abdominal aorta. FIG. 27B shows the positioning of the device in the abdominal aorta. FIG. 27C shows the device deployed. FIG. 27D shows the device collapsed.

FIG. 28A shows a prototype of a balloon catheter device having two ellipsoidal balloons, one balloon for occluding each of the left and right renal arteries, in a collapsed configuration. FIG. 28B shows the prototype in an expanded configuration. FIG. 28C shows the prototype in the expanded configuration inside a model abdominal aorta.

FIGS. 29A-29D show an embodiment of a position indication feature which can be used to determine if a balloon catheter device occludes the renal arteries. FIGS. 29A and 29B shows an axial view along the abdominal aorta depicting the relative positions of the left and right balloons in the initial position (FIG. 29A) and the "protective" or expanded position (FIG. 29B). FIGS. 29C and 29D show the position indication feature in the initial position (FIG. 29C) and the "protected" or expanded position (FIG. 29D).

DETAILED DESCRIPTION

Figure 1:
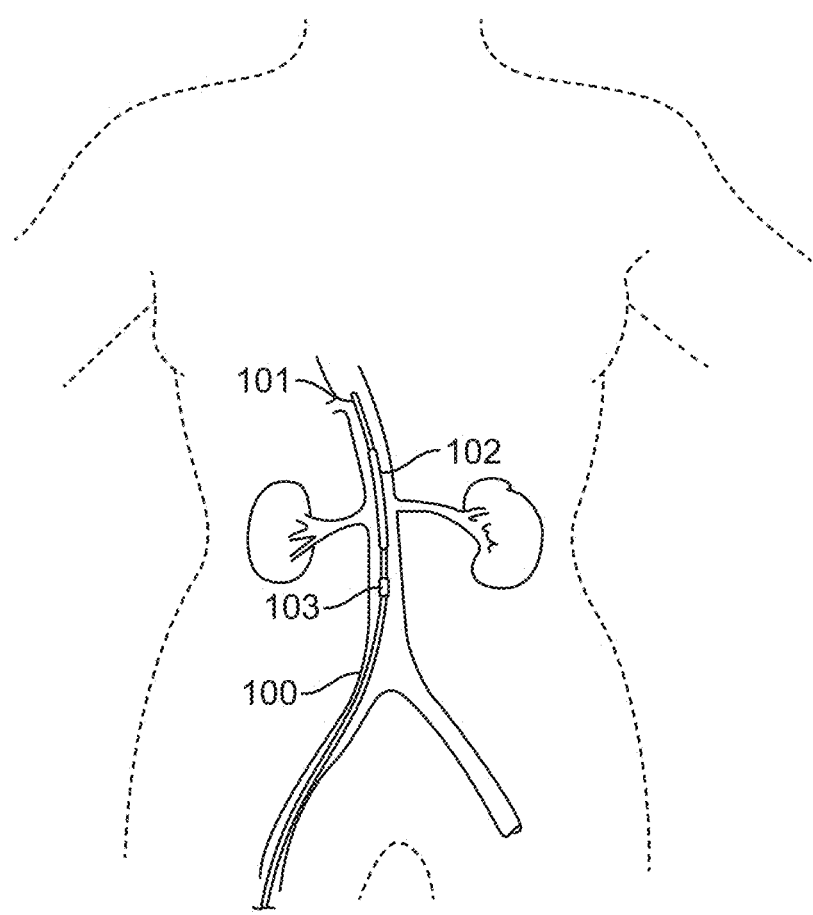
FIG. 1 illustrates an embodiment of a device comprising a balloon catheter having a first balloon positioned in the supra-renal aorta near the orifices of the bilateral renal arteries for treating AKI.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Provided herein are devices and systems that specifically focus on solving one or both of the two main pathophysiological culprits of CI-AKI—prolonged transit of contrast media inside the kidneys and renal outer medulla ischemia. In some embodiments, devices, systems, and methods are provided for reducing contrast media concentrations or amounts entering the renal arteries to prevent AKI, for example CI-AKI. Alternatively or in combination, some embodiments provide devices, systems, and methods for augmenting blood flow towards the renal arteries that feed the kidneys to treat or prevent renal ischemia.

In some embodiments, a device for treating AKI, for example CI-AKI, may comprise a balloon catheter having at least a first balloon, at least one sensor associated with the first balloon, and at least one position indication means. The balloon catheter device may additionally comprise a second balloon. The first balloon may, for example, be placed inside the abdominal aorta of a patient so as to occlude the orifices of both sides of the renal arteries after inflation. Blood may continue to flow through the inflated balloon during application of the device inside the abdominal aorta. The position indication means may for example be a radio-opaque marker, or other detectable marker, in order to improve visibility of the device during deployment for example with fluoroscopy or radiography.

Alternatively or in combination, the balloon catheter device may comprise a first balloon, a second balloon, and at least one sensor associated with one of the first or second balloons. The sensor may for example be a pressure sensor or a size-measuring sensor. Further, the device may comprise a plurality of sensors on one or more of the first or second balloons. The plurality of sensors may for example comprise one or more of a pressure sensor, one or more of a size-measuring sensor, or any combination thereof.

Some embodiments of the balloon catheter device may alternatively or in combination comprise at least one side aperture on the catheter to allow for application of normal saline or other medications. The normal saline or other medications may be infused from a control box through the catheter into the supra-renal aorta. In some embodiments, the normal saline or other medications may be applied for example via a side aperture between the first and second balloons. Alternatively or in combination, the normal saline or other medications may be applied for example via the tip of the catheter.

Alternatively or in combination, the balloon catheter device may comprise at least one guidewire and at least one spinning propeller. The spinning propeller may for example spin around the central guidewire in order to generate augmented renal artery blood flow toward a first kidney. The spinning propeller may for example be wing-shaped or fin-shaped. The balloon catheter device may further comprise an additional guidewire and an additional spinning propeller. The additional guidewire and additional spinning propeller may be operated so as to generate augmented renal artery blood flow towards a second kidney. Operation of the spinning propeller may be functionally independent or simultaneous with operation of the balloon catheter in order to generate directional augmented flow toward one or both of the kidneys. Alternatively or in combination, blood flow towards the renal arteries may be increased using an acoustic wave pump or a micro-electro-mechanical (MEM) micropump.

Alternatively or in combination, the balloon catheter device may comprise a flow disturbing means associated with the first balloon. For example, the flow disturbing means may be a tunnel membrane attached to the first balloon and adapted to fit inside the aorta wall. The flow disturbing means may alternatively be an umbrella-like blood flow reducing component that may be attached to either the catheter or the first balloon and positioned either in the supra-renal aorta above the renal arteries or in the infra-renal aorta below the renal arteries.

The flow disturbing means may for example be a cone-shaped wire device that is partially covered with a tunnel membrane. The device may be deployed from the catheter. The cone-shaped wire device may comprise a plurality of wires, for example at least 3 wires. In some embodiments, the cone-shaped wire device may comprise any number of wires suitable to provide a disturbing means. The wires may for example be made of any superelastic or pseudoeleastic material, for example nitinol. The cone-shaped wire device may further comprise an upper cylinder portion used to form a tight contact between the device and the aorta wall.

The flow disturbing means may alternatively be any similar shape, structure, or function as an umbrella-like blood flow reducing component. The flow disturbing means may be any device that can disturb blood flow such that there may be lower blood intake by the renal arteries from the infra-renal aorta. The flow disturbing means may further comprise one or more injection hole through which normal saline or other medications may be injected, for example to dilute a contrast agent in the blood prior to being taken up by the renal arteries towards the kidneys. In some embodiments, the injection hole may be on the catheter, for example, close to the catheter tip from which the disturbing means may be deployed.

In some embodiments, a device for treating or preventing AKI, for example CI-AKI, may comprise a catheter, a tunnel membrane, at least one supporting wire, at least one flow disturbing means, and at least one position indication means. When deployed in the abdominal aorta, the flow disturbing means may dilute a contrast agent flowing into the renal arteries while allowing for blood to flow through the tunnel membrane. The device may comprise a plurality of supporting wires. Alternatively or in combination, the device may comprise an infusion tube.

Alternatively or in combination, the device may further comprise a flow diversion means in conjunction with the tunnel membrane. The flow diversion means may be deployed inside the abdominal aorta such that the orifices of both sides of the renal arteries are occluded by the flow diversion means and such that blood is allowed to flow through the tunnel membrane. The position indication means may for example be a radio-opaque marker, or other detectable marker, in order to improve visibility of the device during deployment for example with fluoroscopy or radiography.

Alternatively or in combination, the device may further comprise at least one balloon at the proximal end of the tunnel membrane, at least one balloon at the distal end of the tunnel membrane, at least one infusion tube, at least one aperture on the tunnel membrane, and a wire surrounding the aperture which controls the opening of the aperture. The infusion tube may be used to infuse a fluid into or out of the balloons. The device may comprise at least two infusion tubes. The device may comprise a plurality of apertures and wires controlling the apertures. The tunnel membrane may disturb blood flow to prevent blood from flowing into the renal arteries directly from the supra-renal aorta, instead shunting the blood through the tunnel membrane into the infra-renal aorta. The aperture on the tunnel membrane may further allow or prevent blood to flow from the space inside the tunnel membrane to the space outside the tunnel membrane. Shunting on the tunnel membrane may be synchronized with injection of a contrast media by the physician.

Alternatively, the device may comprise a catheter shaft assembly actuated to deploy an occlusive element to occlude the renal arteries during injection of contrast media or other harmful substance. The catheter shaft assembly may comprise one or more of an inner shaft, an outer shaft, and a cover. The inner shaft may be disposed within the outer shaft and translatable relative to each other. The occlusive element may for example be an expandable mesh braid which may comprise a plurality of filaments. When expanded, the expandable mesh braid may contact the inner walls of the abdominal aorta and cover the renal artery ostia. The expanded mesh braid may have a filament density sufficient to occlude blood flow into or divert blood flow away from the renal ostia. In some embodiments, the expandable mesh braid may be radially expanded and axially compressed to increase the filament density at the axially central region of the expanded mesh braid which covers the renal ostia. The distal end of the expandable mesh braid may be coupled to the inner shaft. The proximal end of the expandable mesh braid may be coupled to the outer shaft such that translation of the inner shaft relative to the outer shaft deploys or collapses the expandable mesh braid. The device may further comprise a time-delayed release mechanism configured to automatically collapse the expandable mesh braid after a pre-determined amount of time following deployment. The time-delayed release mechanism may be provided on a handle or controller of the device.

In many embodiments, the device may comprise an occlusive element. The occlusive element may comprise any of the balloons, membranes, or expandable elements (e.g. mesh braid) described herein. The occlusive element may be disposed on or around a proximal portion of a catheter. The occlusive element may be advanced into an abdominal aorta and positioned adjacent renal ostia in a collapsed configuration. The occlusive element may then be expanded (e.g. inflated) into an expanded configuration which is sized to partially or fully occlude or divert blood flow from the renal artery ostia while allowing blood flow over the catheter shaft. It will be understood by one of ordinary skill in the art that any of the occlusive elements (e.g. balloons, membranes, braids, etc.) described herein or any of the features thereof may be combined as desired in order to arrive at a device for treating or preventing AKI. Any of the occlusive elements, or any combination thereof, may be combined with any of the position indication means or features, flow disturbing means or elements, flow pumps, sensors, flow augmentation means or elements, injection synchronizer, fluid balancer, time-delayed release mechanism, any other element described herein, or any combination thereof, as desired by one of ordinary skill in the art, to arrive at a device for treating or preventing AKI.

FIG. 1 shows an exemplary embodiment of a device for treating or preventing AKI, for example CI-AKI, comprising a balloon catheter device. The device 100 may comprise a catheter 101, a first balloon 102, a second balloon 103, and a position indication means, for example a radio-opaque marker, on the tip of the catheter 101. The device 100 may be inserted into the abdominal aorta of a patient and positioned by monitoring the position of the radio-opaque marker for guidance. The device 100 may be inserted into the abdominal aorta using either a trans-femoral arterial approach, a trans-brachial artery approach, or a trans-radial artery approach. The tip of the catheter 101, which may include a radio-opaque marker, may be situated so as to position the first balloon in the supra-renal aorta such that the first balloon lies near the orifices of the bilateral renal arteries.

Figure 2:
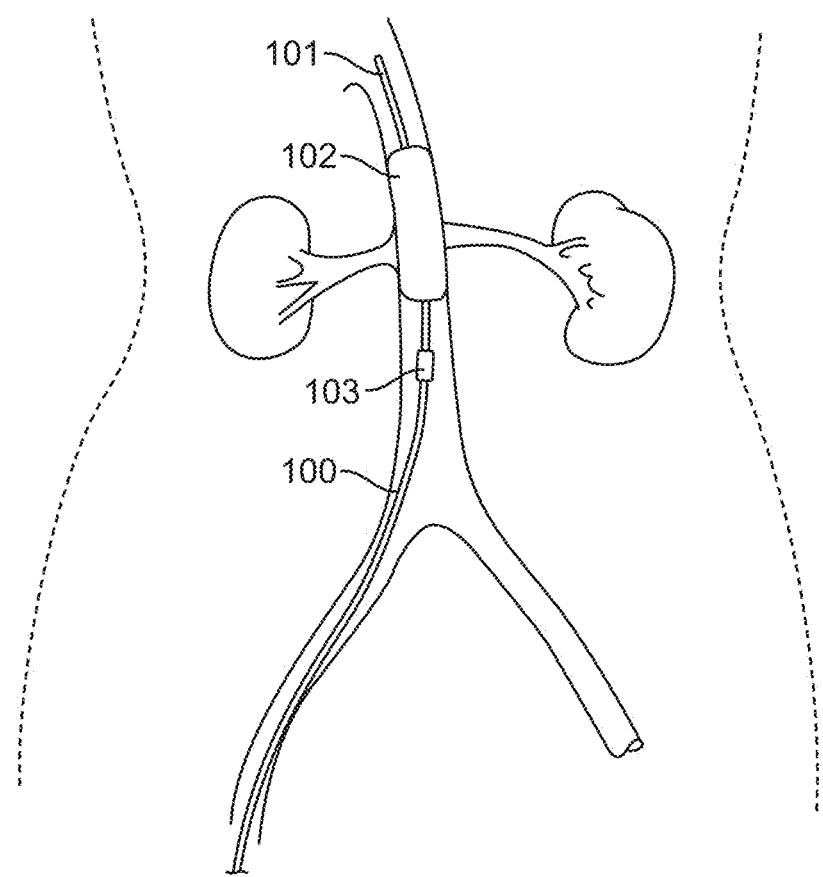
FIG. 2 shows the embodiment illustrated in FIG. 1, wherein the first balloon is inflated to occlude the orifices of both sides of the renal arteries.

FIG. 2 shows the device 100 positioned in the supra-renal aorta near the orifices of the bilateral renal arteries. The first balloon 102 is inflated such that the balloon 102 occludes the orifices of both sides of the renal arteries. The second balloon 103 remains un-inflated. Occlusion of the renal arteries by the first balloon 102 may prevent a bolus influx of harmful agents, for example a contrast media, from flowing into the renal arteries from the supra-renal aorta. Such occlusion may reduce the toxic effects of said harmful agents by preventing delivery of the harmful agents to the kidney. The bolus of contrast media may be introduced using the same device 100 or a separate device that has been introduced either through the same or different path in the vasculature.

Figure 3A:
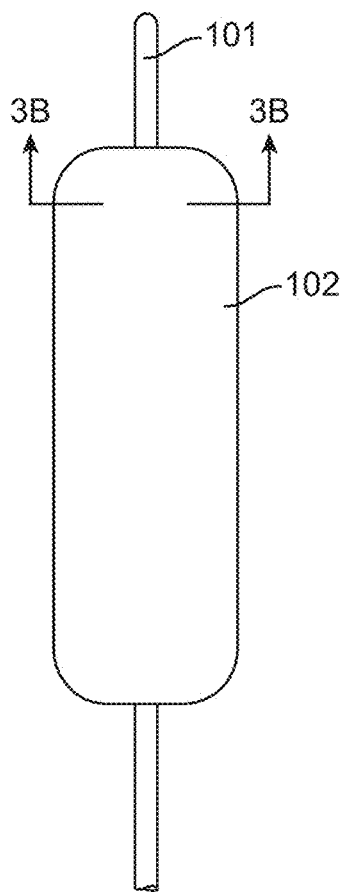
FIGS. 3A-3D are perspective views of the first balloon of the embodiment of FIG. 1.
Figure 3B:
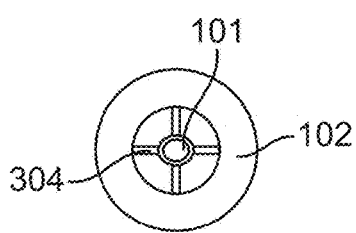
Figure 3C:
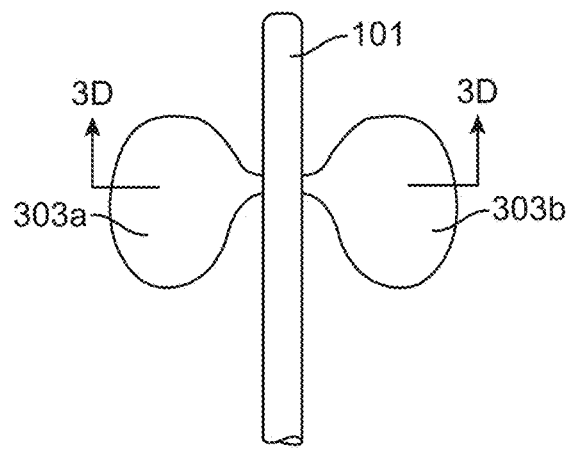
Figure 3D:
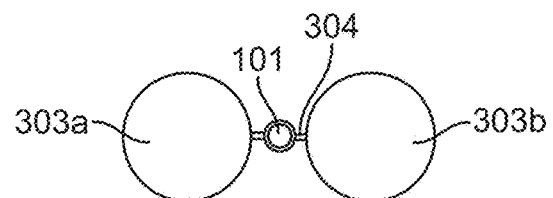

FIGS. 3A to 3D illustrate various embodiments of the first balloon 102. FIG. 3A shows an inflated first balloon 102 positioned along and circulating the catheter 101. FIG. 3B shows a cross-sectional view of the first balloon 102 of FIG. 3A. The balloon may be positioned around the catheter 101 such that a hollow area is formed between the inner edge of the balloon 102 and the catheter 101 to form a donut-like balloon shape. By providing a hollow space inside of the balloon 102, blood may be allowed to flow along the catheter 101 when the balloon 102 is inflated to occlude the orifices of both sides of the renal arteries. The first balloon 102 may be inflated via at least one connection tube 304 extending from the catheter 101 to the balloon 102. For example, the balloon may be inflated via four connection tubes 304 as shown in FIG. 3B. FIG. 3C shows an alternative embodiment of the first balloon 102. The first balloon 102 may be comprised of bilateral inflated balloon sections 303a and 303b to form a butterfly-like balloon shape. The sections 303a and 303b may be connected to each side of catheter 101 via at least one connection tube 304. Inflation of the balloon sections 303a and 303b may occlude the orifices of both sides of the renal arteries while also allowing blood to flow along the catheter 101. FIG. 3D shows a cross-sectional view of the butterfly-like embodiment of the first balloon 102 depicted in FIG. 3C. The balloon sections 303a and 303b may be connected to the catheter 101 via one or more connection tube 304. For example, FIG. 3D depicts one connection tube per balloon section on each side of the catheter 101. In some embodiments, the balloon may have one, two, three, four, or five connection tubes 304 to connect the first balloon 102 to the catheter 101. The connection tube(s) may be used to provide inflation or deflation of the first balloon 102.

In some embodiments, the first balloon 102 may be donut-like after inflation. In some embodiments, the first balloon 102 may have a butterfly-like shape after inflation.

Figure 4:
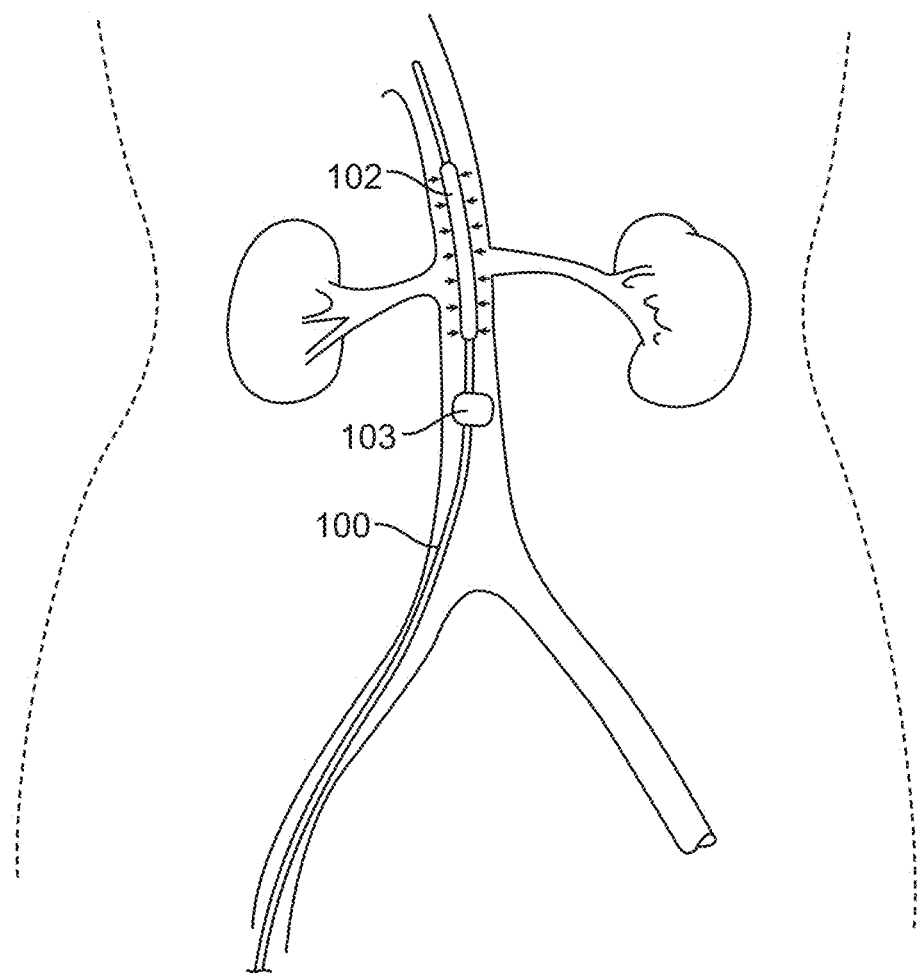
FIG. 4 shows an embodiment with a deflated first balloon and an inflated second balloon at the location of the infrarenal aorta near the orifices of the renal arteries.

FIG. 4 shows the device 100 with a deflated first balloon 102 and inflated second balloon 103. The first balloon 102 may be deflated (indicated by arrows) and the second balloon 103 may be inflated after contrast media-containing blood has passed beyond the orifices of the renal arteries. The second balloon 103 may be positioned in the infra-renal aorta near the orifices of the renal arteries. The second balloon 103 may be inflated to an extent such that is does not completely occlude aortic blood flow.

Figure 5:
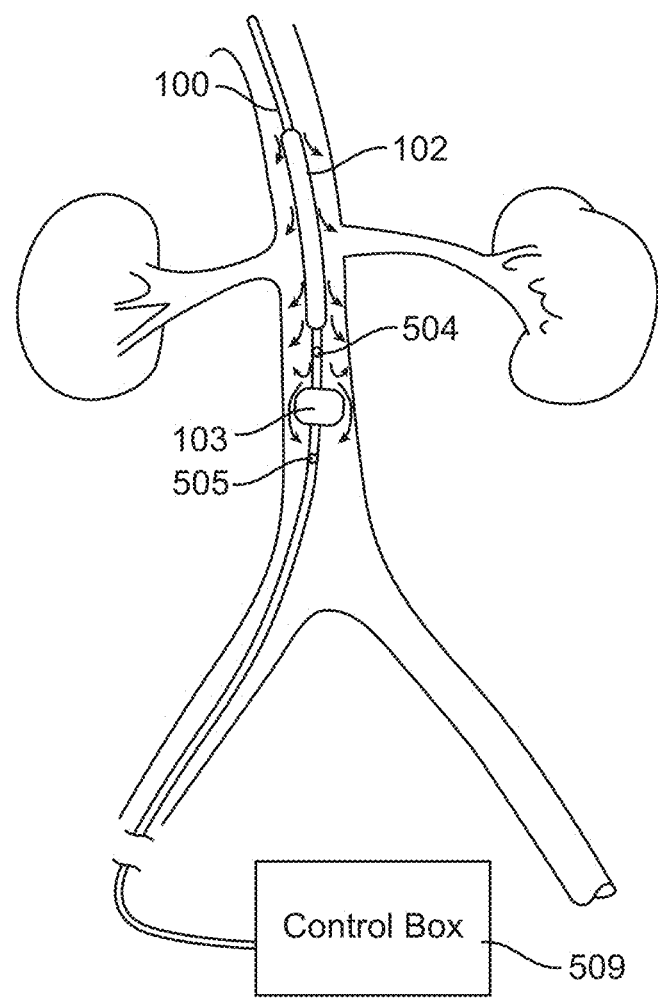
FIG. 5 shows the vortex blood flow caused by distension of the second balloon.

As shown in FIG. 5, distension of the inflated second balloon 103 may generate a vortex-like pattern of blood flow. Vortex flow may facilitate or augment renal artery blood flow. In some embodiments, there may be at least one sensor (for example 504 or 505) associated with the first balloon 102 or second balloon 103 for the control of inflation and/or deflation of either the first or second balloon. In some embodiments, the sensor may be a pressure sensor to detect balloon inflation. In some embodiments, the sensor may be a size-measuring sensor to detect the relative size of either the first balloon or the second balloon. A non-limiting example in shown in FIG. 5 where there is a first pressure sensor 504 at the lower side of the first balloon or at the upper side of the second balloon. A second pressure sensor 505 is at the lower side of the second balloon. Sensors 504 and 505 may alternatively or in combination be one or more of a size-measuring sensor. Sensors 504 and 505 may be associated with either one of the first balloon 102 or second balloon 103.

Analysis of data generated by the pressure sensors can be used for instantaneous titration of the degree of distension of the second balloon 103 in order to provide an adequate pressure gradient to generate vortex blood flow into the renal arteries. Additionally, the altered aortic blood flow may increase the renal artery blood flow due to the local proximity and diameter of the distended second balloon 103. In some embodiments, the diameter of the distended second balloon 103 may be adjustable such that the diameter of the distended balloon 103 does not fully obstruct blood flow in the aorta. By only partially obstructing blood flow, an inadequacy of aortic blood flow at the distal aorta or at branches of the aorta, for example the right and left common iliac arteries, may be prevented. Furthermore, the wall of the aorta may be preserved from injury by the balloon distension.

The device 100 may further comprise a control box 509 placed outside of the patient. The control box may be in connection with the balloon catheter and may serve several functions including any of the following: inflation of the first and second balloons, deflation of the first and second balloons, pressure sensing, measurement of one or more upper and lower pressure sensors, titration of normal saline via an included infusion pump with titrateable infusion rate, or any combination thereof.

Some embodiments of the device 100 may have two sets of pressure sensors (e.g. 504, 505). For example, one set of sensors may be located at the supra-renal aorta side of the first 102 or second balloon 103 and the second set of sensors may be located at the infra-renal aorta side of the first 102 or second balloon 103. The two sets of sensors may continuously measure pressure and report pressure data back to the control box 509. The pressure difference between the two sensors may be displayed by the control box 509. A physician may then read the pressure difference and adjust the size of first or second balloon or both using of control box 509. Alternatively or in combination, the control box 509 may automatically adjust the size of the first or second balloon or both in response to measured pressure differences.

Figure 6:
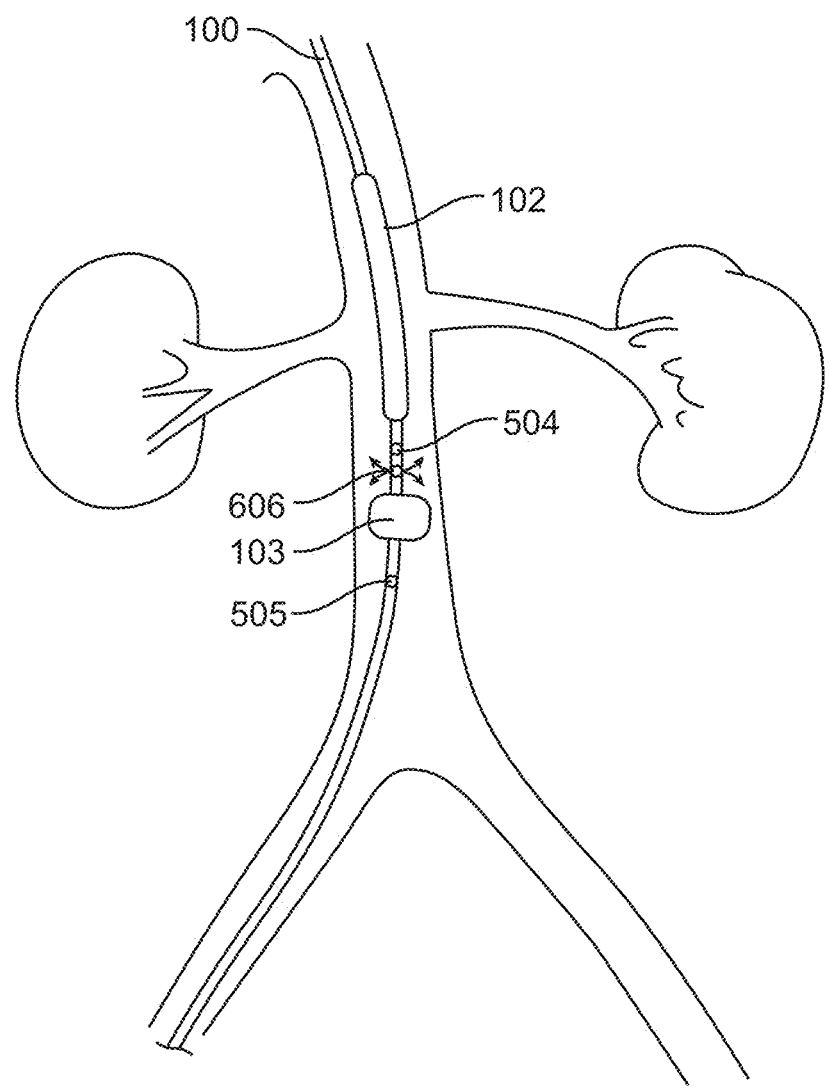
FIG. 6 shows infusion of normal saline from a control box, through a catheter pore, and into the abdominal aorta while the second balloon remains inflated.

FIG. 6 shows an alternative embodiment of the device 100. The device 100 may further comprise a side aperture 606 on the balloon catheter 101 to facilitate application of normal saline or other medications into the blood. Infusion of the normal saline into the supra-renal aorta may further augment renal artery blood flow. Furthermore, infusion of normal saline directly into the supra-renal aorta may avoid a fluid overload burden on the heart, which may be of particular importance when patients suffer from congestive heart failure. Alternatively or in combination, infusion of normal saline into the supra-renal aorta may help treat CI-AKI by diluting the concentration of contrast media in the supra-renal aorta and reducing the potential for adverse effects caused by contrast media-induced blood hyperviscosity in the kidneys.

The normal saline or other medications may be infused from the control box 509 through the catheter 101 into the supra-renal aorta. In some embodiments, the infusion rate of the normal saline or medications through the side aperture 606 into aorta may be controlled by the control box 509. In some embodiments, there may be a control pump inside the control box 509. In some embodiments, the control pump may be a separate unit. The medication may a vasodilatory agent, for example Fenoldopam or the like. The medication may be infused via the side aperture 606 for prevention and/or treatment of CI-AKI.

In some embodiments, the side aperture 606 may be located between the first balloon 102 and second balloon 103. In some embodiments the side aperture 606 may be located at the tip of the catheter 101.

Figure 7:
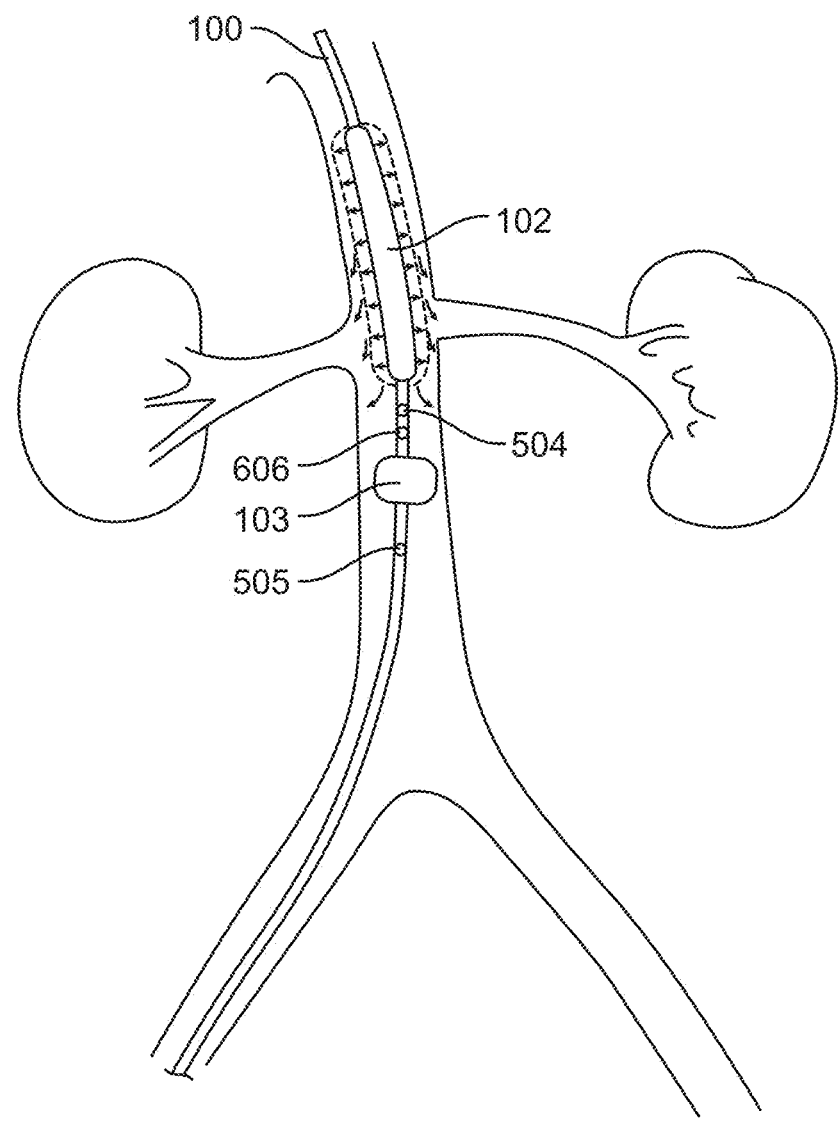
FIG. 7 shows another aspect of the present disclosure where renal artery blood flow augmentation is exerted by periodic inflation and deflation of the first balloon.

FIG. 7 shows an embodiment of the device 100 with both the first balloon 102 and second balloon 103 inflated. Two sensors are shown as sensors 504 and 505 for example. The first balloon 102 may be inflated to such an extent that it does not completely occlude the orifices of the renal arteries. Periodic inflation and deflation of the first balloon 102, indicated with arrows, may augment renal artery blood flow.

Figure 8:
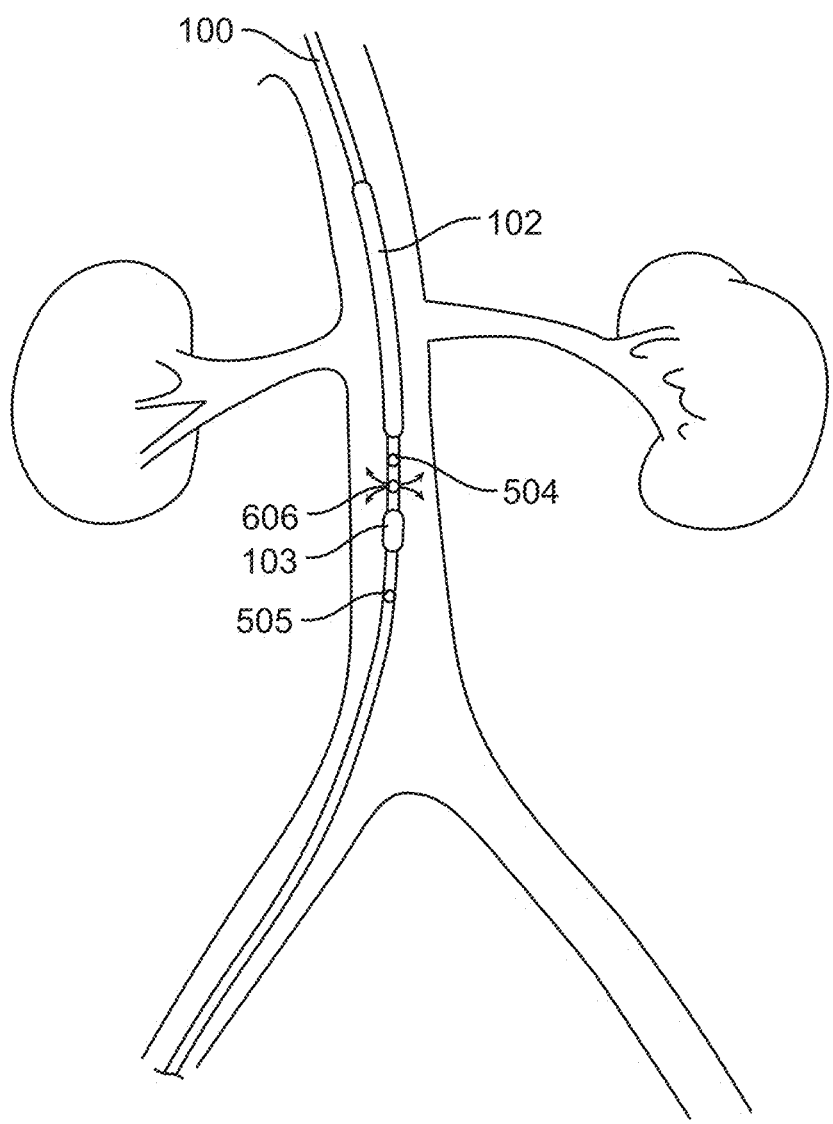
FIG. 8 shows an embodiment of the device at the end of PCI wherein both the first and second balloons have been deflated and a continuous infusion of normal saline is applied for post-procedural hydration.

FIG. 8 shows an embodiment of the device 100 at the end of a percutaneous coronary intervention (PCI), for example. Following PCI, both of the first balloon 102 and the second balloon 103 may be deflated. The balloons may then be either removed from the patient or left to remain inside the abdominal aorta, for example for continuous infusion of normal saline via side aperture 606 for post-procedural hydration.

Figure 9:
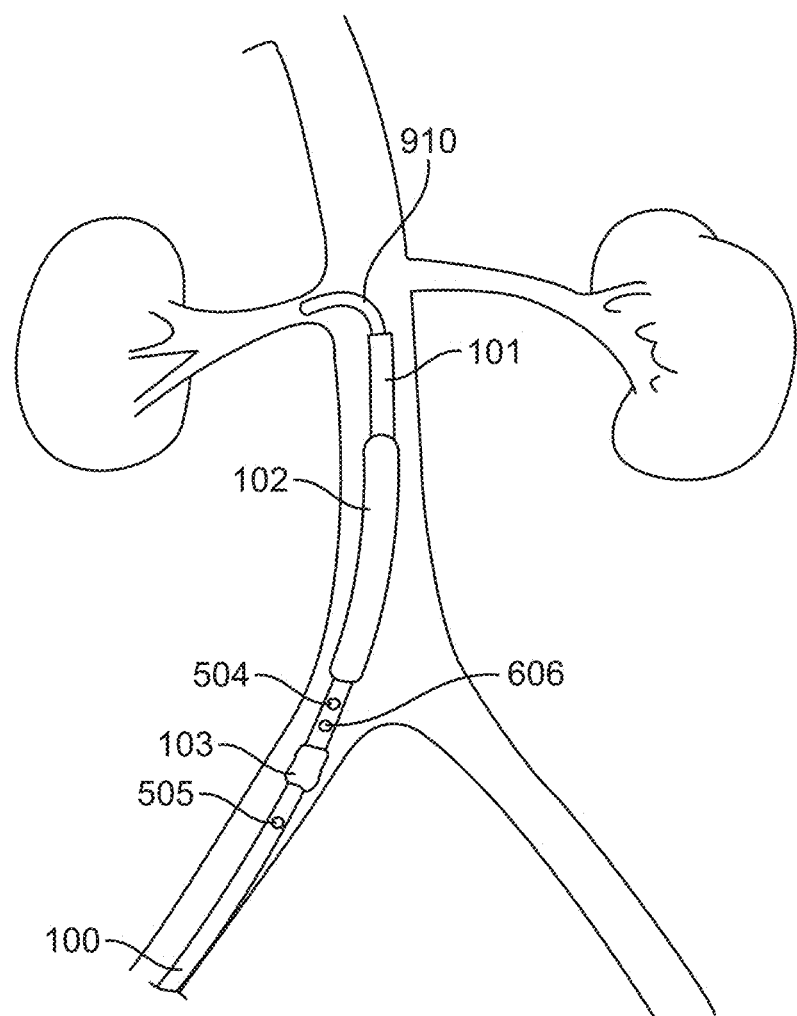
FIG. 9 shows another aspect of the present disclosure wherein a guidewire is used to guide the device for insertion into the renal artery.

The device 100 may alternatively or in combination comprise a guidewire 910. FIG. 9 illustrates an exemplary embodiment of device 100 comprising a guidewire 910. For example, the embodiment of FIG. 8 may further comprise a guidewire 910 which may be inserted into the renal artery via the catheter 101. The catheter may comprise an outer sheath. When the guidewire 910 is inside the renal artery, the outer sheath catheter 101 may also be inserted into the renal artery following the path of the guidewire 910.

Figure 10:
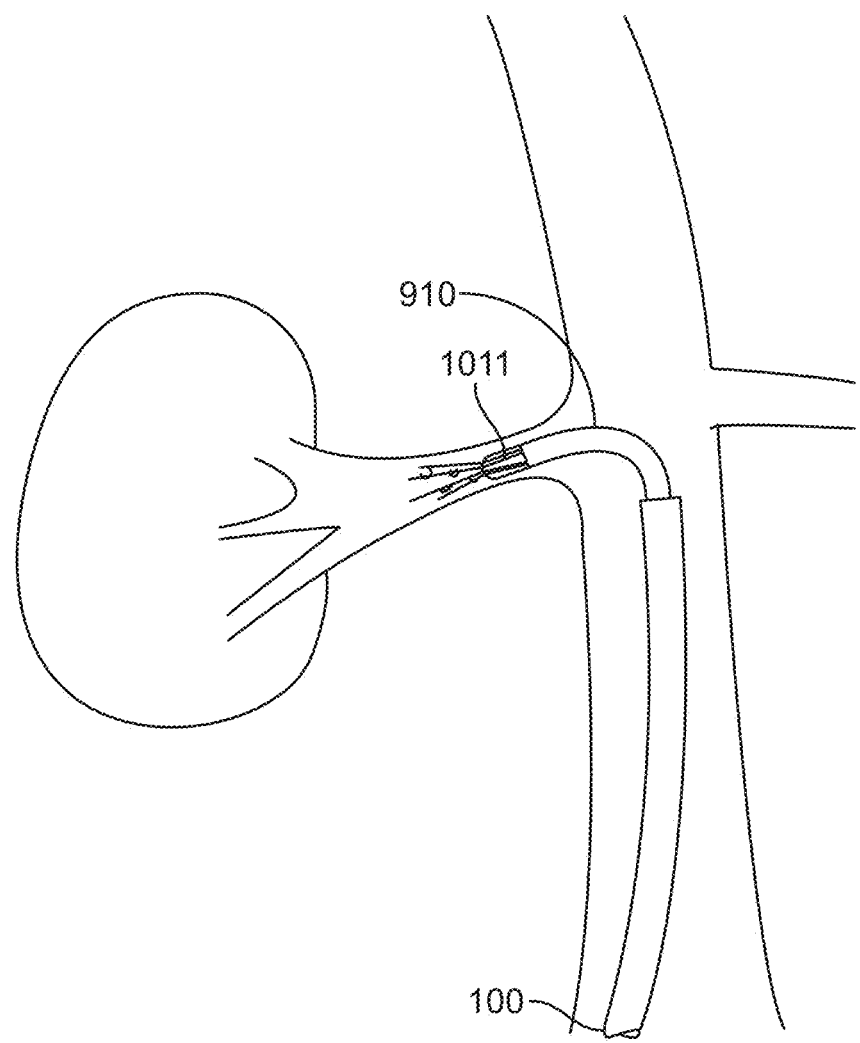
FIG. 10 shows an embodiment with a spinning propeller inserted into renal artery which spins around the central guidewire in order to augment renal artery blood flow toward the kidney.

In some embodiments the device 100 may further comprise a guidewire 910 and a unidirectional flow pump 1011. FIG. 10 shows an embodiment of the device 100 of FIG. 9 further comprising a unidirectional flow pump 1011. The unidirectional flow pump 1011 may for example be a spinning propeller. The spinning propeller 1011 may be inserted from outer sheath catheter 101 into the renal artery via the guidewire 910. Activation of the spinning propeller 1011 such that the propeller 1011 spins around the central guidewire 910 may generate directional augmented renal artery blood flow toward the kidney.

Figure 11A:
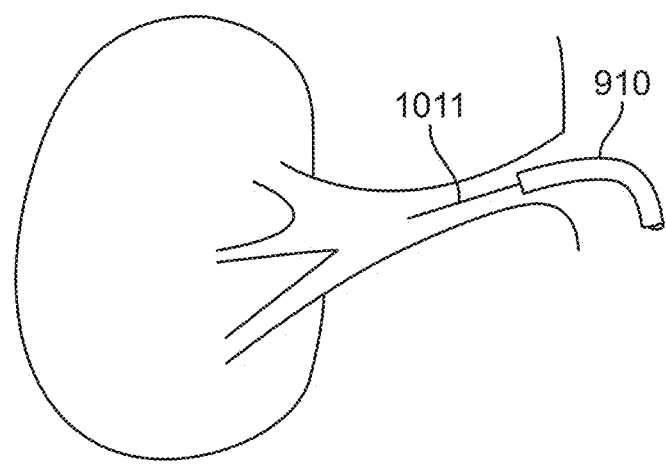
FIGS. 11A-11B show alternative embodiments of a spinning propeller.
Figure 11B:
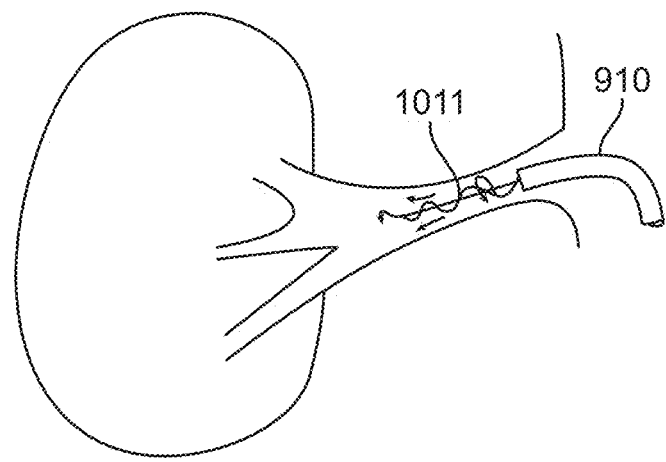

FIGS. 11A and 11B show alternative embodiments of the spinning propeller 1011. The spinning propeller 1011 in some embodiments is wing shape, fin shape, or the like. The spinning propeller 1011 may spin around the central guidewire 910 to generate flow in a unidirectional manner, for example towards a kidney. In some embodiments, the device 100 may further comprise a second catheter comprising a second guidewire and a second spinning propeller for the generation of flow towards a second kidney. In some embodiments, the second spinning propeller may function independently of the first spinning propeller to generate augmented directional blood flow. Alternatively or in combination, the second spinning propeller may function simultaneously with the first spinning propeller to augment blood flow towards both of the kidneys.

MEMS Pump

Microelectromechanical systems (MEMS) (also written as micro-electro-mechanical, MicroElectroMechanical, or microelectronic and microelectromechanical systems, and the related micromechatronics) is the technology of very small devices. MEMS are comprised of components between 1 to 100 micrometers in size (i.e. 0.001 to 0.1 mm), and MEMS devices generally range in size from 20 micrometers (20 millionths of a meter) to a millimeter (i.e. 0.02 to 1.0 mm). They usually comprise a central unit that processes data (the microprocessor) and several components that interact with the surroundings such as microsensors. The fabrication of MEMS evolved from the process technology in semiconductor device fabrication. The basic techniques include deposition of material layers and patterning by photolithography and etching to produce the required shapes. Patterning in MEMS involves the transfer of a pattern into a material. Typically, a MEMS pump will have a patterned vibrating chamber connected a flow inlet and an outlet. Vibration of this chamber is usually driven by piezoelectricity, such as the product of Bartels (http://www.microcomponents.com). The vibration can also be driven by pneumatics (see e.g., Chun-Wei Huang, Song-Bin Huang, and Gwo-Bin Lee, "Pneumatic micropumps with serially connected actuation chambers," Journal of Micromechanics and Microengineering, 16(11), 2265, 2006), electrostatics (e.g., Tarik Bourouina, Alain Bossebuf, and Jean-Paul Granschamp, "Design and simulation of an electrostatic micropump for drug-delivery applications," Journal of Micromechanics and Microengineering, 7(3), 186, 1997), or electrothermal mechanism (Rumi Zhang, Graham A. Jullien, and Colin Dalton, "Study on an alternating current electrothermal micropump for microneedle-based fluid delivery systems," Journal of Applied Physics, 114, 024701, 2013).

Acoustic Wave Pump

Acoustic streaming can be ideal for microfluidic systems because it arises from viscous forces, which are the dominant forces in low Reynolds flows and which usually hamper microfluidic systems. Streaming force can scale favorably with the size of the channel, conveying a fluid through which an acoustic wave propagates and decreases. Because of acoustic attenuation via viscous losses, a gradient in the Reynolds stresses may be manifested as a body force that drives acoustic streaming, as well as streaming from Lagrangian components of the flow. For more information on the basic theory of acoustic streaming, please see Engineering Acoustics/Acoustic streaming. When applied to microchannels, the principles of acoustic streaming typically include bulk viscous effects (dominant far from the boundary layer, though driven by boundary layer streaming), as well as streaming inside the boundary layer. In a micromachined channel, the dimensions of the channels are on the order of the boundary layer thickness, so both the inner and outer boundary layer streaming needs to be evaluated to have a precise prediction for flow rates in acoustic streaming micropumps. The derivation that follows herein is for a circular channel of constant cross-section assuming that the incident acoustic wave is planar and bound within the channel filled with a viscous fluid. The acoustic wave may have a known amplitude and fills the entire cross-section and there are no reflections of the acoustic wave. The walls of the channel can also be assumed to be rigid. Importantly, rigid boundary interaction can result in boundary layer streaming that dominates the flow profile for channels on the order of or smaller than the boundary layer associated with viscous flow in a pipe. This derivation can follow from the streaming equations developed by Nyborg who starts with the compressible continuity equation for a Newtonian fluid and the Navier-Stokes and dynamic equations to get an expression for the net force per unit volume. Eckart may use the method of successive approximations with the pressure, velocity, and density expressed as the sum of first and second order terms. Since the first order terms account for the oscillating portion of the variables, the time average may be zero. The second order terms arise from streaming and are time-independent contributions to velocity, density, and pressure. These non-linear effects due to viscous attenuation of the acoustic radiation in the fluid can be responsible for a constant streaming velocity.

Acoustic wave devices such as surface acoustic wave (SAW) devices have been in commercial use for more than 60 years, with their main applications in communications (e.g. filters and oscillators in mobile phones or televisions). Various microfluidic acoustic wave pumps have been developed to control, manipulate, and mix a minute amount of liquid in microliter to picoliter volumes, including devices based on mechanical moving parts (such as oscillating membranes), electric fields applied to liquids, magnetic fields applied to fluids, or by inducing phase changes in fluids. The surface acoustic wave in some instances is generated by applying an RF signal to a set of interdigitated transducers (IDTs) which lie on top of a piezoelectric material. When the frequency, f, of the RF signal is equal to Vs/p, where Vs is the acoustic velocity of the substrate/piezoelectric system and p is the periodic spacing of the IDT electrodes, then constructive interference occurs and an intense acoustic wave is generated which travels through the piezoelectric substrate. The mode of the acoustic wave is determined by the crystallographic orientation of the piezoelectric material and, in the case of devices using a thin film piezoelectric, the thickness of the piezoelectric layer. For microfluidic applications, a component of the acoustic wave is required in the direction of propagation, and the so-called Rayleigh mode is commonly employed in which an individual atom performs elliptical motion in the plane perpendicular to the surface and parallel to the direction of propagation. However, the excessive damping of the Rayleigh mode by the liquid means that this mode is considered to be unsuitable for sensing applications. The coupling of the acoustic wave into liquid on the surface of the SAW device, which is required for pumping or mixing, occurs through the excited longitudinal waves propagating into the liquid at an angle called the Rayleigh angle, following the Snell law of diffraction as below: The Rayleigh angle, theta, is defined by $\theta' = \sin^{-1}(v_L/v_S)$ where $V_L$ is the velocity of the longitudinal wave in the liquid. However, the energy and the momentum of the longitudinal wave radiated into the liquid are quite useful for liquid pumping and mixing (X. Du et al, "ZnO film based surface acoustic wave micro-pump," Journal of Physics: Conference Series, 76(1), 012047, 2007). A skilled person in the art could prepare and employ an acoustic wave pump based on the theory provided above.

In some embodiments, the device 100 may comprise a flow augmentation means, for example an acoustic wave pump. In some embodiments, the device 100 may further comprise a guidewire and a flow augmentation means to generate augmented directional blood flow into the renal arteries toward the kidney. The flow augmentation means may, for example, comprise one or more of a spinning propeller, a micro-electro-mechanical (MEM) micropump, an acoustic wave pump, or the like. In some embodiments, the flow augmentation means may be a spinning propeller.

In some embodiments, the flow augmentation means may be a micro-electro-mechanical (MEM) micropump. In some embodiments, the flow augmentation means may be an acoustic wave pump.

Figure 12:
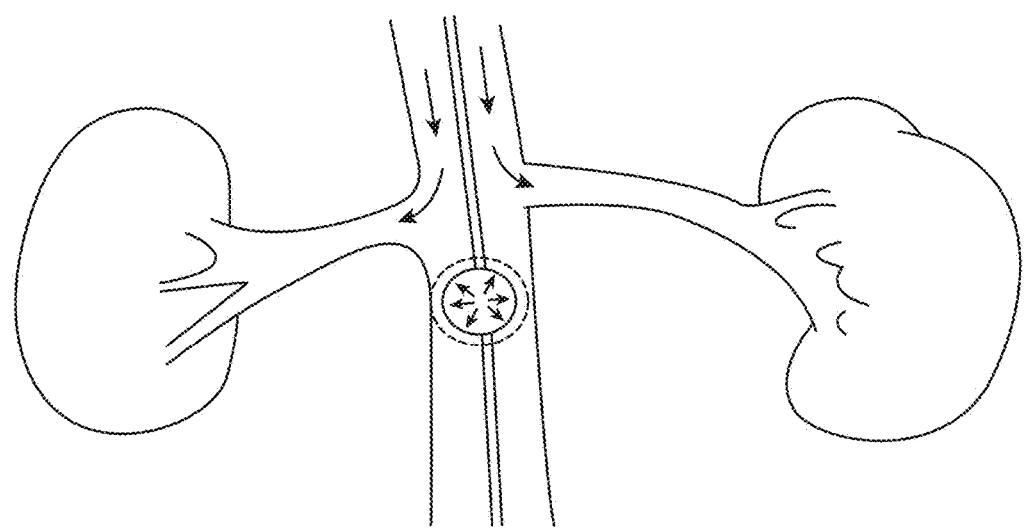
FIG. 12 illustrates an exemplary balloon-type acoustic wave pump at work.

The device 100 comprising an acoustic wave pump may be any of the embodiments described herein. FIG. 12 shows an exemplary acoustic wave pump employed near the renal arteries. The acoustic wave pump may include an inflatable first balloon that, when deflated, may allow blood to flow freely. The first balloon may then inflate and deflate, as indicated by dashed lines, in a preset adjustable frequency in order to create an acoustic wave which may force blood flow to enter the renal arteries, as indicated by the arrows.

Figure 13A:
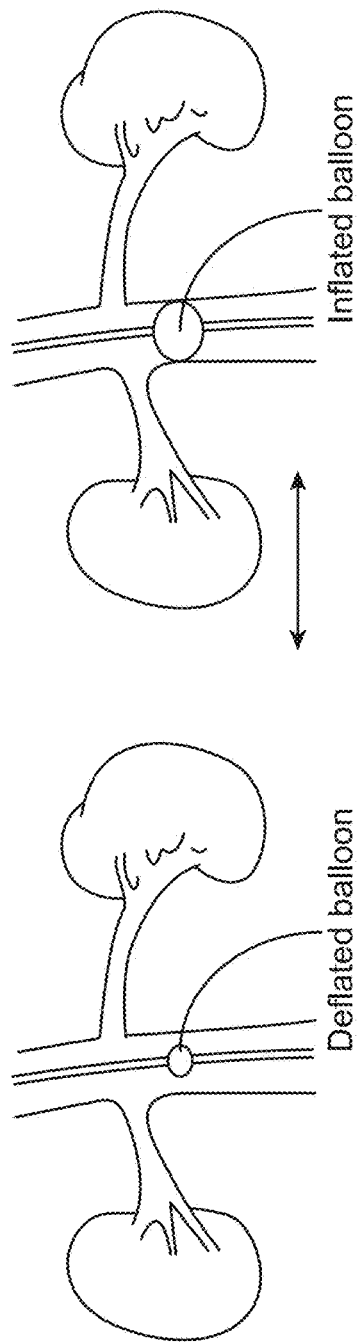
FIGS. 13A-13B show how the exemplary acoustic wave pump works via the inflation and deflation of the balloon.
Figure 13B:
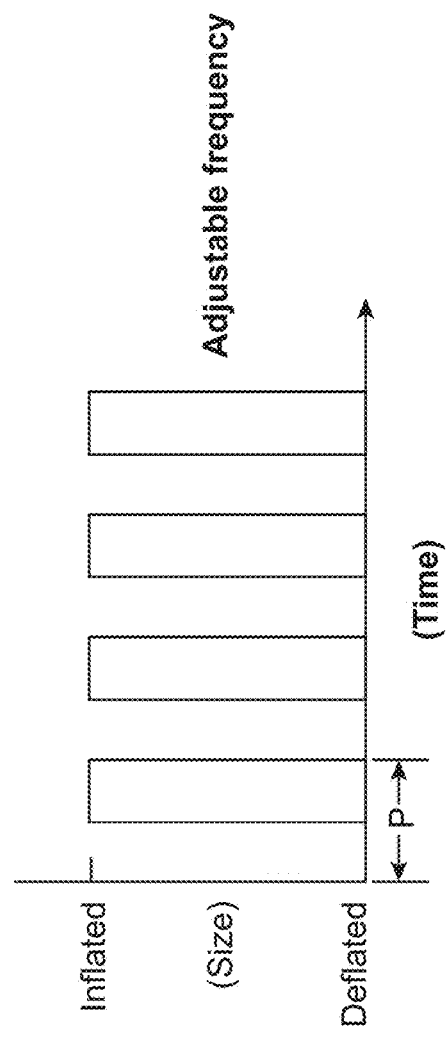

FIGS. 13A-13B shows the acoustic wave pump of FIG. 12 alternating between an inflated state and a deflated state. The size of the balloon may be alternated over time with an adjustable frequency by increasing or decreasing pressure to inflate or deflate the balloon. The inflation-depletion period (p) may for example be adjustable. In some embodiments, the shape of the balloon varies from sphere, cylinder, donut-like to sausage-like shape.

In some embodiments, the balloon may be fully inflated such that its outer circumference contacts the aorta wall, heretofore defined as 100% inflation. In some embodiments, the balloon may be inflated to 90%, 80%, 70%, 60%, 50%, 40%, or 30% inflation. The balloon may alternatively or in combination be inflated within a range from about 99.9% to about 10%, within a range from about 80% to about 20%, or within a range from about 70% to about 30%.

FIGS. 14A-14B illustrates another embodiment of an acoustic wave pump, wherein two balloons may be involved to create an acoustic wave. The second balloon may be shaped such that it surrounds the first balloon. A donut-shaped second balloon may surround an inflated first balloon. The first balloon may be inflated to a pre-determined size and may induce a consistent increased pressure in the abdominal aorta in order to facilitate blood flow into the renal arteries. The second balloon may be inflated and deflated around the first balloon in order to generate the acoustic wave. The wave frequency of the donut-like second balloon may be adjusted to create the desired blood flow toward the renal arteries. The first balloon and second balloon may each be fully inflated. Full inflation of the balloons may prevent unexpected balloon deformation due to aortic blood flow.

Figures 15A, 15B:
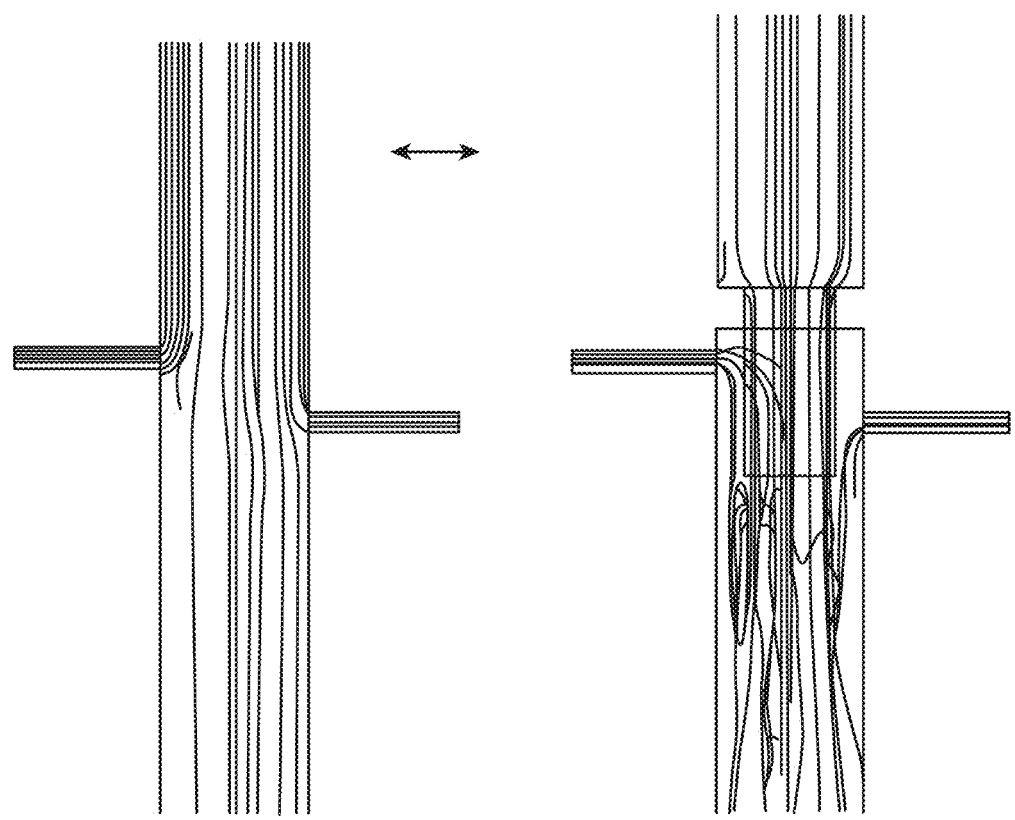
FIGS. 15A-15B show computer-generated blood flow simulation diagrams without (FIG. 15A) and with (FIG. 15B) a first balloon attached to a tunnel membrane. The curved lines represent the streamlines.

Alternatively or in combination, the device 100 may comprise a flow disturbing means which may disturb blood flow in the abdominal aorta so as to reduce the concentration of a contrast media entering the renal arteries. FIGS. 15A-15B show computer generated blood flow simulation diagrams. FIG. 15A shows a blood flow simulation diagram without a flow disturbing means. FIG. 15B shows a blood flow simulation diagram with a flow disturbing means, for example a first balloon attached to a tunnel membrane. The first balloon may for example be a donut-like balloon upon inflation. The curved lines represent blood flow streamlines. Upon inflation, the first balloon may form a hollow cylinder. The outer wall of the inflated first balloon may be in contact with the aorta wall. When the balloon is inflated, a stagnation region, wherein the blood flow rate is zero, may be formed adjacent to the upper wall of the inflated balloon as the blood flow is in laminar regime. As blood flows through the balloon, a new boundary layer along the sidewall of the balloon hole may be generated such that the blood flow is focused towards the very central part of the abdominal aorta. Focusing blood flow towards the center of the aorta from the periphery of the aorta may result in a retardation of the flow of a contrast media from the supra-renal aorta into the orifice of the renal artery. By reducing the flow of contrast media toward the kidneys, CI-AKI may be prevented.

The streamlines, represented by the curved lines in FIGS. 15A-15B, indicate the blood flow routes from the supra-renal aorta. As shown in FIG. 15A, the blood flow streamlines travel from the supra-renal aorta directly into the renal arteries, such that an injected contrast media may enter the renal arteries at a high concentration. In FIG. 15B, the blood flow streamlines curve toward the central part of the aorta before passing through the first balloon. The blood flow streamlines travel from the supra-renal aorta, are diverted past the renal arteries towards the infra-renal aorta, before flowing back towards the renal arteries. An injected contrast media may therefore be diluted in the intra-renal aorta prior to reaching the renal arteries at a lower concentration.

The results of the blood flow simulation shown in FIGS. 15A-15B may provide guidance for the design of embodiments of a flow disturbing means. In some embodiments, the flow disturbing means may be a tunnel membrane adapted to fit inside an aorta wall. The tunnel membrane may be attached to the first balloon. In some embodiments, the flow disturbing means may be an umbrella-like component attached to either the catheter or the first balloon. The umbrella-like component may reduce blood flow by being positioned either above the renal arteries, i.e. in the supra-renal aorta, or below the renal arteries, i.e. in the infra-renal aorta. The flow disturbing means may, for example, be an umbrella-like blood flow reducing component attached to the catheter and positioned at supra-renal aorta. A person skilled in the art will readily recognize any similar shapes, structures, or functions to an umbrella-like blood flow reducing component.

The flow disturbing means may be any device that can disturb blood flow and result in lower renal artery blood intake directly from the supra-renal aorta. The flow disturbing means may be applied to any of the device embodiments described herein, for example the embodiments of FIGS. 16A-16D, 17A-17C, or the like.

One or more of the first balloon and the disturbing means may be coated with contrast-media absorber so as to remove contrast media from the blood, further diluting the concentration of the contrast media and reducing potential harm to the kidneys, for example CI-AKI, caused by the contrast media.

Figure 16A:
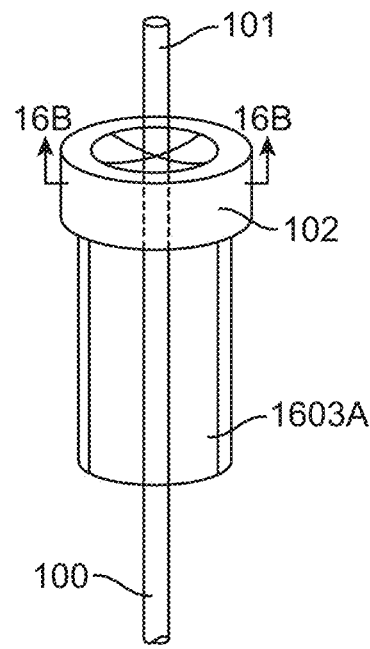
FIGS. 16A-16D show another aspect of the present disclosure wherein a disturbing means is extended toward the infra-renal aorta to further confine the renal arteries to intake blood from the infra-renal aorta.
Figure 16B:
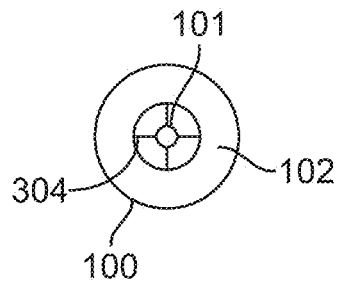

FIG. 16A illustrates another embodiment of a device 100 for treating or preventing AKI, for example CI-AKI. As illustrated in FIG. 16A, the device 100 may comprise a catheter 101 with a first balloon 102 attached to a disturbing means. The disturbing means may for example comprise a tunnel membrane 1603A as shown. FIG. 16B shows a top-down cross-sectional view of the embodiment of FIG. 16A wherein at least one connection tube 304 from the catheter 101 is depicted. The first balloon may for example be donut-shaped such that a hollow area is created between the inner edge of the inflated balloon 102 and the catheter 101 through which blood may flow from the supra-renal aorta to the infra-renal aorta.

Figure 16C:
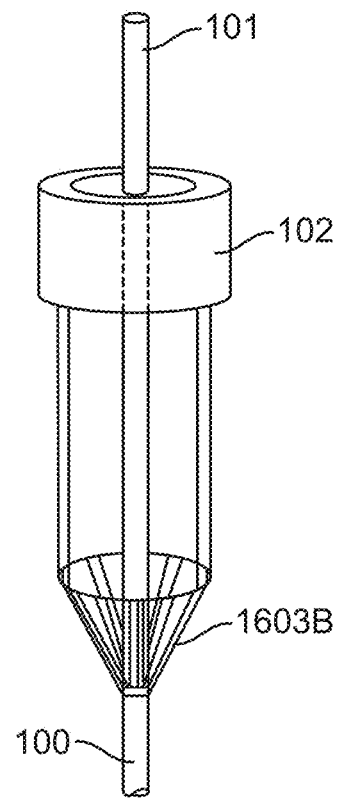
Figure 16D:
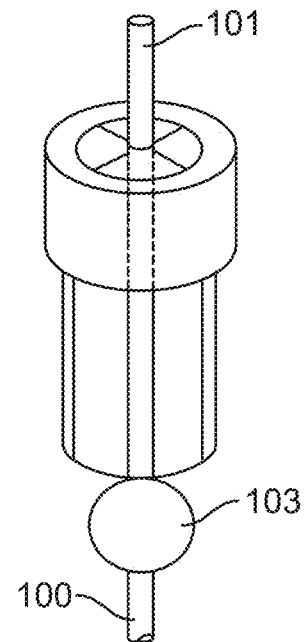

The device 100 may further comprise a second balloon 103 as shown in FIG. 16D. The second balloon 103 may be attached to the tunnel membrane 1603A. The first balloon 102 may for example be located in the supra-renal aorta and be larger in diameter than the second balloon 103 such that the first balloon 102 may contact the aorta wall. The second balloon 103 may provide drag to deploy the tunnel membrane 1603A. In some embodiments the first balloon 102 may not fully inflate to contact the aorta wall and therefore leave a small space around the first balloon 102 through which blood may pass.

The disturbing means may alternatively or in combination comprise an umbrella-like blood flow reducing component 1603B as shown in FIG. 16C. During insertion of the device 100, the umbrella-like component 1603B may be folded to allow free flow of blood. Upon being positioned such that the disturbing means sits near or below the renal arteries, the umbrella-like component 1603B may be unfolded by the downward direction of blood flow.

The disturbing means may for example be made of soft plastics. In some embodiments, the disturbing means may for example be made of semi-soft plastics. Alternatively or in combination, the disturbing means may for example be made of metal having flexibility, such as a metal wire. In some embodiments the tunnel membrane may be a flexible film such as one or more of polytetrafluoroethene (PTFE), expanded polytetrafluoroethene (ePTFE), silicone rubber, polyurethane, poly(ethylene terephthalate), polyethylene, polyether ether ketone (PEEK), polyether block amide (PEBA), or the like, or any combination thereof.

In some embodiments, the infra-renal side of the balloon or of the disturbing means, for example, a tunnel membrane, may inject normal saline or other medications into the aorta via one or more injection hole. Injection of normal saline may, for example, dilute a contrast media before flowing into the renal arteries. The injection hole or multiple injection holes may be located on the first balloon. At least one injection hole or multiples injection holes may be located on the catheter near the first balloon. At least one injection hole or multiple injection holes may be part of one or both of the first balloon and the catheter. In some embodiments, the injection holes may be located at an infusion tube. The infusion tube may for example be made of one or more of a material selected from the group consisting of teflon, polyoxymethylene copolymer, polyimides, polycarbonate, polyetherimide, polyetheretherketone, polyethylene, polylactic acid, polylactide acid, polystyrene, polyurethane, PVC, thermoplastic elastomer, and combinations thereof, and the like.

Figure 17A:
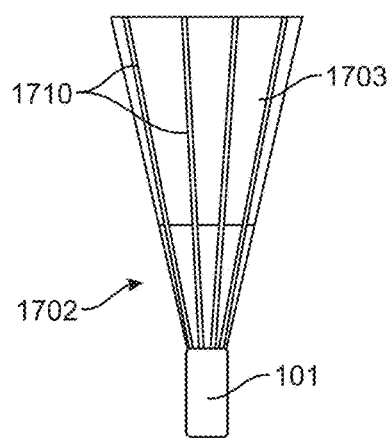
FIGS. 17A-17C shows another embodiment of a disturbing means comprising a cone-shaped wire device partially covered by the tunnel membrane.
Figure 17B:
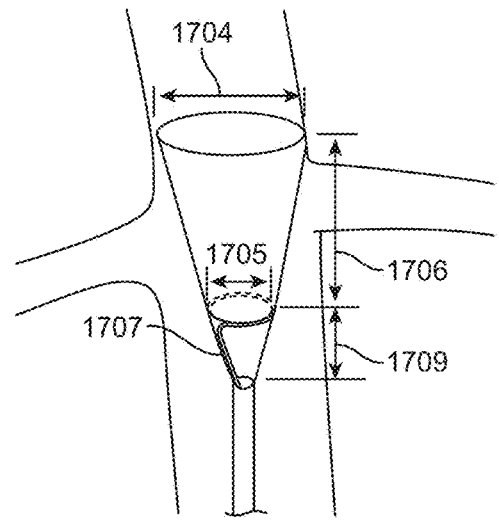
Figure 17C:
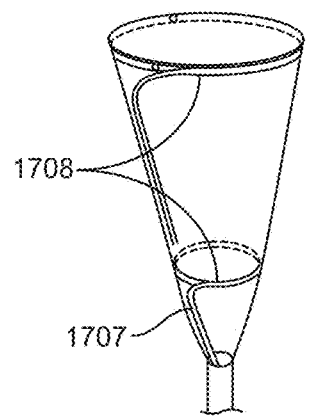

FIGS. 17A-17C show another embodiment of a flow disturbing means. As illustrated in FIG. 17A, the flow disturbing means may be a cone-shaped wire device 1702 partially covered with tunnel membrane 1703 which is deployed from catheter 101. Tunnel membrane 1703 may be substantially similar to the tunnel membrane 1603A of FIG. 16. The cone-shaped wire device 1702 may comprise a plurality of wires 1710.

FIG. 17B shows the device 1702 located in the abdominal aorta with exemplary specifications. The diameter of the distal opening 1704 may for example be about 3 to about 3.2 cm, or preferably about 3.0 cm. The cone-shaped wire device 1702 may have outer wire rim 1704 dimensions such that the device 1702 may fit either tightly within the aorta, for example, a diameter of about 3 to about 3.2 cm, or loosely situated with little space between the device 1702 and the aorta wall allowing blood seeping through, for example a diameter of less than about 3 cm. The diameter of the distal opening 1704 may be designed based on various diameters of a patient's aorta in which the device 1702 will be deployed, which typically range from about 5 cm to about 2 cm. The distal opening 1704 may for example have a diameter of about 5 cm to about 1.5 cm; or a diameter of about 4.5 cm to about 1.7 cm. In some embodiments, the distal opening 1704 may have a diameter of about 4 cm to about 1.8 cm, for example about 3.5 cm to about 1.8 cm or about 3 cm to about 2.0 cm.

The height 1706 of the tunnel membrane 1703 may be about 1.5 cm to about 4 cm, for example, about 2 cm to about 3.5 cm or about 2.5 cm to about 3.0 cm. In some embodiments, the height 1706 of the tunnel membrane 1703 may be about 2 cm, about 3 cm, or about 4 cm.

The tunnel membrane 1703 may extend from the edge of the distal opening 1704 to the proximal opening 1705 of the cone-shaped wire device 1702. The proximal opening 1705 may allow blood to flow through the tunnel membrane 1703 with restricted speed such that blood flow is disturbed to allow the renal arteries to intake blood from the infra-renal aorta. Disturbing blood flow may dilute an injected contrast media prior to entering the renal arteries. In some embodiments, effective blood flow disturbance may be generated with the diameter of the proximal opening 1705 at about one-fourth to about three-fourths of the diameter of the distal opening 1704. In some embodiments, the diameter of the proximal opening 1705 may be about one-third of the diameter of the distal opening 1704. For example, the diameter of the bottom opening 1705 may be about 1.0 cm when the diameter of the distal opening 1704 is about 3 cm. The blood releasing height 1709 from the proximal opening 1705 may be designed to be about one-half to about three times the diameter of the proximal opening 1705. The ratio relationship between the blood releasing height 1709 and proximal opening 1705 may be based on how the wire device 1702 restricts blood flow to create disturbance, the structural strength of the wire device 1702, and the diameter relationship between the distal opening 1704 and the proximal opening 1705.

To support the structure of an embodiment such as the cone-shaped wire device 1702, the wire device may comprise at least 3 wires 1710. In some embodiments, there may be 4 to 24 wires, 5 to 22 wires, 6 to 20 wires, 8 to 18 wires, or 10 to 16 wires 1710. In some embodiments, there may be 3, 4, 5, 6, 7, 8, 9, 10, 11, 12, 13, 14, 15, 16, 17, 18, 19, or 20 wires 1710 in the wire device 1702 partially covered by the tunnel membrane 1703. A skilled person in the art may prepare a wire device in accordance with the practice of the present disclosure to any number of wires suitable to provide a disturbing means. The wire may be made of any superelastic or pseudoelastic material, for example nitinol, alloys of copper-zinc-aluminum (CuZnAl), alloys of copper-aluminum-nickel (CuAlNi), alloys of copper-aluminum, alloys of nickel-titanium, or any combination thereof. In some embodiments, the superelastic material may comprise one or more of copper, aluminum, nickel, titanium, or any combination thereof. Specific structures may be formed by routing the wires, for example by bending or weaving the wires into a final shape. Alternatively or in combination, specific structures may be formed by cutting a superelastic tube, for example laser cutting out portions to leave a final wire structure. Alternatively or in combination, specific structures may be for my cutting a superelastic fleet, for example laser cutting out parts and annealing the fleet into a final cone-shape.

Pseudoelasticity, sometimes called superelasticity, is an elastic (reversible) response to an applied stress, caused by a phase transformation between the austenitic and martensitic phases of a crystal. It is exhibited in shape-memory alloys. Pseudoelasticity is from the reversible motion of domain boundaries during the phase transformation, rather than just bond stretching or the introduction of defects in the crystal lattice (thus it is not true superelasticity but rather pseudoelasticity). Even if the domain boundaries do become pinned, they may be reversed through heating. Thus, a superelastic material may return to its previous shape (hence, shape memory) after the removal of even relatively high applied strains.

The shape memory effect was first observed in AuCd in 1951 and since then it has been observed in numerous other alloy systems. However, only the NiTi alloys and some copper-based alloys have so far been used commercially.

The disturbing means of device 100, for example the cone-shaped wire device 1702, may further comprise an infusion tube 1707 and one or more injection hole 1708 for delivery of normal saline or other medications. Delivery of normal saline, for example, may further dilute the contrast media prior to flowing into the renal arteries. As shown in FIG. 17C, one or more injection holes 1708 may be located at the distal opening 1704 or the proximal opening 1705, or a combination thereof. For example, a plurality of injection holes 1708 may be located at both of the distal 1704 and proximal 1705 openings of the cone-shaped wire device 1702. Alternatively or in combination, the one or more injection hole 1708 may be located on the catheter 101, for example near the tip of the catheter 101 where the disturbing means is deployed.

In some embodiments, the cone-shaped wire device 1702 may comprise an upper cylinder portion 1811 as illustrated in FIG. 18A. The cone-shaped wire device 1702 may be partially covered with tunnel membrane 1703 from the rim of the distal opening 1704 to the proximal opening 1703. The device 1702 may be deployed from the catheter 101. FIG. 18B shows a top-down view of the device 1702 with upper cylinder portion 1811. FIG. 18C shows a bottom-up view of the device 1702 with upper cylinder portion 1811. FIG. 18D provides an isometric view of the device 1702 with upper cylinder portion 1811.

The upper cylinder portion 1811 may be used to form tight contact of the device with the aorta wall. Tight contact may support the device 1702 against high pressure due to a high blood flow rate. Tight contact between the device 1702 and the aorta wall may further prevent a contrast media from leaking through the contact interface.

To avoid occlusion of the renal arteries branching from the supra-renal aorta by upper cylinder portion 1811, which is about 0.5 cm apart, the height of the upper cylinder portion 1811 should not be more than 0.5 cm, or about the distance between the renal arteries and the supra-renal aorta. The height 1806 of the tunnel membrane 1703 from the distal opening 1705 to the proximal opening 1704 should be about 1.5 cm to about 4 cm, for example about 2 cm to about 3.5 cm or about 2.5 cm to about 3.0 cm.

Figure 19A:
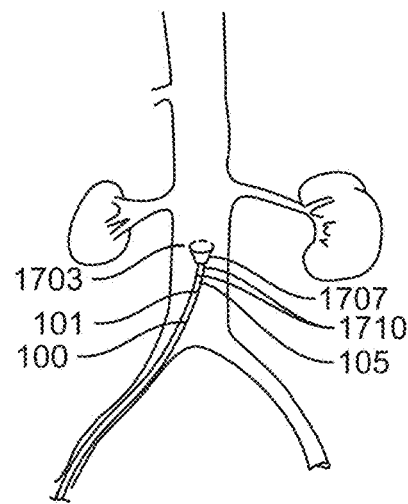
FIGS. 19A-19C illustrate the deployment of an embodiment of a catheter device to treat or prevent AKI.
Figure 19B:
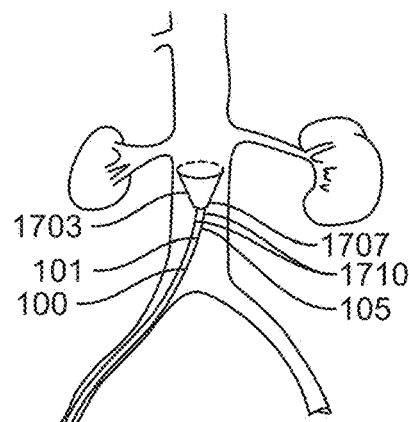
Figure 19C:
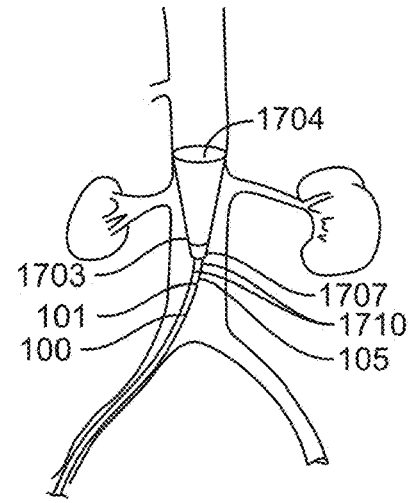

FIG. 19 shows an embodiment of a cone-shaped wire device 1702 being deployed inside the abdominal aorta. FIG. 19A shows the device 1702 with the tunnel membrane 1703 at the beginning of deployment from the catheter 101. FIG. 19B shows the tunnel membrane 1704 partially deployed into the abdominal aorta. FIG. 19C shows the tunnel membrane 1704 fully deployed into the abdominal aorta.

The catheter device 100 comprising a cone-shaped wire device 1702 may further comprise at least one position indication means 105, for example a radio-opaque marker or the like, to determine the location of the catheter 101 for proper deployment of the tunnel membrane 1703 in the supra-renal aorta near the orifices of the bilateral renal arteries. The device 1702 may for example be inserted into the abdominal aorta via either a transfemoral arterial approach, a trans-brachial artery approach, or a trans-radial artery approach.

Figure 20A:
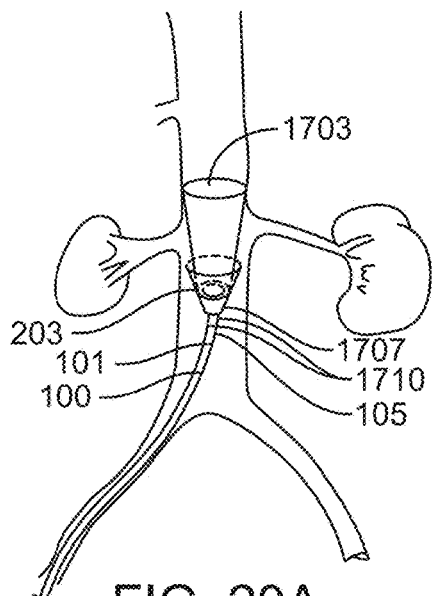
FIGS. 20A-20D illustrate another embodiment of a device for treating or preventing AKI.
Figure 20B:
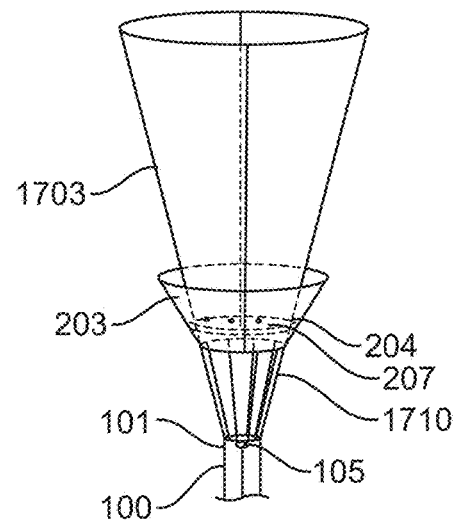
Figure 20C:
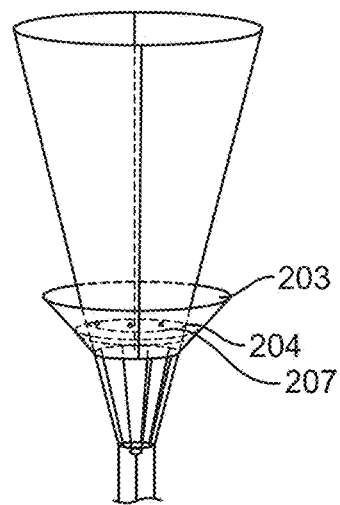
Figure 20D:
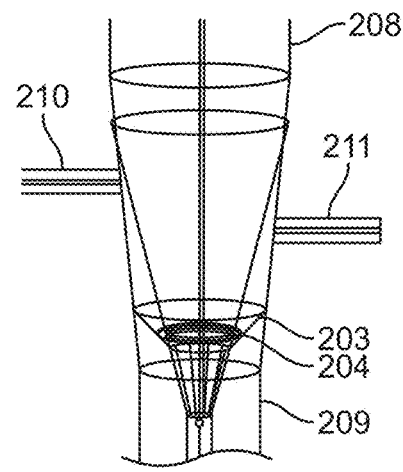

In some embodiments, the cone-shaped wire device 1702 may further comprise a blood flow diversion means in conjunction with the tunnel membrane, wherein deployment of the flow diversion means inside the abdominal aorta may occlude the orifices of both sides of the renal arteries while continuing to allow blood to flow through the tunnel membrane. FIG. 20A shows an exemplary embodiment of a device 100 comprising a cone-shaped wire device 1702 comprising a catheter 101, tunnel membrane 1703, infusion tube 1707, multiple supporting wires 1710, and a radio-opaque marker 105 on the tip of the catheter 101. The device 1702 may further comprise one or more of a blood flow diversion means 203, for example a seal membrane, and a donut-like balloon 204. FIG. 20B shows the embodiment of FIG. 20A with donut-like balloon 204 in a deflated state. The donut-like balloon 204 may be positioned between the tunnel membrane 1703 and the seal membrane 203. FIG. 20C shows the donut-like balloon 204 in an inflated state. Inflation of the donut-like balloon 204 deploys the seal membrane 203. The donut-like balloon 204 may further comprise at least one aperture 207 to allow for infusion of normal saline or medications into the abdominal aorta. The at least one aperture 207 may be substantially similar to the side aperture 606 previously described herein. FIG. 20D shows the upper rim of the tunnel membrane 1703 positioned in the supra-renal aorta 208 near the orifices of the right renal artery 210 and the left renal artery 211. Deployment of the seal membrane 203 via inflation of the donut-like balloon 204 may further reduce blood flow from the infra-renal aorta 209 to the renal arteries 210, 211. When a bolus influx of contrast media or other harmful agent occurs, deployment of the device 100 may prevent blood flowing from the supra-renal aorta from entering the renal arteries where the contrast media may have toxic effects.

Figure 21A:
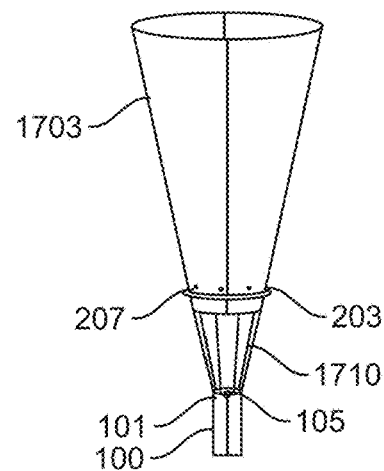
FIGS. 21A-21C illustrate another embodiment of the present disclosure comprising a catheter with a tunnel membrane, multiple supporting wires, and a donut-like balloon.
Figure 21B:
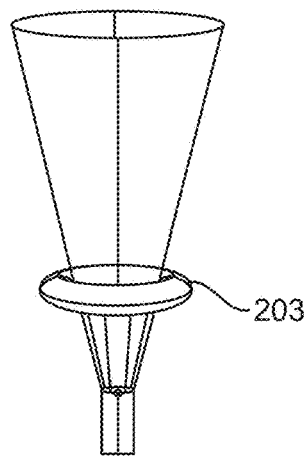
Figure 21C:
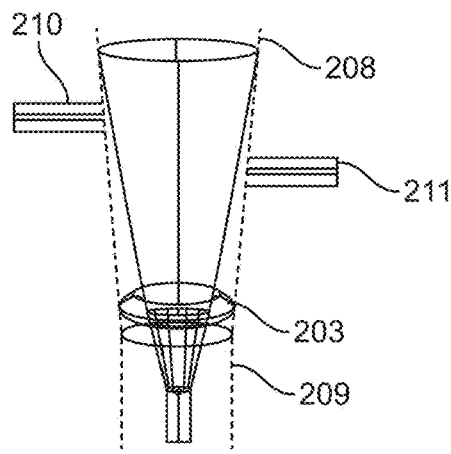

FIGS. 21A-21C illustrates yet another embodiment of a cone-shaped device 1702. The device 100 comprises catheter 101 which may allow the deployment of tunnel membrane 1703, a donut-like balloon 203, multiple supporting wires 1710, and a radio-opaque marker 105 on the tip of the catheter 101. At least one aperture 207 may be on the donut-like balloon 203, for example to allow infusion of normal saline or medication. FIG. 21A shows the donut-like balloon 203 in a deflated state. The donut-like balloon 203 is positioned at the lower end of the tunnel membrane 1703. FIG. 21B shows the donut-like balloon 203 in an inflated state. The size of the donut-like balloon 203 may vary in order to optimally exert its function. FIG. 21C shows the upper rim of tunnel membrane 1703 positioned in the supra-renal aorta 208 near the orifices of the bilateral renal arteries 210, 211 with the donut-like balloon 203 inflated to further reduce blood flow from infra-renal aorta 209 to the right renal artery 210 and the left renal artery 211 such that a bolus influx of contrast media or other harmful agent flowing from the supra-renal aorta 208 may be prevented from entering the renal arteries 210, 211 and having toxic effects.

Figure 22A:
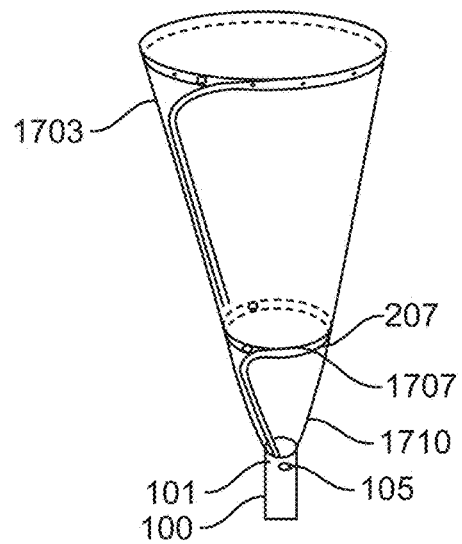
FIGS. 22A-22B illustrate yet another embodiment of the present disclosure.
Figure 22B:
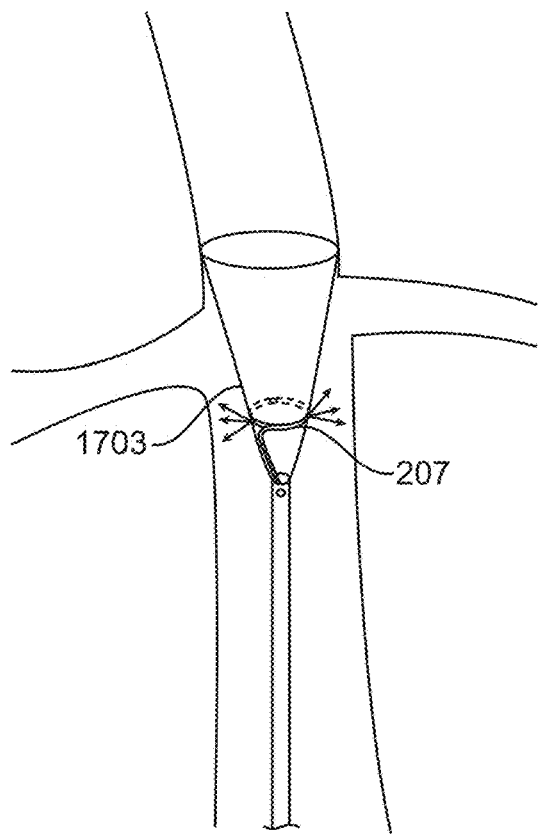

FIGS. 22A-22B illustrate yet another embodiment of device 100 deployed in the abdominal aorta. FIG. 22A shows an embodiment of the device 100, for example the embodiment of FIG. 17 which comprises a cone-shaped wire device 1702 deployed from catheter 101. The cone-shaped wire device 1702 may comprise a tunnel membrane 1703, infusion tube 1707, and one or more supporting wires 1710. The device 1702 may further comprise a position indication means 105, such as a radio-opaque marker. The radio-opaque marker 105 may be on the tip of catheter 101. At least one aperture 207 may be on the infusion tube 1707 to allow infusion of normal saline or medication into the abdominal aorta. The aperture 207 may be substantially similar to the injection hole 1708 previously described herein. FIG. 22B shows the device positioned in the supra-renal aorta near the orifices of the bilateral renal arteries such that the upper rim of the tunnel membrane 1703 makes contact with the inner wall of the aorta and diverts blood flow away from the renal arteries. Saline infusion through aperture 207, as indicated by arrows, may dilute a contrast agent prior to entering the renal arteries.

Figure 23:
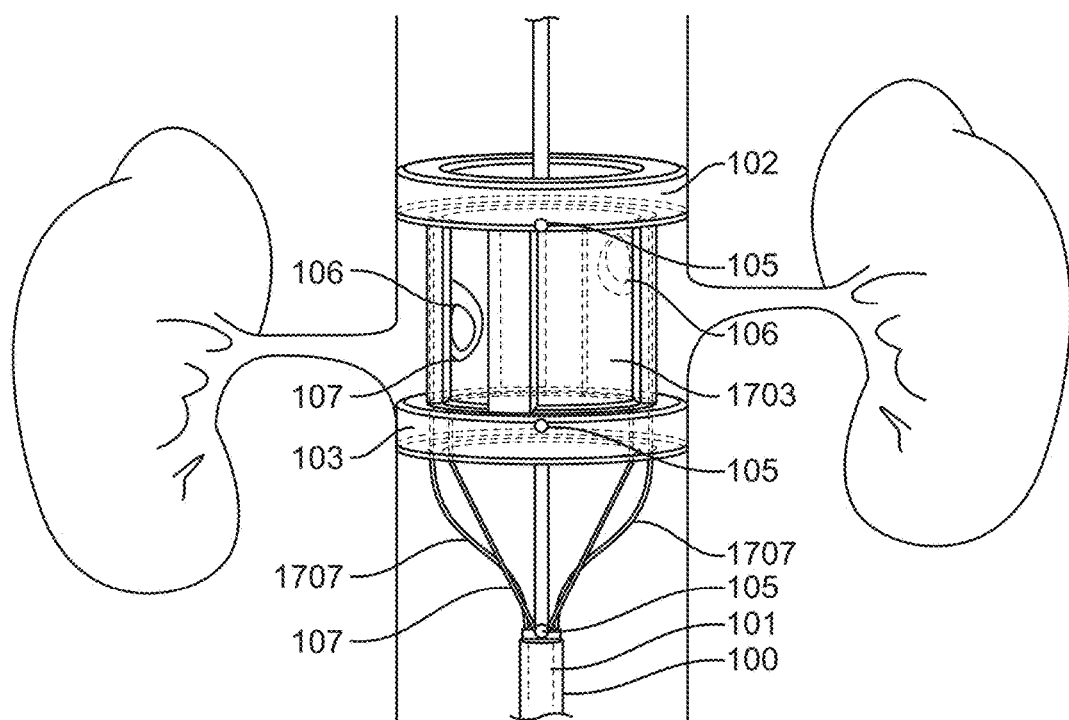
FIG. 23 illustrates still another embodiment of the present disclosure. The device shown comprises a catheter having a tunnel membrane, a donut-like balloon in the supra-renal aorta near the orifices of the bilateral renal arteries, a donut-like balloon in the infra-renal aorta near the orifices of the bilateral renal arteries, three position indication means, two infusion tubes for infusing fluid into or out of the balloons, two apertures on the tunnel membrane, and a wire surrounding the apertures.

FIG. 23 shows yet another embodiment of catheter device 100 comprising a balloon catheter with a blood flow disturbing means. The device 100 may comprise a catheter 101, tunnel membrane 1703, first balloon 102 at the distal end of the tunnel membrane, second balloon 103 at the proximal end of the tunnel membrane, at least one infusion tube 1707 for infusing fluid into or out of the balloons, at least one position indication means 105, and at least one aperture 106 on the tunnel membrane with a wire 107 surrounding the aperture such that opening of the aperture is controlled by the wire. The tunnel membrane 1703 may be a flow disturbing means, for example device 1702 as previously described herein, such that the tunnel membrane 1703 shunts blood flowing from the supra-renal aorta through the tunnel membrane 1703, bypassing the renal arteries, into the intra-renal aorta. Flow disturbance may be further facilitated by inflation of one or both of the distal balloon 102 and proximal balloon 103 to contact the wall of the supra-renal aorta and the wall of the infra-renal aorta, respectively. The aperture 106 may be substantially the same as the aperture 207 described previously herein. The wire 107 surrounding the aperture 106 may be used to keep the aperture 106 closed during the shunting period. The shunting period may be synchronized with the injection of a contrast media by a physician. The shunting period should be kept to a minimum amount of time to shunt the contrast media but not long enough to cause renal ischemia by preventing blood flow to the kidneys. The kidneys are resistant to transient ischemia, therefore the shunting period may be tuned to avoid ischemia.

The position indication means 105 may for example be a radio-opaque marker. One or more position indication means 105 may be located on the tip of the catheter 101, on the proximal balloon 103, on the distal balloon 102, or any combination thereof. The position indication means 105 may be used to monitor the position of the device 100 upon insertion, during use, and during removal. The device 100 may be inserted into the abdominal aorta for example by using either a trans-femoral arterial approach, a trans-brachial artery approach, or a trans-radial artery approach.

In some embodiments, the aperture 106 and the surrounding wire 107 comprise at least one set of the aperture 106 and the surrounding wire 107 on the tunnel membrane. In some embodiments, there are one to four sets, two to six sets, three to nine sets, four to twelve sets, five to fifteen sets, or six to eighteen sets. In some embodiments, there may be 1, 2, 3, 4, 5, 6, 7, 8, 9, 10, 11, 12, 13, 14, 15, 16, 17, or 18 sets of the aperture and the surrounding wire on the tunnel membrane. If needed, a person skilled in the art can prepare a wire device in accordance with the practice of the present disclosure to any number sets of the aperture and the surrounding wire suitable to provide a flow passage means. The wire may be any superelastic material, for example nitinol. The wire may be made of any superelastic or pseudoelastic material, for example nitinol, alloys of copper-zinc-aluminum (CuZnAl), alloys of copper-aluminum-nickel (CuAlNi), alloys of copper-aluminum, alloys of nickel-titanium, or any combination thereof. In some embodiments, the superelastic material may comprise one or more of copper, aluminum, nickel, titanium, or any combination thereof.

Figure 24A:
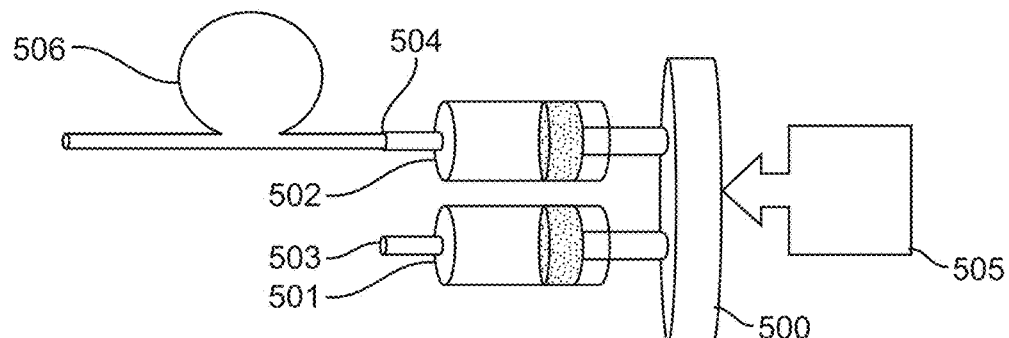
FIGS. 24A-24B illustrate an exemplary device for synchronized injection of contrast agent and medications in treating or preventing AKI.
Figure 24B:
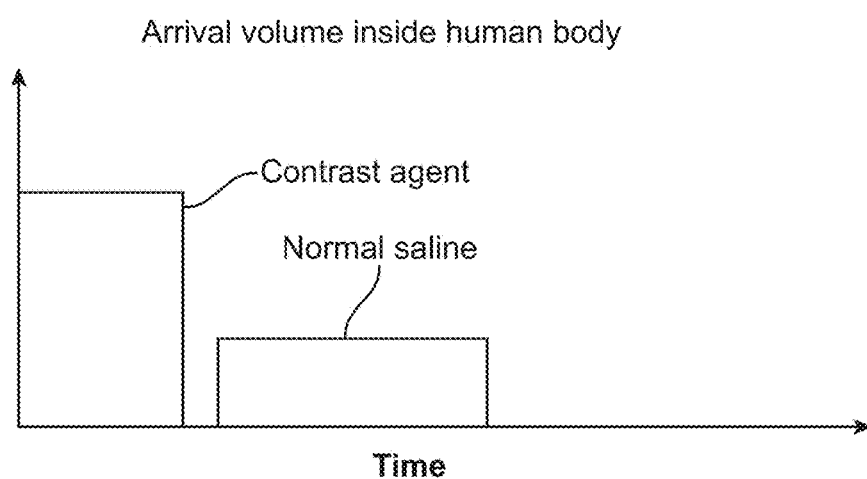

Embodiments of device 100 described herein may be used in combination with a means to synchronize injection of contrast agent and/or medication for the treatment or prevention of AKI. FIGS. 24A-24B show an embodiment of an injection device which may be used as a synchronization means. FIG. 24A shows the injection device comprising an injector 500, contrast agent chamber 501 with contrast agent outlet 503, medication chamber 502 with medication outlet 504, and a common injection actuator 505. The medication chamber 502 may for example contain normal saline. The chambers 501 and 502 comprising outlets 503 and 504 respectively may for example be syringes. Injection may for example occur by depressing the injector 500 in the direction of outlets 503 and 504. The proportion of contrast agent and normal saline injected can be adjusted by adjusting the relative diameters or the relative dimensions of syringes 501 and 502 to control the flow rate. The injection outlet 504 of normal saline may further be connected to a volume reservoir 506 for generating a time difference between the actual arrival time of the contrast agent and the actual arrival time of the inside the abdominal aorta, as illustrated in FIG. 24B.

Figure 25:
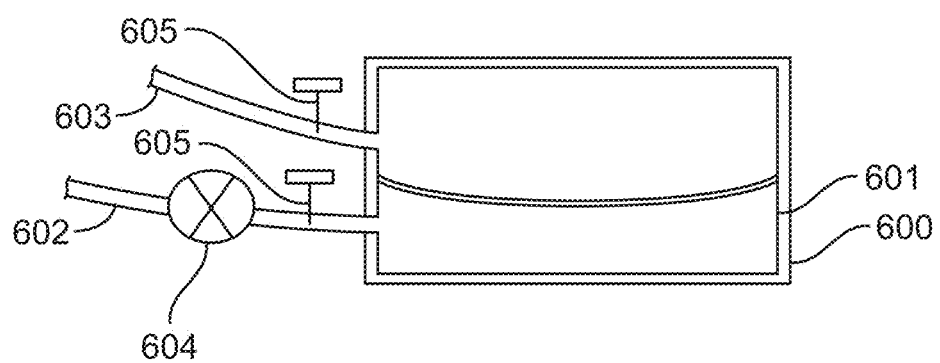
FIG. 25 illustrates an embodiment of a device for balancing fluid flow in and out of a human body. The device shown comprises a box containing fluids or fluid conduits to allow inflow into and outflow out of the human body.

Embodiments of the device 100 described herein may be used alternatively or in combination with a means to balance fluids entering and leaving the body of a patient. FIG. 25 shows an embodiment of a balancing means 600 comprising a fluid-containing box 601, an inlet conduit 602 to provide fluid flow into the body, and an outlet conduit 603 to provide for fluid to flow out of the body. The box 601 may contain two chambers within a single larger container in order to preserve a total volume of the inflow and outflow fluids. A pump 604 may be used to actively pump fluids. Fine measuring units 605 may be used to measure the volumes of the inflow and outflow fluids.

Another aspect of the present disclosure provides a method for treating CI-AKI. The method may comprises steps of: inserting the catheter device into the abdominal aorta; placing the catheter in the supra-renal aorta; and deploying the disturbing means at a position which allows for blood flow disturbance to dilute the contrast media before being taken into the renal arteries. Insertion of the device into the abdominal aorta may for example occur by either a trans-femoral artery approach a trans-branchial artery approach, or a trans-radial artery approach. In some embodiments, the catheter device may further include a guidewire and a flow augmentation means. In some embodiments, the method may further comprise infusion of one or more of normal saline or medications into the supra-renal abdominal aorta by one or more injection holes in fluid communication with an infusion tube, the catheter, or both.

Another aspect of the present disclosure may provide a method for treating CI-AKI is disclosed. The method may comprise steps of: inserting the catheter device comprising a balloon catheter having a first balloon, a second balloon, at least one sensor into abdominal aorta; placing the balloon catheter at a position such that the first balloon is located in the supra-renal aorta near the orifices of the bilateral renal arteries and the second balloon is located in the infra-renal aorta near the orifices of the bilateral renal arteries; inflating the first balloon to occlude the orifices of both sides of the renal arteries during the application of contrast media;

deflating the first balloon after the contrast media has been completely employed; inflating the second balloon to an extent so as not to fully occlude blood flow in the aorta; deflating the second balloon; and optionally infusing normal saline and/or suitable medication into the supra-renal aorta via a side aperture.

In some embodiments, insertion of the catheter device into the abdominal aorta may for example occur by either a trans-femoral arterial approach, a trans-brachial artery approach, or a trans-radial artery approach. In some embodiments, the balloon catheter may further comprise a guidewire and a spinning propeller. In some embodiments, the method further comprises inserting a guidewire into the renal artery. In some embodiments, the method further comprises inserting a spinning propeller into renal artery along the guidewire. In some embodiments, the method further comprises spinning the spinning propeller around the central guidewire to generate directional augmented renal artery blood flow toward the kidney.

The present disclosure may also provide a system comprising a catheter device, such as described herein, for treating AKI. In some embodiments, the AKI is CI-AKI. In some embodiments, the device may comprise a catheter, a position indication means on the catheter, and a flow disturbing means retractable into the catheter, wherein the flow disturbing means may be positioned in the suprarenal aorta to provide blood flow disturbance as described herein. In some embodiments, the device may comprise a balloon catheter having a first balloon, a second balloon and at least one sensor associated with the second balloon. In some embodiments, the device comprises two sensors as described herein. In certain embodiments, the balloon catheter may further comprise a side aperture for infusing normal saline or medication.

FIGS. 26A-26G show yet another embodiment of the present disclosure. The catheter device 100 may comprise a catheter shaft 2600 actuated to deploy an occlusive element 2601 to occlude the renal artery openings. The occlusive element 2601 may, for example, be an expandable mesh braid. The expandable mesh braid may comprise a tubular, metal mesh braid comprising a plurality of mesh filaments. The expandable mesh braid may comprise a shape-memory material such as Nitinol and may be biased to be in the expanded configuration. The device may further comprise a position indication features, for example, at least a portion of the catheter device may be radio-opaque.

FIG. 26A shows a catheter shaft 2600 comprising an outer shaft 2602 and an inner shaft 2603 disposed therein which are translatable relative to one another. The distal end 2604 of the expandable mesh braid 2601 may be coupled to the inner shaft 2603 while the proximal end 2605 of the expandable mesh braid 2601 may be coupled to the outer shaft 2602 such that translation of the inner shaft 2603 relative to the outer shaft 2602 deploys or collapses the expandable mesh braid 2601. The catheter shaft 2600 may further comprise a cover 2606 to protect the catheter shaft device 100 during insertion into the abdominal aorta. The cover 2606 may be removed upon positioning the catheter shaft device 2600 at a desired location.

FIG. 26B shows the catheter shaft device 100 with expandable mesh braid 2601 coupled to the inner 2603 and outer 2602 shafts. The expandable mesh braid 2601 is shown in a low-profile configuration which may be used for delivery of the device 100 through the vasculature prior to deployment. The low-profile configuration may be axially elongated and radially collapsed.

FIG. 26C shows the catheter shaft device 100 following actuation of the inner shaft 2603 relative to the outer shaft 2602 for deployment of the expandable mesh braid 2601. The expandable mesh braid 2601 is shown in an expanded configuration such that the device 100 occludes the renal artery ostia (also referred to herein as orifices) to prevent contrast agent from flowing into the renal arteries of a patient when a bolus of the contrast agent has been introduced into the vasculature. The expanded configuration may be axially foreshortened and radially expanded. In the expanded configuration, the expandable mesh braid 2601 may comprise a minimally porous portion 2607, for example a high-density mesh brain filament portion. The minimally porous portion 2607 may be a region where the braid 2601 is axially foreshortened to increase filament density. The expandable mesh braid 2601 in the expanded configuration may comprise one or more porous end portions 2608 adjacent to the minimally porous portion 2607 so as to allow blood to flow through the braid 2601 from the supra-renal aorta to the infra-renal aorta, bypassing the occluded renal arteries. The one or more porous end portions 2607 may comprise low mesh braid filament density portions.

Actuation of the catheter shaft for deployment of the expandable mesh braid may, for example, comprise translating the inner and outer shafts such that the distal end of the outer shaft moves closer to the distal end of the inner shaft.

Figure 26D:
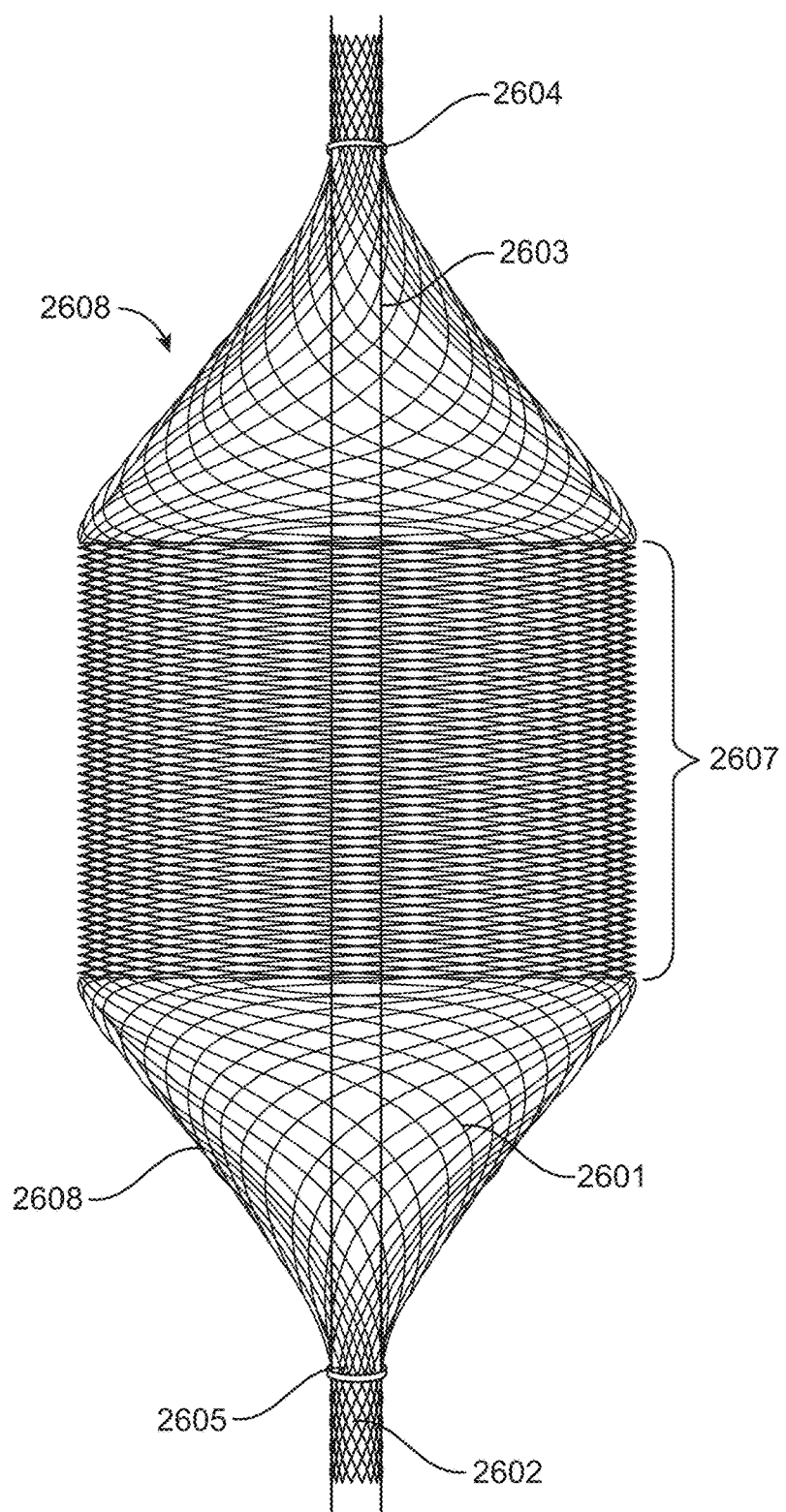
FIGS. 26D-26G show further embodiments of the present disclosure.
Figure 26E:
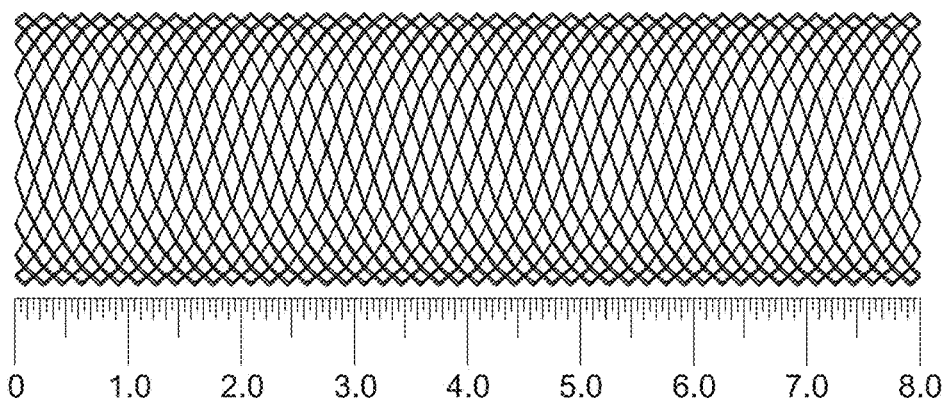
Figure 26F:
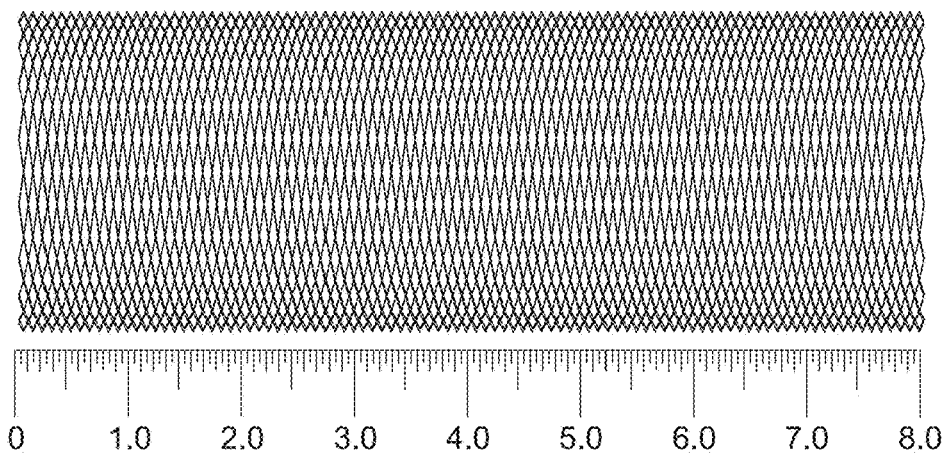
Figure 26G:
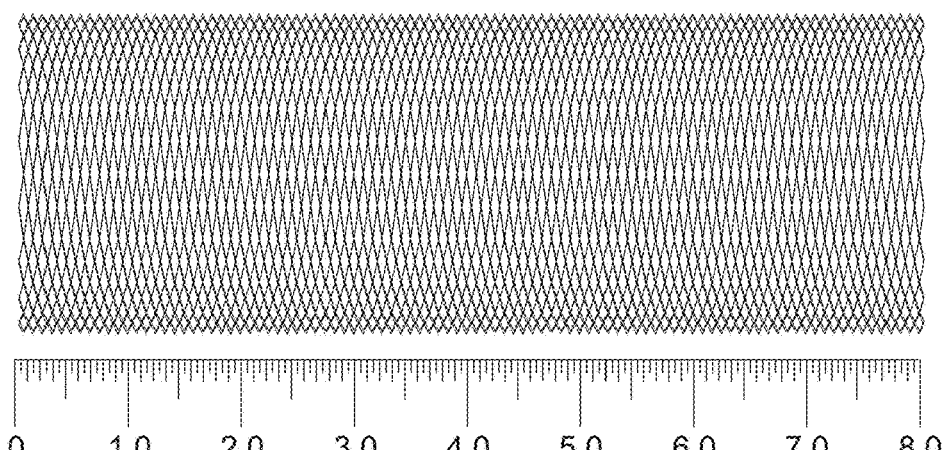

FIG. 26D shows a prototype of a catheter shaft device 2600 with expandable mesh braid 2601. The embodiment comprises a tubular metal mesh braid 2601 comprising a plurality of mesh filaments made of Nitinol, an outer shaft 2602, and an inner shaft 2603. The distal end 2604 of the expandable mesh braid 2601 is coupled to the inner shaft 2603 while the proximal end 2605 of the expandable mesh braid 2601 is coupled to the outer shaft 2602. Translation of the inner shaft 2603 relative to the outer shaft 2602 deploys or collapses the expandable mesh braid. In its expanded configuration, the expandable mesh braid 2601 comprises a minimally porous portion 2607 with which to occlude the orifices of the renal arteries. The expandable mesh braid further comprises two porous end portions 2608 which may allow blood to flow through the braid 2601 from the supra-renal aorta to the infra-renal aorta, bypassing the occluded renal arteries. FIG. 26E shows the expandable mesh braid 2601 with fully open mesh. FIG. 26F shows the expandable mesh braid 2601 with a partially collapsed mesh. FIG. 26G shows the expandable mesh braid 2601 with fully collapsed mesh.

The catheter shaft device 100 may further comprise a time-delayed release mechanism configured to automatically collapse the expandable mesh braid after a pre-determined amount of time following deployment. The time-delayed release mechanism may, for example, comprise an energy accumulation and storage component and a time-delay component. For example, the time-delayed release mechanism may comprise a spring with a frictional damper, an example of which is described in FIG. 31. The energy accumulation and storage component may for example be a spring or spring-coil or the like. The time-delayed release mechanism may for example be adjustable by one or more of the user, the manufacturer, or both. The time-delayed release mechanism may further comprise a synchronization component to synchronize the injection of a contrast media or other harmful agent with the opening or closing of the catheter shaft device. For example, injection may be synchronized with occlusion of the renal arteries by the expandable mesh braid such that a contrast media may be prevented from entering the renal arteries.

Figure 27A:
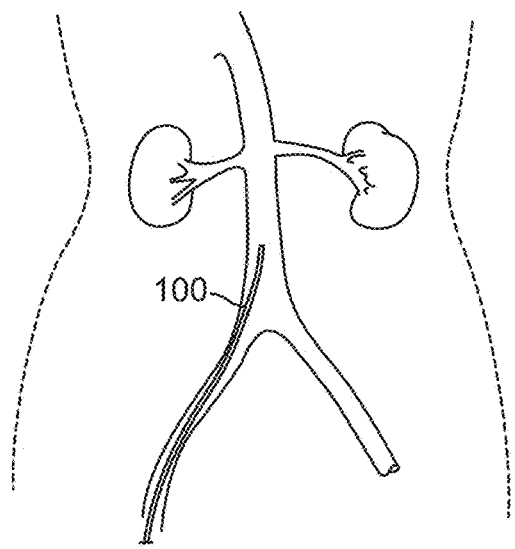
FIGS. 27A-27D show the deployment of the embodiment of FIGS. 26A-26G.
Figure 27B:
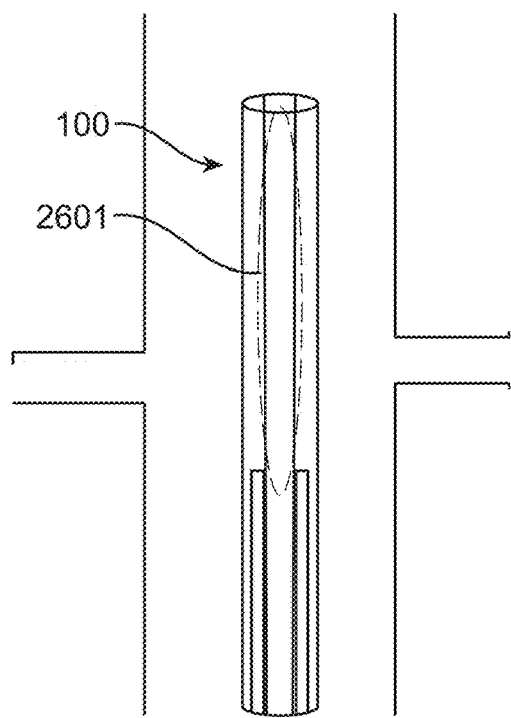
Figure 27C:
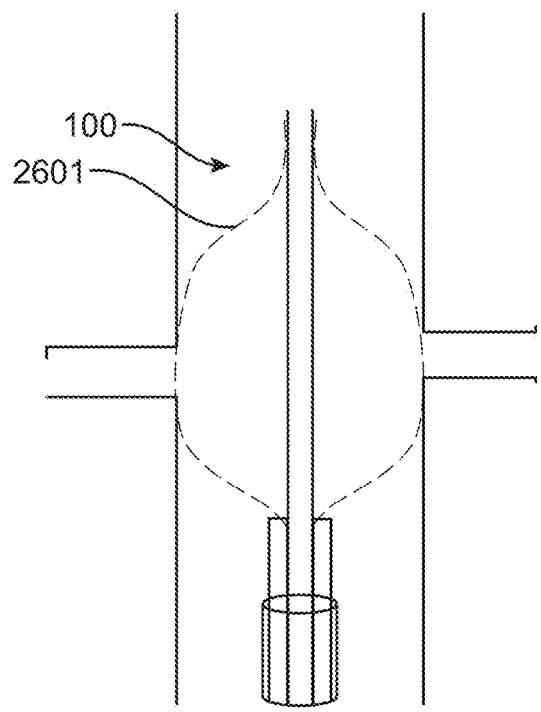
Figure 27D:
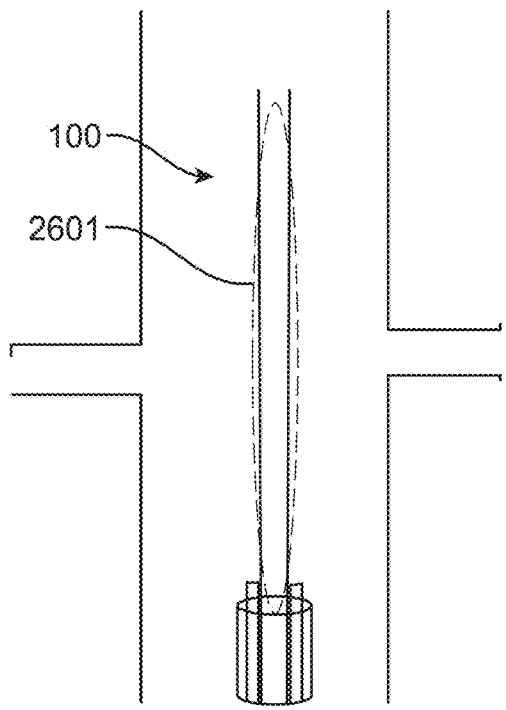

FIGS. 27A-27D show the deployment of the embodiment of FIGS. 26A-26G. Similar deployment steps may be used for all of the embodiments described herein. As shown in FIG. 27A, the device 100 may be inserted into the abdominal aorta via the femoral artery. Alternatively, the device 100 may be inserted into the abdominal aorta via the branchial or radial arteries. As shown in FIG. 27B, the device 100 may be guided to a desired location within the abdominal aorta by monitoring a position indication means, for example a radio-opaque marker or a radio-opaque portion of the catheter. The device 100 may for example be positioned such that deployment of the expandable mesh braid 2601 occludes the orifices of the renal arteries. FIG. 27C shows the expandable mesh braid 2601 deployed at a desired position so as to occlude the orifices of the renal arteries. The expandable mesh braid 2601 may be deployed prior to or simultaneously with injection of a contrast agent into the abdominal aorta of a patient so as to prevent the contrast agent from entering the renal arteries. After the bolus of contrast agent has been introduced, the expandable mesh braid 2601 may be collapsed to allow blood flow to the renal arteries to resume, as shown in FIG. 27D.

The expandable mesh braid may for example be made of a superelastic material such as nitinol. The braid may be made of any superelastic or pseudoelastic material, for example nitinol, alloys of copper-zinc-aluminum (CuZnAl), alloys of copper-aluminum-nickel (CuAlNi), alloys of copper-aluminum, alloys of nickel-titanium, or any combination thereof. In some embodiments, the superelastic material may comprise one or more of copper, aluminum, nickel, titanium, or any combination thereof. The expandable mesh braid may for example be made of steel or any other mesh-grade material. The expandable mesh braid may be coated with a hydrophobic coating, a hydrophilic coating, or a tacky coating for enhanced flow diversion. The shape of the braid may be adjusted to better fit into the geometry of the abdominal aorta, for example the diameter of the lower part of the braid may be smaller than the diameter of the upper part of the braid.

Figure 28A:
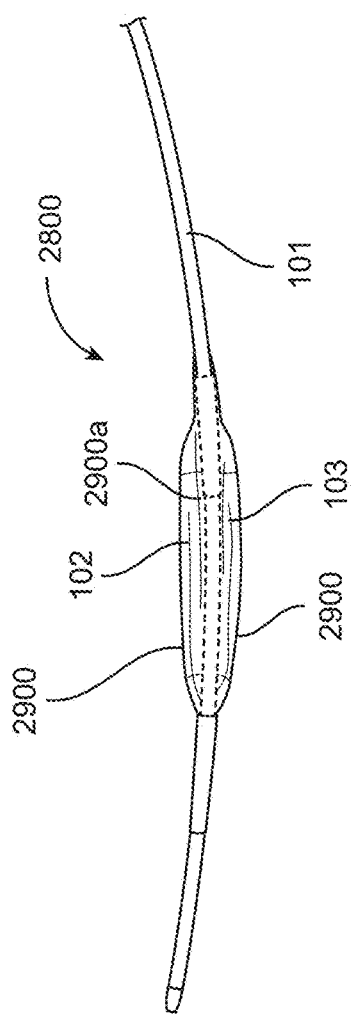
FIGS. 28A-28C show a further embodiment of the present disclosure.
Figure 28B:
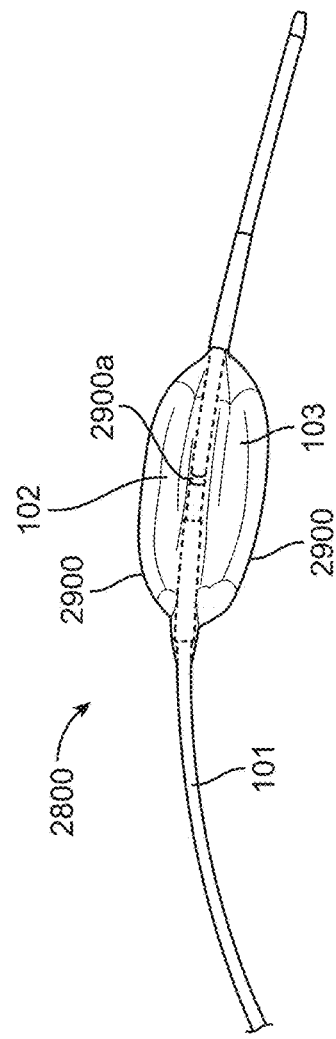
Figure 28C:
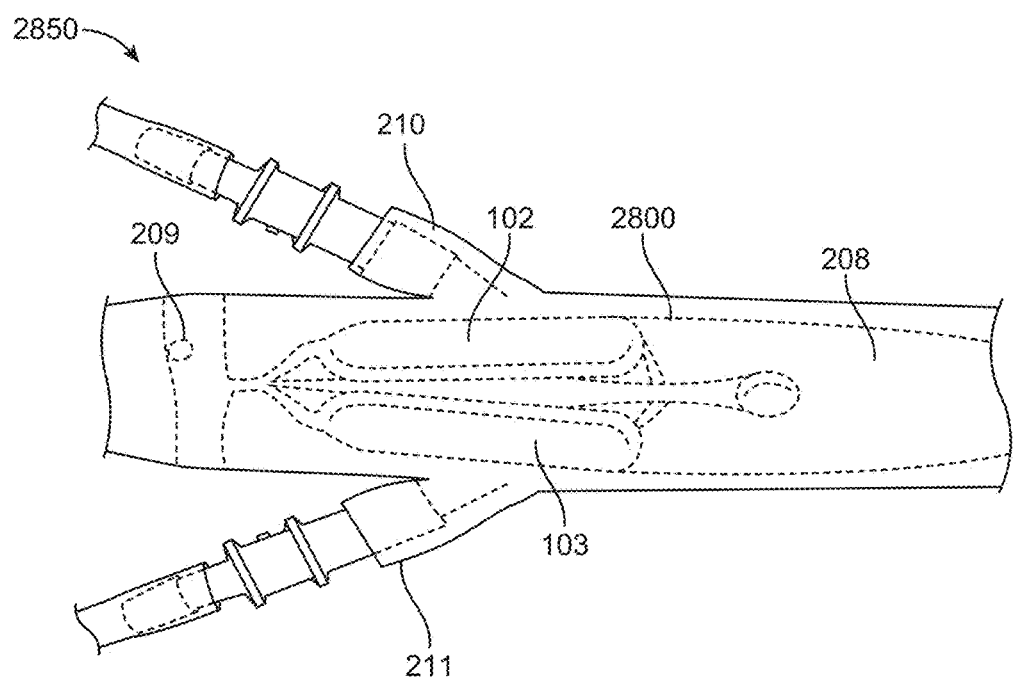

FIGS. 28A-28C show another embodiment of the present disclosure. The catheter device 2800 may comprise a catheter 101 with a first balloon 102 and a second balloon 103 disposed on a proximal portion thereof. The first balloon 102 may be disposed on a first lateral side of the proximal portion of the catheter 101. The second balloon 103 may be disposed on a second lateral side of the proximal portion of the catheter 101, for example opposite the first balloon 102.

FIG. 28A shows a prototype of a balloon catheter device 2800 having two ellipsoidal balloons 102 and 103 in a collapsed configuration. FIG. 28B shows the device 2800 in an expanded configuration. The first and second balloons 102, 103 may for example be ellipsoidal as shown. The balloons 102, 103 may form a dumb-bell or butterfly-like shape about the catheter 101 in cross-section when expanded from the collapsed configuration (FIG. 28A) to the expanded configuration (FIG. 28B). The balloons 102, 103 may be shaped so as to occlude the left and right renal arteries when expanded while allowing blood to flow between the balloons 102, 103 along the catheter shaft 101. In some instances, the balloons 102, 103 may be a single balloon disposed about the catheter 101 with a first balloon portion and a second balloon portion shaped similarly to the first and second balloons 102, 103 described herein. As discussed further below, a position indication feature 2900 may be disposed on the surfaces of the balloons 102, 103 to facilitate the determination of the position of the balloons 102, 103 and of whether the renal artery ostia are occluded. As shown in FIGS. 28A and 28B, the position indication feature 2900 may comprise a plurality of longitudinal radio-opaque markers and a radio-opaque marker 2900a disposed on the catheter 101 between the balloons 102, 103.

FIG. 28C shows the device 2800 in the expanded configuration inside a model abdominal aorta 2850. The catheter balloon device 2800 is shown positioned within a model abdominal aorta 2850. Generally, the one or more balloons 102, 103 may be positioned adjacent the orifices of the right renal artery 210 and the left renal artery 211, for example spanning between the supra-renal aorta 208 and the infra-renal aorta 209, thereby controlling blood flow to any of the right renal artery 210, left renal artery 211 and/or infra-renal aorta 209. While occluding the renal arteries 102, 103, the balloons 102, 103 may not completely occlude the aorta 2850 and may allow blood flow through the gaps between the balloons 102, 103 and the catheter 101. In cross-section, the expanded balloons 102, 103 may assume a dumbbell or butterfly shape, for example, as described herein.

Generally, the balloons 102, 103 may be of any size and/or shape. In particular the size and/or shape may be selected to control the amount of occlusion for each of the left and right arteries. For example, the renal arteries may be located at different distances down the length of the aorta (e.g., viewing the aorta along the coronal plane, the left and right renal arteries may branch away from the aorta at different distances from the aortic arch). In such instances, it may be beneficial to employ balloons that are ellipsoidal (e.g., greater in length along a longitudinal direction of the aorta than in diameter), thereby capable of occluding both the left and right renal artery upon being placed in the initial position. In some instances, the renal arteries may branch at different angles (as viewed along the axial plane) from the aorta between subjects or groups of subjects. In such instances, it may be beneficial to employ balloons which are positioned to match the branching architecture of the patient or group of patients (e.g. balloons which are positioned opposite one another on the catheter for patients with branching opposite one another or balloons which are position less than 180° apart about the catheter for patients with branching less than 180° apart). In some instances, it may be beneficial to employ balloons shaped to deform when contacting the aorta and "spread" along the wall in order to occlude a typical range of angles for a particular group of subjects. In some instances it may be beneficial to employ balloons sized or shaped to occlude a typical range of angles for a particular group of subjects. The typical range of angles may vary from subject group (e.g. patient population) to subject group and the spread, angle, size, and/or shape of the balloons may be configured to perform for a particular subject group based on the typical range of branching angles. In some embodiments, the size and/or shape of the balloon may be specific for a particular group of subjects. For example, younger subjects (e.g., under 15 years of age) may require balloons that are shorter in length and/or width (e.g., in an un-inflated state) as compared to adults (e.g., 15 years of age and older). In another example, balloons of a particular size and/or shape may be suitable for subjects originating from a given geographical location or ethnic background due to genetic and physiological variations between subjects or groups of subjects (e.g., Asians vs. Caucasians). Non-limiting examples of balloon length include about 1 millimeter (mm), about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, 41 mm, about 42 mm, about 43 mm, about 44 mm, about 45 mm, about 46 mm, about 47 mm, about 48 mm, about 49 mm, about 50 mm, about 60 mm, about 70 mm, about 80 mm, about 90 mm, about 100 mm, or greater than about 100 mm. Non-limiting examples of balloon diameter include about 1 millimeter (mm), about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm, about 30 mm, about 31 mm, about 32 mm, about 33 mm, about 34 mm, about 35 mm, about 36 mm, about 37 mm, about 38 mm, about 39 mm, about 40 mm, 41 mm, about 42 mm, about 43 mm, about 44 mm, about 45 mm, about 46 mm, about 47 mm, about 48 mm, about 49 mm, about 50 mm, about 60 mm, about 70 mm, about 80 mm, about 90 mm, about 100 mm, or greater than about 100 mm. In some embodiments, the diameter of the balloon may change from a proximal end of the balloon to a distal end of the balloon. For example, the balloon may be cigar-shaped, torpedo-shaped, or submarine-shaped. The balloon may be any shape suitable for occluding one or more arteries (e.g., renal arteries). Non-limiting examples of balloon shapes include spherical, ellipsoidal, cylindrical, an n-sided prism (pentagonal or hexagonal) where n is any number, conical, and pyramidal.

In some embodiments, one or more balloons of the device may be inflatable. Inflation of the balloon may expand the balloon to occlude the artery. In some embodiments having two or more balloons, the balloons may be fluidly-connected, and may be inflated together. In other embodiments, the balloons may not be fluidly connected, and may be capable of independently inflating. In some embodiments, the balloons may be fluidly connected, wherein a fluid connection may be opened or closed as needed, thereby allowing inflation of two or more balloons together or inflation of each balloon separately. Any number of balloons may be used. A device of the present disclosure may have a single balloon. A device of the present disclosure may have two or more balloons. Non-limiting examples of a multi-balloon device include a device comprising 2 balloons, 3 balloons, 4 balloons, 5 balloons, 6 balloons, 7 balloons, 8 balloons, 9 balloons, 10 balloons, and more than 10 balloons. In some embodiments, one or more balloons of the device may be inflated, and the inflation of the balloon may be synchronized with an injection of a contrast dye (e.g., Urografin) into the subject. In some embodiments, the contrast dye injection may be performed prior to inflating the one or more balloons in the device. In some embodiments, the contrast dye injection may be performed simultaneously with the inflation of the one or more balloons in the device. In some embodiments, the one or more balloons in the device may be inflated prior to or after injection of the contrast dye into the subject.

FIGS. 29A-29D show an embodiment of a position indication feature 2900 which can be used to determine if a balloon catheter device occludes the orifices of an artery such as the renal arteries. The renal arteries are not shown for simplicity. FIGS. 29A-29B depict an axial view along the aorta 2950, for example an abdominal, depicting the relative positions of the first 102 and second 103 catheter balloons in the initial position (FIG. 29A) and the "protective" or inflated position (FIG. 29B). FIGS. 29C and 29D show the position indication feature 2900 in the initial position (FIG. 29C) and the "protected" or expanded position (FIG. 29D). The position indication feature 2900 may be used to help identify the position of the catheter within the abdominal aorta 2950 and/or whether of or not the renal arteries have been occluded upon expansion of the first and second balloons 102, 103. The position indication feature 2900 may for example comprise one or more radio-opaque longitudinal markers as shown. The radio-opaque longitudinal markers may be observed or monitored within the abdominal aorta during positioning of the occlusive element (e.g. first and second balloons 102, 103) within the abdominal aorta 2950 using x-ray imaging and used to guide positioning of the occlusive element adjacent the renal arteries and/or confirm occlusion of the renal arteries. When unexpanded during positioning (FIGS. 29A, 29C), the radio-opaque longitudinal markers may appear straight within the abdominal aorta 250. Expansion of the balloons 102, 103 and occlusion of the renal arteries may confirmed by the appearance of a bowed section, or "nipple", in the radio-opaque longitudinal markers. FIG. 29D shows "nipples" 2901 and 2902 which may be used as artery (e.g., renal artery) orifice locators. Such "nipples" 2901, 2902 may be formed when the balloons 102, 103 are expanded and the flexible outer surface of the balloons 102, 103 curve to partially enter and occlude the left and right renal artery ostia. In the initial, unexpanded configuration (FIGS. 29A and 29C), the radio-opaque longitudinal markers 2900 are straight; and in the protective, expanded position (FIGS. 29B and 29D), the outer most radio-opaque longitudinal markers 2900 are curved outwardly at the renal arteria ostia.

Alternatively or in combination, at least a portion of the catheter, first balloon 102, second balloon 103, or a combination thereof may comprise a radio-opaque material or radio-opaque marker thereon as described herein. Alternatively or in combination, one or more of the balloons may be inflated with a radio-opaque material as described herein. Similar bowing (e.g. "nipple" formation) may be observed with a balloon made of or inflated with a radio-opaque material for example.

Figure 30:
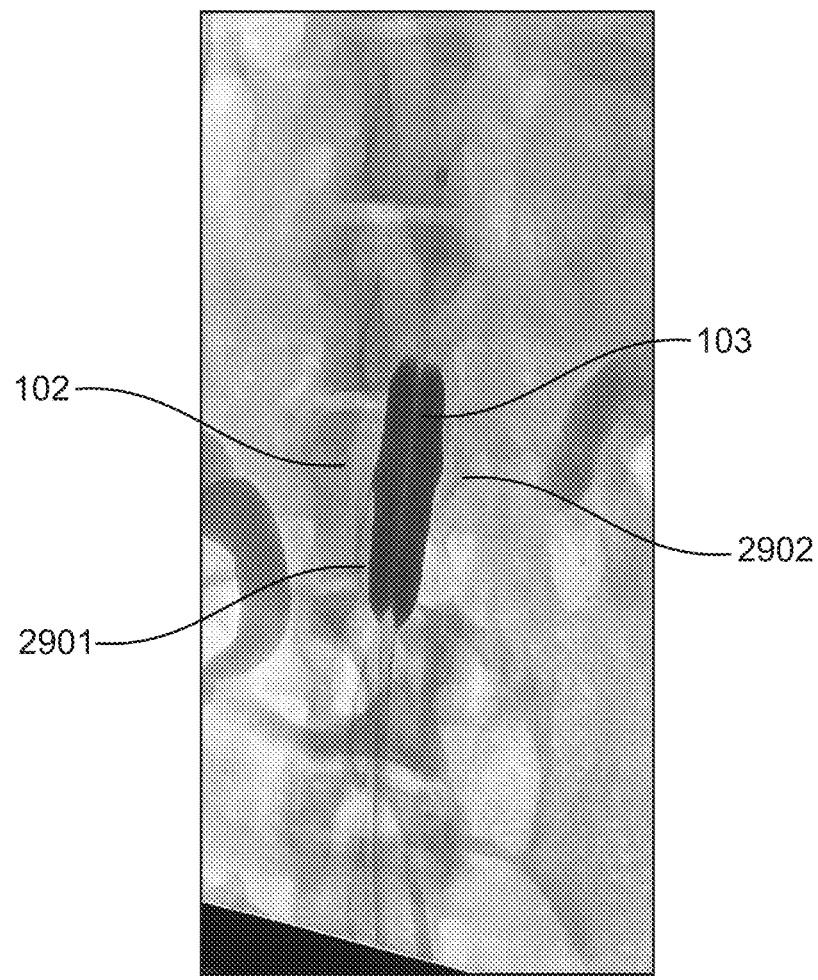
FIG. 30 shows an X-Ray of the balloon catheter of FIGS. 28A-28C inserted into a subject, with the balloons in the "protective" position.

FIG. 30 shows an X-Ray image of the device 2800 of FIGS. 28A-28C comprising a first balloon 102 and a second balloon 103 inserted into a subject, with the balloons 102, 103 expanded to be in the "protective" or occlusive position. Arrows identify "nipples" 2901 and 2902 which indicated that the expanded balloons 102, 103 have occluded the renal arteries as described herein. For example, the balloons 102, 103 may be inflated with a radiopaque fluid such that the formation of the "nipples" 2901 and 2902 are visible in X-Ray. In cases where the balloons 102, 103 are expanded with a non-radiopaque fluid such as carbon dioxide or saline, the formation of the "nipples" 2901 and 2902 may be indicated by observing the shape of radio-opaque longitudinal markers, such as those described in FIGS. 29C-29D, on the surface of the balloons 102, 103.

Figure 31:
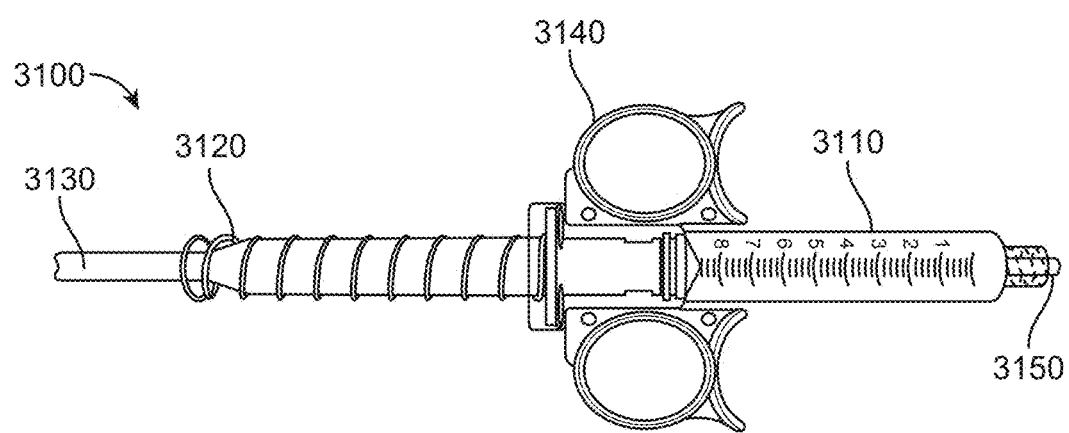
FIG. 31 shows an embodiment of a time-delayed release mechanism configured to automatically collapse the occlusive element after a pre-determined amount of time following deployment.

FIG. 31 shows an embodiment of a time-delayed release mechanism 3100 configured to automatically collapse the occlusive element after a pre-determined amount of time following deployment. Any of the devices described herein may further comprise a time-delayed release mechanism 3100. The time-delayed release mechanism 3100 may be configured to facilitate expansion and subsequent collapse any of the expandable occlusive elements described herein after a pre-determined amount of time following deployment or expansion of the occlusive element. For example, the time-delayed release mechanism 3100 may be used to automatically collapse an expandable mesh braid or deflate a balloon after a pre-determined amount of time. The time-delayed release mechanism may, for example, comprise an energy accumulation and storage component and a time-delay component. For example, the time-delayed release mechanism may comprise a spring with a frictional damper. The energy accumulation and storage component may for example be a spring or spring-coil or the like. The time-delayed release mechanism 3100 may for example comprise a syringe 3110 and a spring 3120 disposed around a syringe pump 3130. The tip 3150 of the syringe 3110 may be configured to attach to the distal end of the catheter device (not shown), for example via a press-fit, screw-fit, or luer-lock connector. The release mechanism 3100 may further comprise a handle 3140 which the user may grip while depressing the syringe pump 3130 and attached spring 3120 into the syringe 3110 to expand the occlusive element (not shown). Actuation of the syringe pump 3130 may, in the case of a balloon catheter for example, force a fluid (e.g. liquid or gas) into the balloon(s) via the tip connection 3150 to the catheter device in order to inflate and expand the balloon(s) to an expanded configuration. Removal of the pressure applied to the syringe pump 3130 may cause the spring 3120 to release the energy it accumulated by being depressed and quickly retract the syringe pump 3130 from its depressed position within the syringe 3110 to deflate and collapse the balloon after a pre-determined amount of time. Actuation of the syringe pump 3130 may, in the case of the braided mesh, cause an inner shaft to translate relative to an outer shaft of the catheter as described herein in order to deploy (e.g. expand) the expandable mesh braid to an expanded configuration. Removal of the pressure applied to the syringe pump 3130 may cause the spring 3120 to release the energy it accumulated by being depressed and quickly retract the syringe pump 3130 from its depressed position within the syringe 3110 to collapse the expandable mesh brain after a pre-determined amount of time. The time-delayed release mechanism 3120 may further comprise a frictional damper configured to introduce the pre-determined amount of time between the inflation of the balloon, release of the syringe pump 3130, and the release of energy by the spring 3120. It will be understood by one of ordinary skill in the art that the amount of friction applied by the damper to the syringe pump 3130 and/or spring 3120 may be calibrated to generate any pre-determined time-delay desired such as by providing the spring 3120 with various spring constants depending on the time-delay desired.

The time-delayed release mechanism 3100 may for example be adjustable by one or more of the user, the manufacturer, or both. The time-delayed release mechanism 3100 may further comprise a synchronization component to synchronize the injection of a contrast media or other harmful agent with the opening or closing of the catheter shaft device as described herein. For example, injection may be synchronized with occlusion of the renal arteries by the first and second balloons or the expandable mesh braid such that a contrast media may be prevented from entering the renal arteries.

Figure 32:
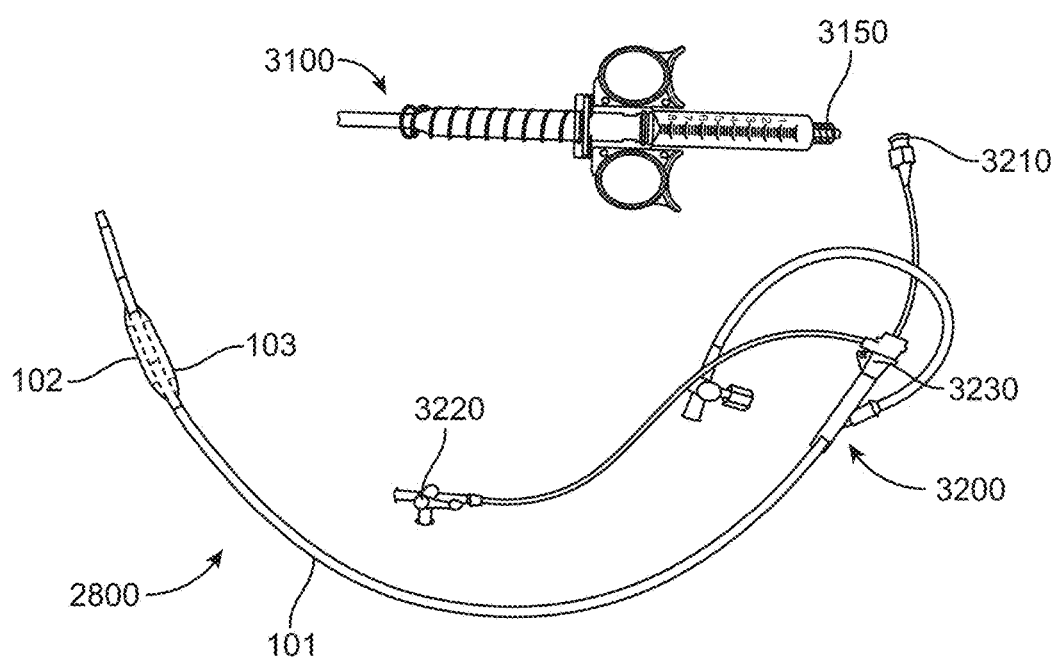
FIG. 32 shows a further embodiment of the present disclosure including the prototype of FIGS. 28A-28C and the time-delayed release mechanism of FIG. 31.

FIG. 32 shows a further embodiment of the present disclosure including the prototype 2800 of FIGS. 28A-28C and the time-delayed release mechanism 3100 of FIG. 31. The catheter device 2800 may comprise a catheter 101 with a first balloon 102 and a second balloon 103 on a proximal portion thereof as described herein. A distal portion 3200 of the catheter 101 may comprise a connection element 3210 configured to connect to the tip 3150 of the time-delayed release mechanism 3100. The distal portion 3200 of the catheter 101 may be configured to remain external to the subject when the first and second balloons 102, 103 are positioned adjacent the renal arteries of the subject. The catheter 101 and the syringe 3110 may be fluidly connected, for example to allow a fluid to pass from the syringe 3110 to the catheter 101 and into the balloons 102, 103 via the catheter 101. Actuation of the time-delayed release mechanism 3100 may expand the balloons 102, 103 with the fluid as described herein. The distal portion 3200 of the catheter 101 may comprise one or more infusion port 3220 as described herein. The infusion port 3220 may for example be configured to infuse a medication or other fluid (e.g. normal saline) into the aorta, for example via a side aperture in the catheter 101 (not shown) as described herein. The distal portion 3200 of the catheter 101 may further comprise one or more orientation indication feature 3230. The orientation indication feature 3230 may be configured to indicate the orientation of the occlusive element, in this example the first and second balloons 102, 103, when positioned adjacent renal artery ostia of the subject. The orientation indication feature 3230 may for example comprise one or more of a visible marking, a protrusion, a wing, a flag, or the like. The orientation indication feature 3230 may be aligned with the first and second balloons 102, 103 in a particular manner such that the orientation of the orientation indication feature 3230 outside of the subject may be indicative of the orientation of the first and second balloons 102, 103 inside the subject. For example, the orientation indication feature 3230 may comprise a pair of wings as shown which include a first wing aligned (i.e., facing the same radially outward direction as) with the first balloon 102 and a second wing aligned with (i.e., facing the same radially outward direction as) the second balloon 103. The catheter 101 may be sufficiently stiff such the orientation indication feature 3230 maintains alignment with the balloons 102, 103 as the catheter 101 is torqued or rotated. For example, the orientation indication feature 3230 may be configured to lie approximately parallel to (or alternatively face perpendicularly away from or towards, or be otherwise oriented in relation to) the ground when the first and second balloons 102, 103 are properly positioned within the abdominal aorta adjacent the renal arteries of the subject. It will be understood by one of ordinary skill in the art that any of the catheter devices described herein may be attached to a time-delayed release mechanism 3100, comprise one or more infusion port 3220, and/or comprise one or more orientation indication feature 3230 in a similar manner as described herein.

Example 1: Effects of Total Volume Versus Instantaneous Concentration on Contrast Dye-Induced Nephropathy In order to test that contrast media toxicity to kidneys is determined more by influx contrast media concentration and not by total amount of contrast media introduced, Sprague-Dawley (SD) rats were either given bolus injections or continuously infused with Urografin radiographic agent to deliver a same total dose of 20 milligrams (mg) of agent per kilogram (kg) of body weight ($LD_{50}$=20 mg/kg). Urografin was administered intra-arterially over a period of 20 minutes (e.g., either 4 equal bolus injections or a continuous infusion at a lower concentration). SD rats receiving a bolus injection (e.g., a current standard for administering a radiographic agent) represented a control group, while SD rats receiving continuous administration (e.g., simulating the effects of kidney protection with balloon-catheter renal artery occlusion) represented the test group. Mortality was measured at 5 hours and 24 hours following administration of the radiographic agent. Tissue biopsies were obtained, and nephropathy was assessed 5 hours following administration of the radiographic agent by measuring the increase in serum creatine over baseline serum creatine.

SD rats receiving the bolus administration of radiographic agent exhibited about 30% and 75% mortality rate 5 hours and 24 hours following administration of the agent, respectively. In contrast, SD rats receiving the continuous administration of radiographic agent (e.g., at a lower concentration as compared to the bolus injection) exhibited about 8% and 33% mortality rate 5 hours and 24 hours following administration of the agent, respectively. Continuous administration of the radiographic agent at lower concentrations yielded about a 73% and 56% reduction in mortality rate 5 hours and 24 hours following administration of the agent, respectively, as compared to administration using a bolus injection. Furthermore, only about 10% of SD rats receiving the bolus administration of radiographic agent were free of contrast nephropathy 5 hours following administration of the agent, as compared to 30% of SD rats receiving the continuous administration of radiographic agent (e.g., at a lower concentration as compared to the bolus injection). Overall, delivery of the same total dose of radiographic agent at a lower concentration rate reduced kidney toxicity and injury.

Example 2: Balloon Catheter Shape Affects Renal Artery Occlusion

Branching arterial geometry and branching patterns from the abdominal aorta vary across the patient population. To determine the variability across the patient population, approximately 400 Chinese patients were screened, with 30 patients selected for enhanced CT screening. The results of the screening are provided below in Tables 1 and 2. Results are shown as mean±standard deviation (STD). Table 1 shows demographic information for the 30 patients selected for enhanced CT screening. Table 2 shows the variation in the diameters of the supra-renal aorta, renal aorta, and infra-renal aorta for the 30 patients selected for contrast enhanced CT screening.

TABLE 1

Demographic information of the patient population

| | Height (cm) | Weight (kg) | Body Surface Area ($mm^2$) | Age | Gender |
|---|---|---|---|---|---|
| Mean (mm) | 163.9 | 57.7 | 1.58 | 64.3 | 19M/11F |
| STD (mm) | 7.7 | 12.7 | 0.16 | 15.4 | |

TABLE 2

Patient variation in the geometry of the supra-renal, renal, and infra-renal aorta

| | Supra-renal aorta (mm) | | Renal aorta (mm) | | Infra-renal aorta (mm) | |
|---|---|---|---|---|---|---|
| Mean (mm) | 20.4 | 18.3 | 19.0 | 16.9 | 17.4 | 16.1 |
| STD (mm) | 2.2 | 2.2 | 2.1 | 2.3 | 2.9 | 2.4 |

In addition to the geometry of the orifice of the supra-renal, renal, and infra-renal aorta, the branching pattern of the renal arteries also varied across patients. The angle at which the renal arteries branched (as viewed along the axial plane within the abdominal aorta) was equated to the hours on a clock face with 6 o'clock facing anteriorly (or towards the front of the subject) and 12 o'clock facing posteriorly (or towards the back of the subject). In a group of 24 selected patients, the right renal artery was positioned at 9 o'clock, 10 o'clock, and 11 o'clock in 11 patients, 12 patients, and 1 patient, respectively. Additionally, in the same group of 24 patients, the left renal artery was positioned at 2 o'clock, 3 o'clock, and 4 o'clock in 1 patient, 20 patients, and 3 patients, respectively. Due the variability in arterial geometry and branching patterns, we hypothesized that the shape of the catheter balloon can affect renal occlusion.

Example 3: Effects of Renal Artery Occlusion (e.g., Renal Cell Ischemia) on Kidney Cell Viability Cell samples were prepared by differentiating induced pluripotent stem cells into nephrons. Cells were cultured for 4 days post-differentiation, changing media every 3 days, before performing experiments. Samples were either cultured under standard conditions or under ischemic conditions for up to 24 hours. At periods of 1 minute, 5 minutes, 30 minutes, 5 hours and 24 hours, the samples were incubated in Hoeschst 33342 to indicate cell nuclei. Cells were imaged using the INCell Analyzer2200, and images were analyzed to quantify the total number of cells and plotted as a percentage of total cells normalized to control, where each data point was obtained from three biological replicates. An increase in Hoechst 33342 signal represented an increase in cell viability.

The viability of cells cultured under standard conditions was not significantly different than the viability of cells cultured under ischemic conditions (either reduced oxygen or oxygen-free) up to 1 hour. These results suggest that shorter periods (e.g., seconds) of renal artery occlusion (e.g., renal cell ischemia) do not have an adverse effect on cell viability.

While preferred embodiments of the present disclosure have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A device for preventing acute kidney injury from contrast agent introduced into vasculature of a subject, the device comprising:
    a catheter shaft comprising proximal portion and a distal portion;
    an occlusive element disposed on the proximal portion; and
    at least one longitudinal position indication feature on the occlusive element,
    wherein the occlusive element has an expanded configuration in which, when advanced into an abdominal aorta and positioned adjacent renal artery ostia of the subject, is sized to occlude the renal artery ostia while allowing blood flow over the catheter shaft, and
    wherein the distal portion is configured to remain outside a body of the subject when the proximal portion is positioned adjacent renal artery ostia of the subject,
    wherein the occlusive element comprises a first expandable member disposed on a first lateral side of the proximal portion and a second expandable member disposed on a second lateral side of the proximal portion, the first and second expandable members being disposed in parallel about the catheter shaft, and
    wherein the first and second expandable members have an expanded configuration in which, when advanced into an abdominal aorta and positioned adjacent renal artery ostia of the subject, are sized to occlude the renal artery ostia while allowing blood flow over the catheter shaft.

2. The device of claim 1, wherein the first expandable member and the second expandable member are in fluid communication with one another.

3. The device of claim 1, wherein the first expandable member and the second expandable member are fluidly independent of one another.

4. The device of claim 1, wherein the first expandable member and the second expandable member comprise a single balloon.

5. The device of claim 1, wherein the first expandable member comprises a first balloon and the second expandable member comprises a second balloon.

6. The device of claim 1, wherein the expanded configuration of the occlusive element is spherical, ellipsoidal, cylindrical, an n-sided prism, conical, pyramidal, butterfly-shaped, dumbbell-shaped, cigar-shaped, torpedo-shaped, or submarine-shaped.

7. The device of claim 1, further comprising one or more position indication feature is disposed on the proximal portion of the catheter shaft adjacent the occlusive element.

8. The device of claim 7, wherein the one or more position indication feature comprises one or more radio-opaque markers.

9. The device of claim 1, wherein the at least one longitudinal position indication feature comprises at least one longitudinal radio-opaque marker.

10. The device of claim 9, wherein the at least one longitudinal radio-opaque marker comprises a plurality of longitudinal radio-opaque markers.

11. The device of claim 1, wherein the at least one longitudinal position indication feature is configured to form at least one straightened section and a bowed section when the occlusive element has been expanded to the expanded configuration and positioned adjacent the renal artery ostia of the subject to occlude the renal artery ostia, the bowed section bowing toward the renal artery ostia, and wherein the at least one longitudinal position indication feature is configured to remain in a straightened configuration when the occlusive element has been expanded to the expanded configuration within a blood vessel but has not been positioned adjacent any blood vessel ostia.

12. The device of claim 1, wherein the at least one longitudinal position indication feature is disposed on the occlusive element along a longitudinal axis of the occlusive element.

13. The device of claim 1, further comprising a rotational orientation element disposed on the distal portion of the catheter shaft, the rotational orientation element aligned with the occlusive element and configured to indicate the rotational orientation of the occlusive element when positioned adjacent renal artery ostia of the subject while remaining outside the body of the subject.

14. The device of claim 13, wherein the orientation element comprises one or more of a visible marking, a protrusion, a wing, or a flag.

15. The device of claim 1, wherein the occlusive element comprises one or more of a mesh braid, an expandable member, or an inflatable balloon.

16. A system for preventing acute kidney injury from contrast agent introduced into vasculature of a subject, the system comprising:
    the device of claim 1; and
    a time-delayed release mechanism in communication with the occlusive element of the device, wherein the time-delayed release mechanism is configured to automatically collapse the occlusive element after a pre-determined amount of time following expansion of the occlusive element.

17. The system of claim 16, wherein the time-delayed release mechanism comprises an energy accumulation and storage component.

18. The system of claim 17, wherein the energy accumulation and storage component comprises a spring.

19. The system of claim 18, wherein the energy accumulation and storage component comprises a syringe comprising a plunger, and wherein the spring is coupled to the plunger.

* * * * *